(12) United States Patent
Sheldon et al.

(10) Patent No.: US 11,819,697 B2
(45) Date of Patent: Nov. 21, 2023

(54) METHOD AND APPARATUS FOR ADJUSTING CONTROL PARAMETERS FOR CARDIAC EVENT SENSING

(71) Applicant: Medtronic, Inc., Minneapolis, MN (US)

(72) Inventors: Todd J. Sheldon, North Oaks, MN (US); Keelia M. Escalante, Minneapolis, MN (US); Greggory R. Herr, Blaine, MN (US); Juliana E. Pronovici, New Hope, MN (US); Vincent E. Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 12 days.

(21) Appl. No.: 17/159,596

(22) Filed: Jan. 27, 2021

(65) Prior Publication Data

US 2021/0236825 A1    Aug. 5, 2021

Related U.S. Application Data

(60) Provisional application No. 62/967,917, filed on Jan. 30, 2020.

(51) Int. Cl.
*A61N 1/36* (2006.01)
*A61N 1/365* (2006.01)
(Continued)

(52) U.S. Cl.
CPC ......... *A61N 1/36542* (2013.01); *A61N 1/025* (2013.01); *A61N 1/3756* (2013.01); *A61N 1/37512* (2017.08); *G16H 20/30* (2018.01);
*G16H 40/67* (2018.01); *G16H 50/30* (2018.01); *A61N 1/0573* (2013.01); *A61N 1/37211* (2013.01)

(58) Field of Classification Search
CPC .................................................. A61N 1/36542
USPC ........................................................ 607/119
See application file for complete search history.

(56) References Cited

U.S. PATENT DOCUMENTS

| 4,485,813 A | 12/1984 | Anderson et al. |
| 5,052,388 A | 10/1991 | Sivula et al. |

(Continued)

FOREIGN PATENT DOCUMENTS

| WO | 2016014352 A1 | 1/2016 |
| WO | 2018165289 A1 | 9/2018 |

OTHER PUBLICATIONS (PCT/US2021/015632) PCT Notification of Transmittal of the International Search Report and the Written Opinion of the International Searching Authority, dated Jul. 5, 2021, 9 pages.

(Continued)

*Primary Examiner* — Nicole F Lavert

(57) ABSTRACT

A medical device includes a motion sensor configured to produce a motion signal and a control circuit configured to set sensing control parameters and sense atrial events from the motion signal during ventricular cycles according to the sensing control parameters. In some examples, the control circuit is configured to determine a feature of the motion signal for at least some ventricular cycles, determine a metric of the motion signal based on the determined features, and adjust at least one of the sensing control parameters based on the metric.

32 Claims, 17 Drawing Sheets

(51) Int. Cl.
*A61N 1/02* (2006.01)
*A61N 1/375* (2006.01)
*G16H 40/67* (2018.01)
*G16H 50/30* (2018.01)
*G16H 20/30* (2018.01)
*A61N 1/372* (2006.01)
*A61N 1/05* (2006.01)

(56) References Cited

U.S. PATENT DOCUMENTS

| | | |
|---|---|---|
| 5,292,341 A | 3/1994 | Snell |
| 5,480,412 A | 1/1996 | Mouchawar et al. |
| 5,507,782 A | 4/1996 | Kieval et al. |
| 5,593,431 A | 1/1997 | Sheldon |
| 5,683,432 A | 11/1997 | Goedeke et al. |
| 5,885,471 A | 3/1999 | Ruben et al. |
| 6,044,297 A | 3/2000 | Sheldon et al. |
| 6,295,471 B1 | 9/2001 | Bornzin et al. |
| 6,625,490 B1 | 9/2003 | McClure et al. |
| 7,062,328 B1 | 6/2006 | Levine et al. |
| 7,130,681 B2 | 10/2006 | Gebhardt et al. |
| 7,483,745 B2 | 1/2009 | Amblard |
| 7,848,807 B2 | 12/2010 | Wang |
| 7,869,876 B2 | 1/2011 | Prakash et al. |
| 8,214,036 B2 | 7/2012 | Casset |
| 8,233,981 B2 | 7/2012 | Casset |
| 8,380,308 B2 | 2/2013 | Rosenberg et al. |
| 8,433,409 B2 | 4/2013 | Johnson et al. |
| 8,478,388 B2 | 7/2013 | Nguyen et al. |
| 8,532,785 B1 | 9/2013 | Crutchfield et al. |
| 8,541,131 B2 | 9/2013 | Lund et al. |
| 8,700,181 B2 | 4/2014 | Bornzin et al. |
| 8,909,329 B2 | 12/2014 | Prakash et al. |
| 8,923,963 B2 | 12/2014 | Bonner et al. |
| 8,996,109 B2 | 3/2015 | Karst et al. |
| 9,272,146 B2 | 3/2016 | Anselmi |
| 9,278,218 B2 | 3/2016 | Karst et al. |
| 9,775,982 B2 | 10/2017 | Grubac et al. |
| 10,080,900 B2 | 9/2018 | Ghosh et al. |
| 10,207,116 B2 | 2/2019 | Sheldon et al. |
| 10,286,214 B2 | 5/2019 | Demmer et al. |
| 10,328,270 B2 | 6/2019 | Demmer et al. |
| 10,449,366 B2 | 10/2019 | Splett et al. |
| 10,532,212 B2 | 1/2020 | Splett et al. |
| 2012/0095521 A1 | 4/2012 | Hintz |
| 2013/0079861 A1 | 3/2013 | Reinert et al. |
| 2015/0173655 A1 | 6/2015 | Demmer et al. |
| 2016/0023000 A1 | 1/2016 | Cho et al. |
| 2016/0113536 A1 | 4/2016 | Greenhut et al. |
| 2016/0114161 A1 | 4/2016 | Amblard et al. |
| 2017/0274213 A1 | 9/2017 | Ghosh et al. |
| 2018/0085588 A1* | 3/2018 | Splett .................. A61N 1/3756 |
| 2018/0085589 A1 | 3/2018 | Splett et al. |
| 2018/0117337 A1 | 5/2018 | Demmer et al. |
| 2018/0154154 A1 | 6/2018 | Sheldon et al. |
| 2018/0161580 A1 | 6/2018 | Demmer et al. |
| 2019/0308022 A1 | 10/2019 | Demmer et al. |
| 2020/0179707 A1 | 6/2020 | Splett et al. |
| 2020/0179708 A1 | 6/2020 | Splett et al. |
| 2021/0236826 A1 | 8/2021 | Sheldon et al. |

OTHER PUBLICATIONS (PCT/US2021/015627) PCT Notification of Transmittal of the International Search Report and the Written Opinion of the International Searching Authority, dated May 14, 2021, 14 pages.
C00019138.W002 (PCT/US2019/064657) PCT Notification of Transmittal of the International Search Report and the Written Opinion of the International Searching Authority, dated Feb. 28, 2020, 8 pages.
C00019138W001 (PCT/US2019/064653) PCT Notification of Transmittal of the International Search Report and the Written Opinion of the International Searching Authority, dated Jun. 24, 2020, 17 pages.
C0019138.W001 (PCT/US2019/064653) PCT Invitation to Pay Additional Fees, dated Mar. 4, 2020, 16 pages.
(PCT/US2021/015632) PCT International Preliminary Report on Patentability, dated Jul. 28, 2022, 7 pages.

* cited by examiner

METHOD AND APPARATUS FOR ADJUSTING CONTROL PARAMETERS FOR CARDIAC EVENT SENSING

REFERENCE TO RELATED APPLICATION

This application claims the benefit of U.S. Patent Application No. 62/967,917, filed provisionally on Jan. 30, 2020, incorporated herein by reference in its entirety.

TECHNICAL FIELD

This disclosure relates to a medical device and method for adjusting control parameters for sensing cardiac events from a motion sensor signal.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both of the right and left ventricles.

Intracardiac pacemakers have been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, some patients may benefit from atrial and ventricular (dual chamber) sensing for providing atrial-synchronized ventricular pacing in order to maintain a regular heart rhythm.

SUMMARY

The techniques of this disclosure generally relate to a pacemaker having a motion sensor producing a motion signal, which may include signals representative of ventricular and atrial mechanical events. The pacemaker is configured to sense atrial events, e.g., atrial mechanical event signals corresponding to atrial contractions that occur during atrial systole, from the motion signal. The sensed atrial events may be used for controlling atrial synchronized ventricular pacing pulses delivered by the pacemaker in some examples. A pacemaker operating according to the techniques disclosed herein adjusts sensing control parameters used for sensing atrial event signals from the motion sensor signal. The sensing control parameters may include one or more of sensing window start times, sensing window end times, and/or sensing threshold amplitudes applied to the motion sensor signal for sensing the atrial events.

In one example, the disclosure provides a medical device including a motion sensor and a control circuit. The motion sensor is configured to produce a motion signal. The control circuit is configured to set sensing control parameters and sense atrial events from the motion signal during multiple ventricular cycles according to the sensing control parameters. The control circuit is configured to determine a feature of the motion signal for each ventricular cycle of at least a portion of the multiple ventricular cycles, determine a metric of the motion signal based on the determined features, and adjust at least one of the sensing control parameters based on the metric. The control circuit is configured to sense an atrial event from the motion signal according to the adjusted sensing control parameter and generate an atrial sensed event signal in response to sensing the atrial event.

In another example, the disclosure provides a method including producing a motion signal by a motion sensor, setting multiple sensing control parameters and sensing atrial events from the motion signal during multiple ventricular cycles according to the sensing control parameters. The method may include determining a feature of the motion signal for each ventricular cycle of at least a portion of the multiple ventricular cycles, determining a metric of the motion signal based on the determined features, adjusting at least one of the sensing control parameters based on the metric and sensing an atrial event from the motion signal according to the adjusted sensing control parameter. The method may include generating an atrial sensed event signal in response to sensing the atrial event according to the adjusted sensing control parameter.

In another example, the disclosure provides a non-transitory, computer-readable storage medium comprising a set of instructions which, when executed by a control circuit of a medical device, cause the medical device to produce a motion signal by a motion sensor, set multiple sensing control parameters, sense atrial events from the motion signal during multiple ventricular cycles according to the sensing control parameters. The instructions further cause the device to determine a feature of the motion signal for each ventricular cycle of at least some of the multiple ventricular cycles, determine a metric of the motion signal based on the determined features, adjust at least one of the sensing control parameters based on the metric, and sense an atrial event from the motion signal according to the adjusted sensing control parameter. The instructions may cause the device to generate an atrial sensed event signal in response to sensing the atrial event according to the adjusted sensing control parameter.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes techniques for adjusting cardiac event sensing parameters by an implantable medical device. As described below, a motion sensor signal, such as an accelerometer signal, may include cardiac event signals attendant to the mechanical contraction and relaxation (and filling) of a heart chamber. Cardiac event signals may be sensed from a signal produced by the motion sensor. The motion sensor signal may include cardiac event signals corresponding to ventricular events and atrial events. For example, an atrial systolic event signal corresponding to atrial mechanical contraction and the active filling phase of the ventricle, sometimes referred to as the "atrial kick" may be present in a motion sensor signal implanted in a ventricular chamber. The atrial event may be sensed from the motion sensor signal using atrial event sensing control parameters, which may include one or more sensing threshold amplitudes and/or time windows. The atrial event may be sensed according to sensing control parameters from among other cardiac event signals that may occur in the motion sensor signal during a cardiac cycle. The techniques disclosed herein provide techniques for sensing cardiac events, e.g., atrial events, from a motion sensor signal and adjusting the cardiac event sensing control parameters to improve cardiac event sensing performance by a medical device.

In some examples, the medical device is a ventricular pacemaker, which may be wholly implantable within a ventricular heart chamber, having a motion sensor for producing an intraventricular motion signal. Atrial systolic events can be sensed from within the ventricle from the motion sensor signal for use in controlling atrial synchronized ventricular pacing, for example. Atrial-synchronized ventricular pacing pulses can be delivered by a pacemaker implanted in the ventricle without requiring a sensor in or on the atria of the patient's heart for sensing atrial events.

Figure 1:
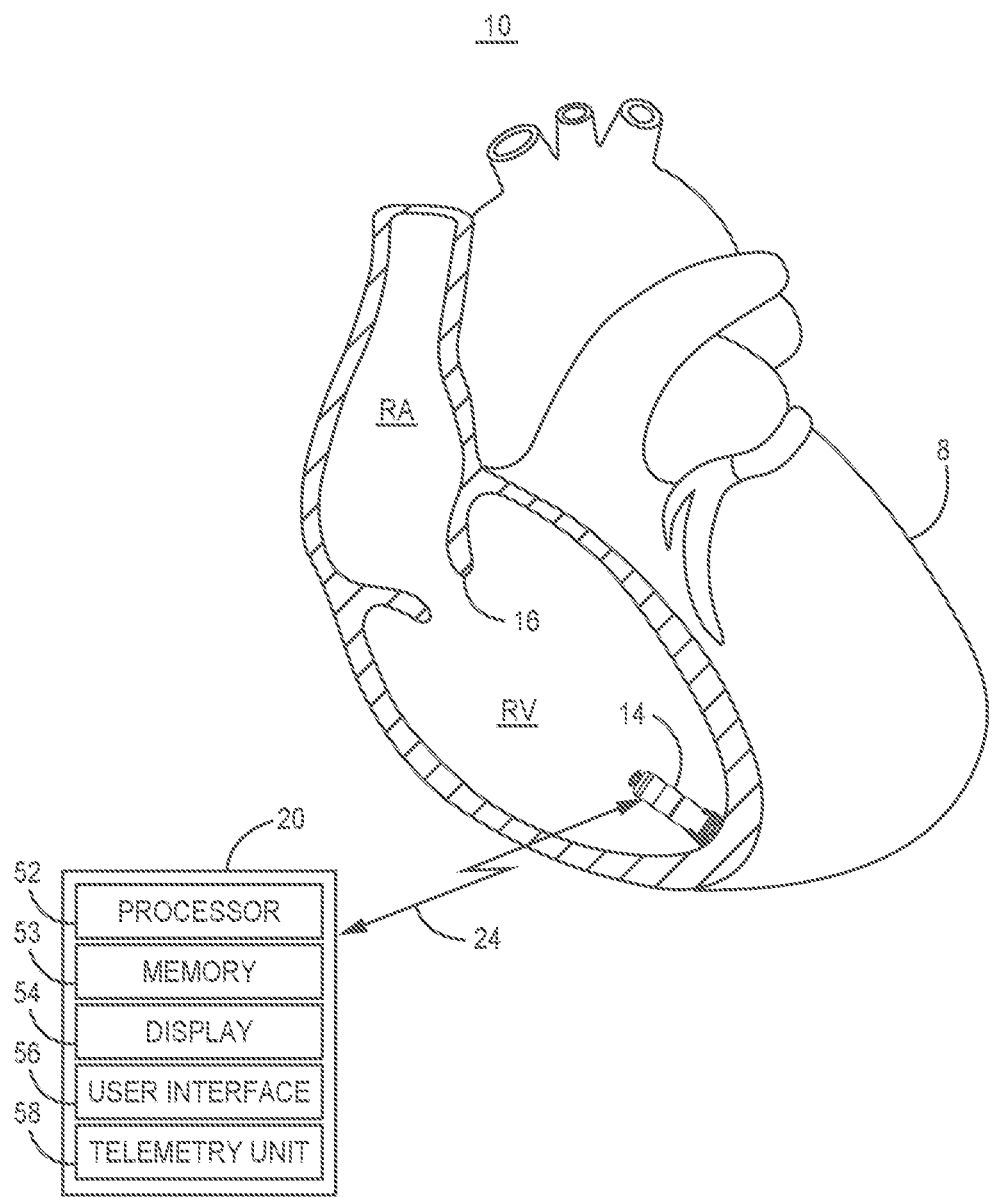
FIG. 1 is a conceptual diagram illustrating a medical device system that may be used to sense cardiac electrical signals and motion signals induced by cardiac motion and flowing blood and provide pacing therapy to a patient's heart.

FIG. 1 is a conceptual diagram illustrating an implantable medical device (IMD) system 10 that may be used to sense cardiac electrical signals and cardiac mechanical signals induced by cardiac motion and flowing blood and provide pacing therapy to a patient's heart 8. IMD system 10 includes a ventricular intracardiac pacemaker 14. Pacemaker 14 may be a transcatheter intracardiac pacemaker which is adapted for implantation wholly within a heart chamber, e.g., wholly within the right ventricle (RV) or wholly within the left ventricle (LV) of heart 8 for sensing cardiac signals and delivering ventricular pacing pulses. Pacemaker 14 may be reduced in size compared to subcutaneously implanted pacemakers and may be generally cylindrical in shape to enable transvenous implantation via a delivery catheter.

Pacemaker 14 is shown positioned in the RV, along an endocardial wall, e.g., near the RV apex though other locations are possible. The techniques disclosed herein are not limited to the pacemaker location shown in the example of FIG. 1 and other positions within heart 8 are possible. For example, ventricular intracardiac pacemaker 14 may be positioned in the LV and configured to detect cardiac motion signals and deliver atrial-synchronized ventricular pacing to the LV using the techniques disclosed herein. Pacemaker 14 may be positioned within the RV or LV to provide respective right ventricular or left ventricular pacing and for sensing cardiac mechanical event signals from a signal produced by a motion sensor within the ventricular chamber. In other examples, pacemaker 14 is not necessarily required to be implanted inside a heart chamber and may be positioned outside the heart, e.g., along the RV or LV in an epicardial location.

Pacemaker 14 is capable of producing electrical stimulation pulses, e.g., pacing pulses, delivered to heart 8 via one or more electrodes on the outer housing of the pacemaker. Pacemaker 14 is configured to deliver RV pacing pulses and sense an RV cardiac electrical signal using housing based electrodes for producing an RV electrogram (EGM) signal. The cardiac electrical signals may be sensed using the housing based electrodes that are also used to deliver pacing pulses to the RV in some examples.

Pacemaker 14 is configured to control the delivery of ventricular pacing pulses to the RV in a manner that promotes synchrony between atrial activation and ventricular activation, e.g., by maintaining a target atrioventricular (AV) interval between atrial events and ventricular pacing pulses. That is, pacemaker 14 controls pacing pulse delivery to maintain a desired AV interval between atrial contractions corresponding to atrial systole and ventricular pacing pulses delivered to cause ventricular depolarization and ventricular systolic contractions.

According to the techniques described herein, atrial systolic events producing the active ventricular filling phase are detected by pacemaker 14 from a motion sensor signal such as an accelerometer signal, generated by a motion sensor that may be enclosed by the housing of pacemaker 14. The motion signal produced by an accelerometer implanted within a ventricular chamber, which may be referred to as an "intraventricular motion signal," includes motion signals caused by ventricular and atrial events. For example, acceleration of blood flowing into the RV through the tricuspid valve 16 between the RA and RV caused by atrial systole, and referred to as the "atrial kick," may be detected by pacemaker 14 from the signal produced by an accelerometer included in pacemaker 14. Other motion signals that may be detected by pacemaker 14, such as motion caused by ventricular contraction and passive ventricular filling are described below in conjunction with FIG. 4.

Atrial P-waves that are attendant to atrial depolarization are relatively low amplitude signals in the near-field ventricular cardiac electrical signal received by pacemaker 14 (e.g., compared to the near-field R-wave attendant to ventricular depolarization) and therefore can be difficult to reliably detect from the cardiac electrical signal acquired by pacemaker 14 when implanted in a ventricular chamber. Atrial-synchronized ventricular pacing by pacemaker 14 or other functions that rely on atrial sensing may not be reliable when based solely on a cardiac electrical signal received by pacemaker 14. According to the techniques disclosed herein, pacemaker 14 includes a motion sensor, such as an accelerometer, and is configured to detect an atrial event corresponding to atrial mechanical activation or atrial systole from a signal produced by the motion sensor. Ventricular pacing pulses may be synchronized to the atrial event that is detected from the motion sensor signal by setting a programmable AV pacing interval that controls the timing of the ventricular pacing pulse relative to the detected atrial systolic event. As described below, detection of the atrial systolic event used to synchronize ventricular pacing pulses to atrial systole may include detection of other cardiac event motion signals in order to positively identify the atrial systolic event and/or adjust atrial systolic event sensing control parameters.

A target AV interval may be a default value or a programmed value selected by a clinician and is the time interval from the detection of the atrial event until delivery of the immediately subsequent ventricular pacing pulse. In some instances, the target AV interval may be started from the time the atrial systolic event is detected based on a motion sensor signal or starting from an identified fiducial point of the atrial event signal. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by pacemaker 14 and the motion sensor signal received by pacemaker 14. The AV interval may be programmed to 10 to 50 ms, as examples.

Pacemaker 14 may be capable of bidirectional wireless communication with an external device 20 for programming the AV pacing interval and other pacing control parameters as well as cardiac event sensing parameters, which may be utilized for detecting ventricular mechanical events and the atrial systolic event from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 by a user interacting with external device 20.

External device 20 may include a processor 52, memory 53, display unit 54, user interface 56 and telemetry unit 58. Processor 52 controls external device operations and processes data and signals received from pacemaker 14. Display unit 54 may generate a display, which may include a graphical user interface, of data and information relating to pacemaker functions to a user for reviewing pacemaker operation and programmed parameters as well as cardiac electrical signals, cardiac motion signals or other physiological data that may be acquired by pacemaker 14 and transmitted to external device 20 during an interrogation session.

User interface 56 may include a mouse, touch screen, keypad or the like to enable a user to interact with external device 20 to initiate a telemetry session with pacemaker 14 for retrieving data from and/or transmitting data to pacemaker 14, including programmable parameters for controlling cardiac event sensing and therapy delivery. Telemetry unit 58 includes a transceiver and antenna configured for bidirectional communication with a telemetry circuit included in pacemaker 14 and is configured to operate in conjunction with processor 52 for sending and receiving data relating to pacemaker functions via communication link 24.

At the time of implant, during patient follow-up visits, or any time after pacemaker implantation, pacemaker 14 may perform a set-up procedure to establish parameters used in detecting atrial events from the motion sensor signal. The patient may be standing, sitting, lying down or ambulatory during the process. The set-up procedure may include acquiring motion sensor signal data and generating distributions of motion sensor signal features for establishing atrial event sensing parameters. Motion sensor signal data may be transmitted to external device 20 and displayed on display unit 54 of external device 20 in the form of a histogram in some examples. The atrial event sensing parameters established based on the motion sensor signal data may be set automatically or may be transmitted to external device 20 for generating a display on display unit 54 as recommended parameters, allowing a clinician to review and accept or modify the recommended parameters, e.g., using user interface 56.

In some examples, external device processor 52 may execute operations for establishing a starting value of an atrial event sensing parameter based on data retrieved from pacemaker 14. Processor 52 may cause display unit 54 to generate a display of data relating to a motion sensor signal, including histogram distributions of metrics determined from a cardiac motion signal for use in selecting starting values of atrial event sensing control parameters. Display unit 54 may be a graphical user interface that enables a user to interact with the display, e.g., for selecting various displays or information for viewing. In some examples, a user may select one or more atrial event sensing control parameter settings to be automatically established by pacemaker 14 and/or may program starting sensing control parameters or other programmable parameters for controlling sensor operation and therapy delivery. In some examples, processing circuitry included in pacemaker 14 and/or processor 52 may determine starting values for one or more atrial systolic event sensing control parameters based on data acquired from acceleration signals produced by an accelerometer included in pacemaker 14 and various thresholds and criteria, which may include user programmable thresholds or criteria used in setting the starting parameter values.

The starting value(s) of one or sensing control parameters may be adjusted by pacemaker 14 according to the techniques disclosed herein. After establishing a starting value of a sensing control parameter used in sensing cardiac event signals from a cardiac motion signal, signal variability due to various factors such as patient posture, patient physical activity, patient heart rate, etc. may cause the starting value of a sensing control parameter to no longer be optimal. In order to promote reliable cardiac mechanical event sensing from the motion signal over time, pacemaker 14 is configured to adjust sensing control parameters. This automatic adjustment adapts and optimizes the sensing control parameters as patient or signal sensing conditions change over time, improving reliability of sensing of cardiac mechanical events and delivery of pacing therapy, even in an ambulatory patient, and reduces the burden on a clinician in manually adjusting sensing control parameters.

External device telemetry unit 58 is configured for bidirectional communication with implantable telemetry circuitry included in pacemaker 14. Telemetry unit 58 establishes a wireless communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry algorithm and circuitry that does not require the use of a programming head and does not require user intervention to maintain a communication link.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to review EGM, motion sensor signal, and marker channel data and authorize programming of sensing and therapy control parameters in pacemaker 14, e.g., after viewing a visual representation of EGM, motion sensor signal and marker channel data.

Figure 2:
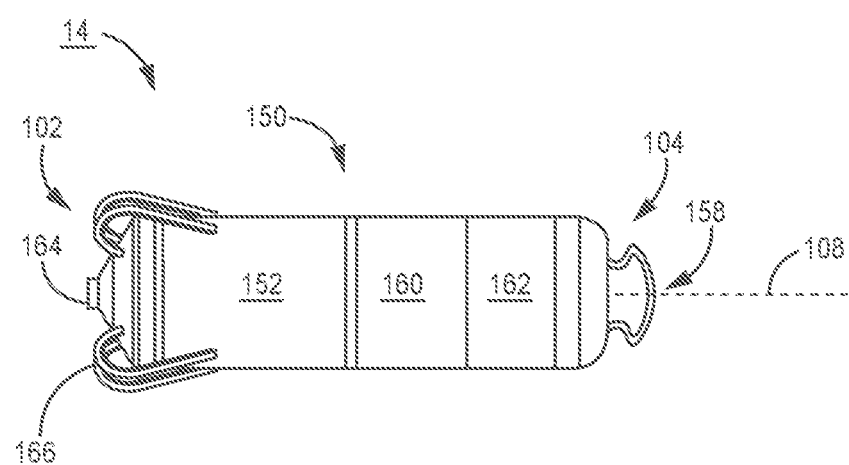
FIG. 2 is a conceptual diagram of the intracardiac pacemaker shown in FIG. 1.

FIG. 2 is a diagram of the intracardiac pacemaker 14 shown in FIG. 1 according to one example. Pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black, among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide, among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 may include a control electronics subassembly 152 and a battery subassembly 160, which provides power to the control electronics subassembly 152. Control electronics subassembly 152 houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting atrial systolic events, e.g., for use in controlling the timing ventricular pacing pulses, as described below.

The accelerometer may be a three-dimensional accelerometer. In some examples, the accelerometer may have one "longitudinal" axis that is parallel to or aligned with the longitudinal axis 108 of pacemaker 14 and two orthogonal axes that extend in radial directions relative to the longitudinal axis 108. Practice of the techniques disclosed herein, however, are not limited to a particular orientation of the accelerometer within or along housing 150. In other examples, a one-dimensional accelerometer may be used to obtain an intracardiac motion signal from which cardiac mechanical events are detected. In still other examples, a two dimensional accelerometer or other multi-dimensional accelerometer may be used. Each axis of a single or multi-dimensional accelerometer may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally with each sensor element axis orthogonal relative to the other sensor element axes. Orthogonal arrangement of the elements of a multi-axis accelerometer, however, is not necessarily required.

Each sensor element or axis may produce an acceleration signal corresponding to a vector aligned with the axis of the sensor element. A vector signal of a multi-dimensional accelerometer (also referred to as a "multi-axis" accelerometer) for use in sensing cardiac mechanical events may be selected to include a single axis signal or a combination of two or more axis signals. For example, one, two or all three axis signals produced by a three dimensional accelerometer may be selected as a vector signal for use in detecting atrial systolic events, e.g., for controlling atrial-synchronized ventricular pacing delivered by pacemaker 14. When two or more axis signals are selected, the axis signals may be summed or combined in another manner for producing a motion signal from which atrial systolic events may be sensed.

Pacemaker 14 may include features for facilitating deployment and fixation of pacemaker 14 at an implant site. For example, pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 3:
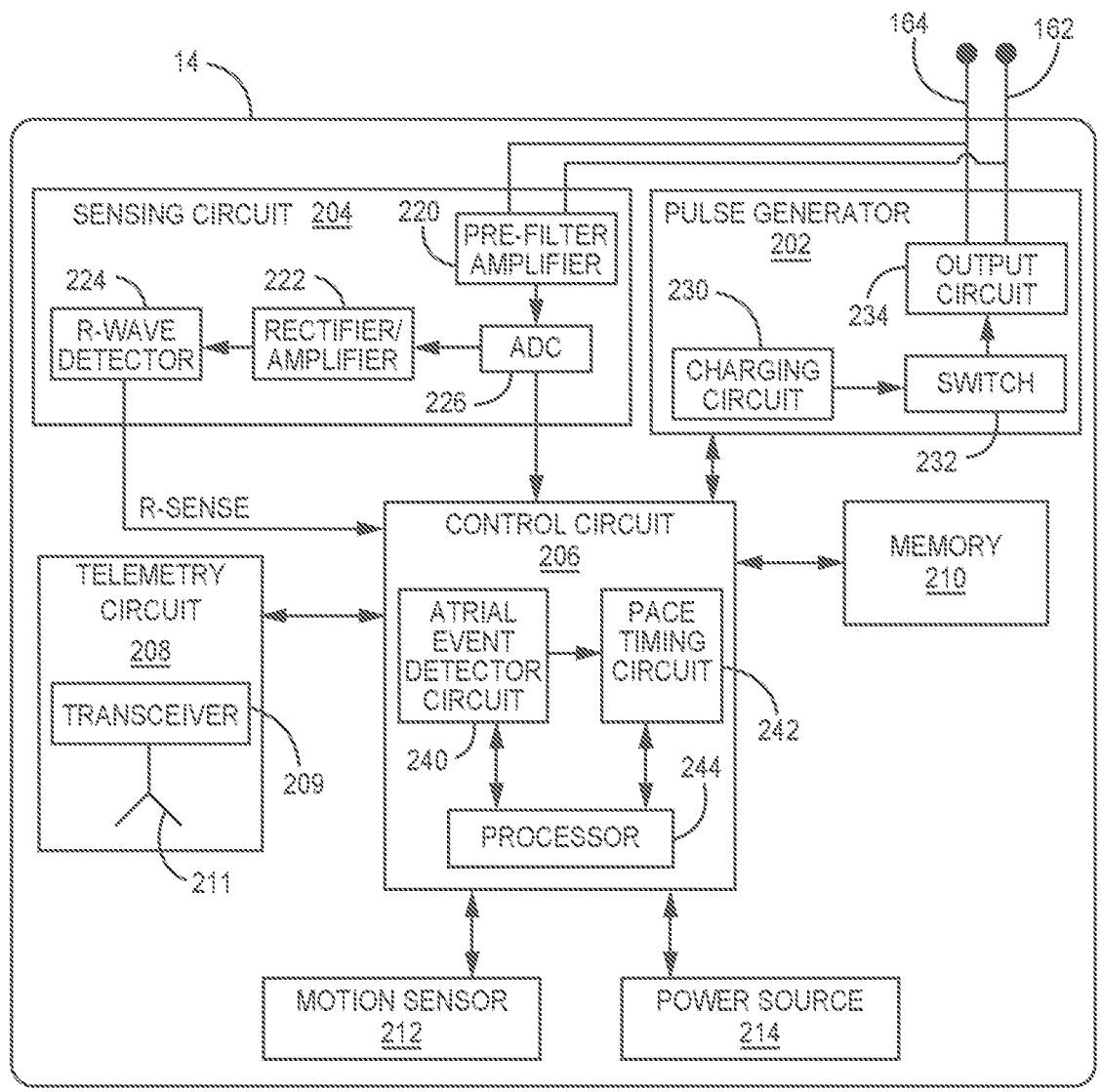
FIG. 3 is a schematic diagram of an example configuration of the pacemaker shown in FIG. 1.

FIG. 3 is a conceptual diagram of an example configuration of pacemaker 14 shown in FIG. 1. Pacemaker 14 includes a pulse generator 202, a cardiac electrical signal sensing circuit 204, a control circuit 206, memory 210, telemetry circuit 208, motion sensor 212 and a power source 214. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Motion sensor 212 may include an accelerometer in the examples described herein. Motion sensor 212 is not limited to being an accelerometer, however, and other motion sensors may be utilized successfully in pacemaker 14 for detecting cardiac motion signals according to the techniques described herein. Examples of motion sensors that may be implemented in motion sensor 212 include piezoelectric sensors and MEMS devices.

Motion sensor 212 may include a multi-axis sensor, e.g., a two-dimensional or three-dimensional sensor, with each axis providing an axis signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. The motion sensor 212 may include one or more filter, amplifier, rectifier, analog-to-digital converter (ADC) and/or other components for producing a motion signal that is passed to control circuit 206. For example, each signal produced by each individual axis of a multi-axis accelerometer may be filtered by a high pass filter, e.g., a 10 Hz high pass filter. The filtered signal may be digitized by an ADC and rectified for use by atrial event detector circuit 240 for detecting atrial systolic events. The high pass filter may be lowered (e.g., to 5 Hz) if needed to detect atrial signals that have lower frequency content. In some examples, high pass filtering is performed with no low pass filtering. In other examples, each accelerometer axis signal is filtered by a low pass filter, e.g., a 30 Hz low pass filter, with or without high pass filtering.

One example of an accelerometer for use in implantable medical devices that may be implemented in conjunction with the techniques disclosed herein is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events.

Sensing circuit 204 is configured to receive a cardiac electrical signal via electrodes 162 and 164 by a pre-filter and amplifier circuit 220. Pre-filter and amplifier circuit 220 may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for establishing atrial sensing control parameters and for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave sensing threshold, which may be an auto-adjusting threshold. When the incoming signal crosses the R-wave sensing threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. Processor 244 may provide sensing control signals to sensing circuit 204, e.g., R-wave sensing threshold, sensitivity, and various blanking and refractory intervals applied to the cardiac electrical signal for controlling R-wave sensing. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 includes an atrial event detector circuit 240, pace timing circuit 242, and processor 244. Control circuit 206 may receive R-wave sensed event signals and/or digital cardiac electrical signals from sensing circuit 204 for use in detecting and confirming cardiac events associated with each heartbeat (e.g., intrinsic ventricular depolarizations) and controlling ventricular pacing. For example, R-wave sensed event signals, which may correspond to intrinsic ventricular depolarizations, may be passed to pace timing circuit 242 for inhibiting scheduled ventricular pacing pulses or for scheduling ventricular pacing pulses when pacemaker 14 is operating in a non-atrial tracking ventricular pacing mode. R-wave sensed event signals may also be passed to atrial event detector circuit 240 for use in setting time windows used by control circuit 206 in detecting atrial systolic events from the motion sensor signal.

Atrial event detector circuit 240 is configured to detect atrial systolic events from a signal received from motion sensor 212. Techniques for setting time windows used in detecting atrial systolic events are described below. In some examples, one or more ventricular mechanical events may be detected from the motion sensor signal in a given cardiac cycle to facilitate positive detection of the atrial systolic event from the motion sensor signal during the ventricular cycle and for adjusting atrial systolic event sensing control parameters.

Atrial event detector circuit 240 receives a motion signal from motion sensor 212 and may start an atrial "blanking" period in response to a ventricular electrical event, e.g., an R-wave sensed event signal from sensing circuit 204 or delivery of a pacing pulse by pulse generator 202. The blanking period may correspond to a time period after the ventricular electrical event during which ventricular mechanical events, e.g., corresponding to ventricular contraction or opening and/or closing of semilunar valves, are expected to occur. When ventricular pacing is properly synchronized to atrial events, an atrial event is not expected to occur during the atrial blanking period, corresponding to ventricular systole. The motion signal peaks that occur during the atrial blanking period, therefore, are not sensed as atrial events. The atrial "blanking" period may be used to define a time period following a ventricular electrical event during which an atrial systolic event is not sensed by atrial event detector circuit 240. The motion sensor signal, however, is not necessarily blanked during this time period in that control circuit 206 may still receive the motion sensor signal during the atrial blanking period and may process the motion signal for sensing ventricular events during the atrial blanking period in some examples.

For instance, the motion sensor signal during the blanking period may be monitored by atrial event detector circuit 240 for the purposes of detecting ventricular mechanical events, which may be used for confirming or validating atrial systolic event detection in some examples. As such, ventricular mechanical event detection windows may be set during the atrial blanking period and may be set according to predetermined time intervals following identification of a ventricular electrical event. Atrial event detector circuit 240 may be configured to detect one or more ventricular mechanical events during respective ventricular event detection windows during the atrial blanking period. The timing and detection of the ventricular mechanical events may be used to update the atrial blanking period and/or may be used to confirm detection of the atrial event occurring subsequent to expected ventricular mechanical events.

Atrial event detector circuit 240 determines if the motion sensor signal satisfies atrial systolic event detection criteria outside of the atrial blanking period. In some examples, atrial event detector circuit 240 may set an atrial refractory period starting upon a ventricular electrical event, sensed or paced. Atrial event detector circuit 240 may set time windows corresponding to the passive ventricular filling phase and the active ventricular filling phase (atrial systole) based on the timing of a preceding ventricular electrical event, either an R-wave sensed event signal or a ventricular pacing pulse. A motion sensor signal crossing of an atrial event sensing threshold during either of these windows and outside the atrial blanking period, may be detected as the atrial systolic event. As described below, two different atrial event sensing threshold values may be established for applying during the passive filling phase window and after the passive filling phase window (during an active filling phase window also referred to below as an "A4 window").

Atrial event detector circuit 240 may pass an atrial event detection signal to processor 244 and/or pace timing circuit 242 in response to detecting an atrial event. Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. In some examples, an atrial event sensed outside the atrial blanking period but within the atrial refractory period is classified as an atrial refractory sense. An atrial refractory sense may not cause pace timing circuit to start an AV pacing interval so that atrial refractory sensed events are not tracked by ventricular pacing pulses. Atrial refractory sensed events may be used in some instances, however, e.g., for adjusting atrial event sensing control parameters or for determining an atrial rate.

Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242. One application of atrial sensed event signals produced by atrial event detector circuit 240 is for setting AV pacing intervals for controlling the timing of ventricular pacing pulses. Control circuit 206, however, may use atrial sensed event signals for other purposes.

Pace timing circuit 242 may additionally include a lower pacing rate interval timer for controlling a minimum ventricular pacing rate. For example, if an atrial systolic event is not detected from the motion sensor signal triggering a ventricular pacing pulse at the programmed AV pacing interval, a ventricular pacing pulse may be delivered by pulse generator 202 upon expiration of the lower pacing rate interval to prevent ventricular asystole and maintain a minimum ventricular rate. At times, control circuit 206 may control pulse generator 202 in a non-atrial tracking ventricular pacing mode (which may also be referred to as "asynchronous ventricular pacing") during a process for establishing sensing parameters used for detecting atrial systolic events from the motion signal. The non-atrial tracking ventricular pacing mode may be denoted as a VDI pacing mode in which ventricular pacing pulses are delivered in the absence of a sensed R-wave and inhibited in response to an R-wave sensed event signal from sensing circuit 204. Dual chamber sensing may be performed during the non-atrial tracking ventricular pacing mode by sensing ventricular electrical events by sensing circuit 204 and sensing atrial systolic events from the motion signal received by atrial event detector circuit 240 from motion sensor 212. Atrial event sensing parameters established during a VDI pacing mode may include the end time of a passive ventricular filling window, the atrial event sensing threshold amplitude values applied during and after the passive ventricular filling window, and the post-ventricular atrial refractory period, as examples. These atrial event sensing parameters established during a VDI pacing mode may be applied during a VDD pacing mode in which the ventricular pacing pulses track sensed atrial events at the AV interval.

Pulse generator 202 generates electrical pacing pulses that are delivered to the RV of the patient's heart via cathode electrode 164 and return anode electrode 162. In addition to providing control signals to pace timing circuit 242 and pulse generator 202 for controlling the timing of ventricular pacing pulses, processor 244 may retrieve programmable pacing control parameters, such as pacing pulse amplitude and pacing pulse width, which are passed to pulse generator 202 for controlling pacing pulse delivery. Pulse generator 202 may include charging circuit 230, switching circuit 232 and an output circuit 234.

Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or VV lower rate pacing interval) and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the delivery of pacing pulses by pulse generator 202, e.g., by detecting an atrial event by atrial event detector circuit 240 from the motion sensor signal according to the techniques disclosed herein and setting a pacing escape interval timer included in pace timing circuit 242. Memory 210 may include various buffers for storing threshold crossing times and/or amplitudes of the motion sensor signal for use in adjusting atrial event sensing control parameters as described below.

Power source 214 provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example, power source 214 may provide power as needed to charging and switching circuitry included in pulse generator 202, amplifiers, ADC 226 and other components of sensing circuit 204, telemetry circuit 208, memory 210, and motion sensor 212.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212. Providing software, hardware, and/or firmware to accomplish the described functionality in the context of any modern pacemaker, given the disclosure herein, is within the abilities of one of skill in the art.

Figure 4:
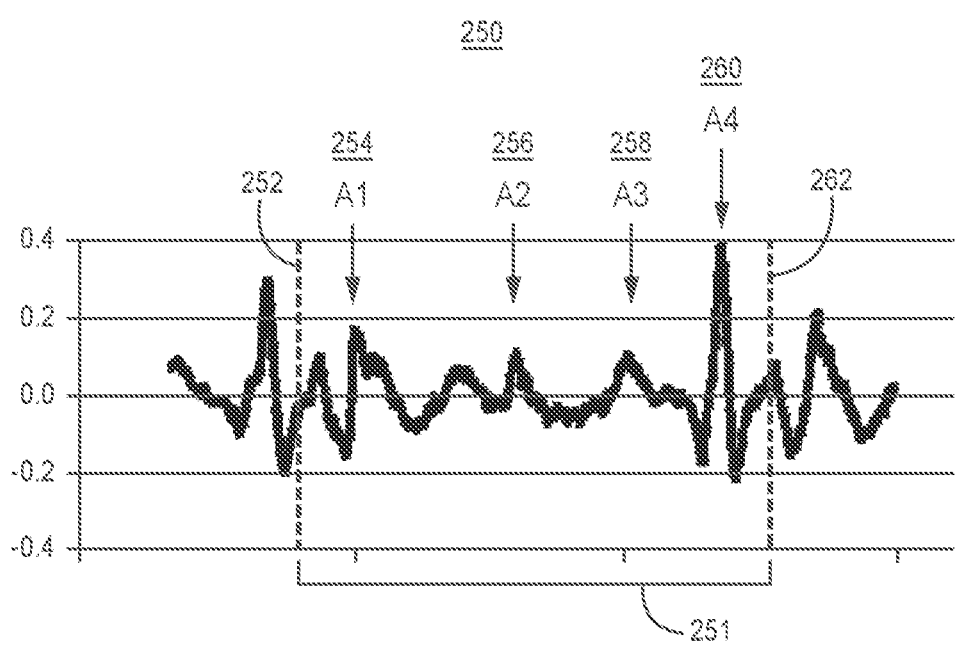
FIG. 4 is an example of a motion sensor signal that may be produced by a motion sensor over a cardiac cycle.

FIG. 4 is an example of a motion sensor signal 250 that may be acquired by motion sensor 212 over a cardiac cycle. Vertical dashed lines 252 and 262 denote the timing of two consecutive ventricular electrical events (an intrinsic ventricular depolarization or a ventricular pacing pulse), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 212 is implemented as an accelerometer) that occurs during ventricular contraction and marks the approximate onset of ventricular mechanical systole. The A1 event is also referred to herein as a "ventricular contraction event." The A2 event 256 is an acceleration signal that may occur with closure of the aortic and pulmonic valves, marking the approximate offset or end of ventricular mechanical systole. The A2 event may also mark the isovolumic relaxation phase of the ventricles that occurs with aortic and pulmonic valve closure.

The A3 event 258 is an acceleration signal that occurs during passive ventricular filling and marks ventricular mechanical diastole. The A3 event is also referred to herein as and as a "ventricular diastolic event." Since the A2 event occurs with the end of ventricular systole, it may be an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is also referred to herein as the "atrial event" that is detected from motion sensor signal 250. Atrial event detector circuit 240 detects A4 event 260 using atrial event sensing control parameters as disclosed herein. Processor 244 may control pace timing circuit 242 to trigger a ventricular pacing pulse by starting an AV pacing interval in response to detecting the A4 event 260, e.g., when it occurs outside a post-ventricular atrial blanking period and after a post-ventricular atrial refractory period. Control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses in some examples.

Techniques described below in conjunction with flow charts and diagrams presented herein may be performed by pacemaker 14 for adjusting sensing control parameters used for sensing A4 events, without necessarily requiring identification and discrimination of the A1-A4 events. The motion signal may be characterized by determining features of the motion signal during and after a passive ventricular filling window, outside an atrial blanking period. These features are used in establishing atrial event sensing parameters by control circuit 206.

Figure 5:
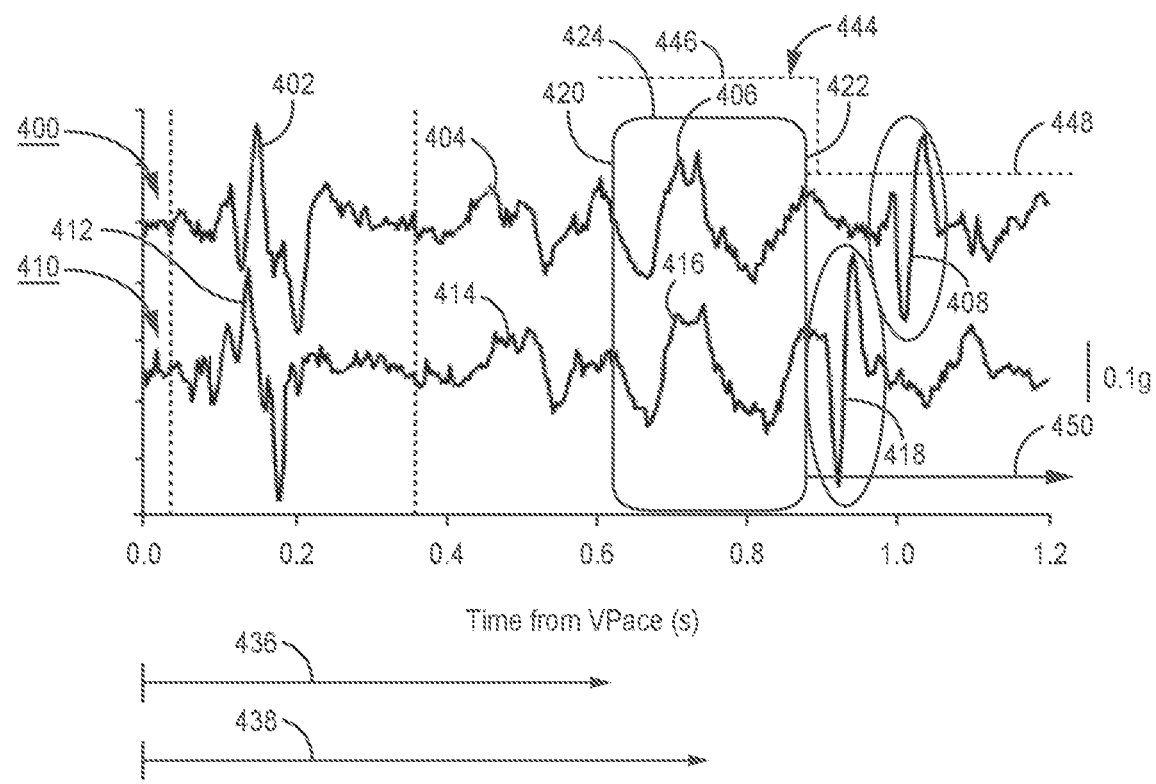
FIG. 5 is an example of motion sensor signals produced over two different cardiac cycles.

FIG. 5 is an example of motion sensor signals 400 and 410 acquired over two different cardiac cycles. A ventricular pacing pulse is delivered at time 0.0 seconds for both cardiac cycles. The top motion sensor signal 400 is received over one cardiac cycle, and the bottom motion sensor signal 410 is received over a different cardiac cycle. The two signals 400 and 410 are aligned in time at 0.0 seconds, the time of the ventricular pacing pulse delivery. While motion signals 400 and 410 and motion signal 250 of FIG. 4 are shown as raw accelerometer signals, it is recognized that control circuit 206 may receive a digitized filtered, amplified and rectified signal from motion sensor 212 for processing and analysis as described in conjunction with the accompanying drawings.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (which may mark the end of ventricular systole and the isovolumic ventricular relaxation phase) and the A3 events 406 and 416 (occurring during passive ventricular filling) are well-aligned in time. Since the A1, A2 and A3 events are ventricular events, occurring during ventricular contraction, at the end of ventricular systole and during passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave, however, during a stable paced or intrinsic ventricular rhythm, the relative timing of ventricular A1, A2 and A3 events to each other and the immediately preceding ventricular electrical event is expected to be consistent from beat-to-beat.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining an atrial blanking period 436 and increasing confidence in reliably detecting A4 events 408 and 418. The atrial systolic event is not detected during the atrial blanking period 436 which may extend from the ventricular electrical event (at time 0.0) through an estimated onset of ventricular diastole so that the atrial blanking period 436 includes both the A1 and A2 events in some examples. An A3 window 424 may be set having a starting time 420 corresponding to the end of the post-ventricular atrial blanking period 436 and having an ending time 422. The ending time 422 may be adjusted using techniques described herein, e.g., below in conjunction with FIGS. 12-14. The ending time 422 may also be considered a starting time of an A4 sensing window 450, though A4 events may be sensed during the A3 window in some instances. The A3 window 424 is also referred to here as a "ventricular diastolic event window," and ending time 422 is also referred to herein as a "ventricular diastolic event window ending time" since the A3 event corresponding to passive ventricular filling, a ventricular diastolic event, is expected to occur during the A3 window, before ending time 422.ear A4 events 408 and 418 may be detected based on a multi-level A4 sensing threshold 444. As seen by the lower motion sensor signal 410, the A4 event 418 may occur earlier after the A3 window 424 due to changes in atrial rate. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. As such, in some examples a first, higher A4 sensing threshold amplitude 446 may be established for detecting an early A4 event that is fused with the A3 event during the A3 window 424. A second, lower A4 sensing threshold amplitude 448 may be established for detecting relatively later A4 events, after the ending time 422 of the A3 window 424, during an A4 window 450. The A4 window 450 extends from the ending time 422 of the A3 window 424 until the next ventricular electrical event, sensed or paced. The earliest crossing of the A4 sensing threshold 444 by the motion sensor signal after the starting time 420 of the A3 window (or after the expiration of the atrial blanking period 436) may be detected as the atrial systolic event. Atrial event detector circuit 240 may sense the A4 event in response to the earliest crossing time of the high A4 sensing threshold amplitude or the low A4 sensing threshold amplitude. Techniques for adjusting the high A4 sensing threshold amplitude 446 used during the A3 window 424 and the low A4 sensing threshold amplitude 448 used after the ending time 422 of the A3 window 424, during the A4 window 450, are described below in conjunction with FIGS. 7-15.

In some examples, control circuit 206 may set a post-ventricular atrial refractory period (PVARP) 438. The PVARP 438 may extend from the ventricular electrical event (sensed R-wave or ventricular pacing pulse) for a time interval longer than the post-ventricular atrial blanking period 436. Depending on the end time 422 of the A3 window 424, the PVARP 438 will generally expire during the A3 window 424. When the motion sensor signal crosses the high A4 sensing threshold amplitude 446 during the PVARP 438, but outside the blanking period 436, a refractory A4 sense may be made by atrial event detector circuit 240. Pace timing circuit 242 does not set an AV pacing interval in response to a refractory A4 sense, but control circuit 206 may use the refractory A4 sense in adjusting A4 sensing control parameters. When the motion sensor signal crosses the A4 sensing threshold 444 after the expiration of PVARP 438, atrial event detector circuit 240 senses the atrial systolic event, and pacing timing circuit 242 starts an AV pacing interval (not shown in FIG. 5). Upon expiration of the AV pacing interval, pulse generator 202 generates a pacing pulse delivered to the ventricle to track the non-refractory sensed atrial event.

Figure 6:
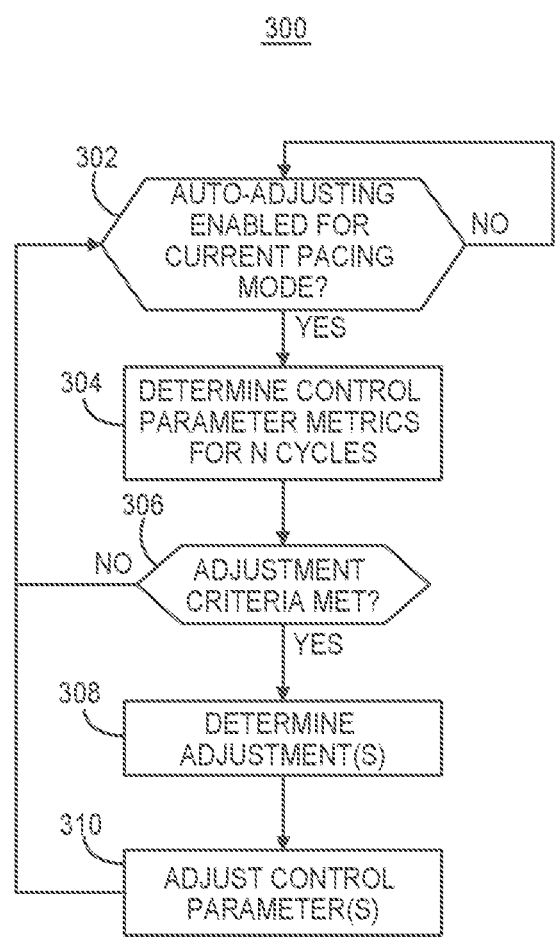
FIG. 6 is a flow chart of a method for adjusting atrial event sensing control parameters according to some examples.

FIG. 6 is a flow chart 300 of a method for adjusting atrial event sensing control parameters according to some examples. Control circuit 206 may perform the method of flow chart 300 to automatically adjust values of atrial event sensing control parameters, also referred to herein as "A4 sensing control parameters," used in sensing A4 events from the motion sensor signal. In some examples, the A4 events are sensed during an atrial tracking ventricular pacing mode, e.g., a VDD pacing mode. The VDD pacing mode may be a temporary pacing mode or a permanent pacing mode. For example, pacemaker 14 may be operating in a permanent VDD pacing mode that temporarily switches to a non-atrial tracking ventricular pacing mode, e.g., a VDI(R) or VVI(R) pacing mode. When control circuit 206 is not operating in an atrial tracking ventricular pacing mode, as determined at block 302, adjustments to one or more atrial event sensing control parameters may be disabled.

In some instances, pacemaker 14 may be operating in a temporary VDI pacing mode at block 302, e.g., upon implantation of pacemaker 14, to allow starting values of the atrial sensing control parameters to be determined and adjusted to values that are tailored to the patient. One example of an A4 sensing control parameter adjustment process is described below in conjunction with FIG. 18. Starting values of the atrial event sensing control parameters may be set according to user-programmed or default, nominal values. In other examples, starting values of the atrial event sensing control parameters may be established during an automatic set-up process performed by pacemaker 14 during which motion signal features are determined over a period of time to generate distributions and/or median values or other metrics of the signal features. Starting atrial event sensing control parameters may be established based on the generated distributions and median values. Example techniques for establishing starting values of atrial event sensing control parameters are generally disclosed in commonly assigned U.S. Patent Application Publication No. 2020/0179707 (Splett, et al.) and U.S. Patent Application Publication No. 2020/0179708 (Splett, et al.), both of which are incorporated herein by reference in their entirety. As described in conjunction with FIG. 18, the starting values of at least some A4 sensing control parameters may be adjusted during a non-atrial tracking ventricular pacing mode that includes atrial and ventricular (dual chamber) sensing, e.g., a VDI pacing mode.

When control circuit 206 is operating in a specified pacing mode at block 302 (e.g., VDI or VDD), control circuit 206 may enable and perform adjustments to one or more A4 sensing control parameters. In some examples, automatic adjustment of an A4 sensing control parameter may be enabled or disabled by a user, e.g., via a programming command transmitted by external device 20 and received by telemetry circuit 208. Adjustment of A4 sensing control parameters may be programmably enabled or disabled individually or as a group. As such in some examples, control circuit 206 may determine at block 302 that the automatic adjustment of a given A4 sensing control parameter is programmed "on" or enabled by a user and that the current pacing mode is a designated pacing mode during which A4 sensing control parameter adjustments can be performed.

At block 304, control circuit 206 determines sensing control parameter metrics from the motion signal over a predetermined number of cardiac cycles. The sensing control parameter metrics are features or characteristics of the motion sensor signal that are determined by control circuit 206 for use in setting or adjusting A4 sensing control parameters that discriminate the A4 event (which may be fused with the A3 event) from the A1, A2 and A3 events. As described in detail below, the sensing control parameter metrics may be determined based on the motion sensor signal amplitude, e.g., a maximum peak amplitude or a predetermined threshold amplitude, during a specified time window of the ventricular cycle. Control circuit 206 may adjust the A4 sensing control parameters based on the control parameter metrics determined from the motion sensor signal over a predetermined number of ventricular cycles. Some control parameter metrics are features or characteristics of the motion sensor signal that provide information about the expected timing and/or amplitude of the atrial systolic event to enable A4 sensing control parameters to be adjusted appropriately. Other control parameter metrics are features or characteristics of the motion sensor signal that provide information about the expected timing and/or amplitude of other features of the motion signal, e.g., A3 event signals, which may enable control circuit 206 to adjust A4 sensing control parameters in a manner that avoids oversensing of A3 event signals or other motion signals that are not the A4 event signal.

In the illustrative examples presented herein, the sensing control parameter metrics are determined from a predetermined number of consecutive ventricular cycles, for example 8 consecutive ventricular cycles. In other examples, sensing control parameter metrics may be determined from a predetermined number of ventricular cycles that include an A4 window. The A4 window may not be started in a given ventricular cycle when an A4 event is sensed during the A3 window or an intrinsic R-wave is sensed before the A4 window. The term "applicable cycle" is used herein to refer to ventricular cycles that include an A4 window that is started after expiration of the A3 window ending time. In some examples, the sensing control parameter metrics are determined from a predetermined number of applicable cycles, e.g., 8 applicable cycles, which may or may not be consecutive ventricular cycles.

In various examples, the determination of A4 sensing control parameter metrics over one or more ventricular cycles of the motion signal may include determining the maximum amplitude of the motion signal during the A4 window, the time of the maximum amplitude during the A4 window relative to a most recent preceding ventricular electrical event, the maximum amplitude of the motion signal during the A3 window, and a latest time of a low threshold amplitude crossing during the A3 window. Other control parameter metrics that may be determined may relate to the number or count of ventricular cycles during which an A4 event is sensed during the A4 window, the number or count of ventricular cycles during which an A4 event is sensed during the A3 window, the number or count of ventricular cycles with an A4 window (e.g., the number of cycles that are longer than the ending time of the A3 window), the number or count of ventricular cycles having an A4 event sensed early during the A4 window, the number or count of ventricular cycles having an A4 event sensed late during the A4 window or other parameters counted over a predetermined number of ventricular cycles. Example methods for determining the control parameter metrics are described below, e.g., in conjunction with FIGS. 7-8. The control parameter metrics may be determined from one or more ventricular cycles as a mean, median, a specified ordinal (nth) highest or lowest value, or a frequency or count of a specified event out of the multiple ventricular cycles.

At block 306, control circuit 206 may verify that other adjustment criteria are met before performing an A4 sensing control parameter adjustment based on the control parameter metrics determined at block 304. Various criteria may require that a sensing control parameter be within a predetermined range, e.g., less than or equal to a maximum adjustable value or greater than or equal to a minimum adjustable value, before adjusting the sensing control parameter. Other criteria may verify that an A4 event is detected for a minimum number of the predetermined number of ventricular cycles such that a given control parameter metric determined at block 304 over the predetermined number of ventricular cycles is considered a valid metric to base an adjustment on. Other criteria may require that the A4 sensing control parameter metrics determined from the motion sensor signal at block 304 indicate a change in the atrial systolic event timing and/or amplitude and/or a change in the timing and/or amplitude of the A3 event. As further described below, control circuit 206 may determine that adjustment criteria are met by comparing the A4 sensing control parameter metrics determined at block 304 to various criteria for detecting evidence of A4 event undersensing and/or evidence of oversensing of A3 events or other motion signals as false A4 events.

When adjustment criteria are unmet, as determined by control circuit 206 at block 306, A4 sensing control parameter adjustment may not be performed (or the adjustment is set to zero). Control circuit 206 returns to block 302. When adjustment criteria are met at block 306, control circuit 206 determines an adjustment value at block 308. As described below, the A4 sensing control parameter metrics determined from the motion sensor may be evaluated to determine if a given A4 sensing control parameter should be incremented or decremented from its current value. In some examples, a target value of an A4 sensing control parameter may be determined at block 308 based on the A4 sensing control parameter metrics determined at block 304 so that the A4 sensing control parameter may be appropriately incremented or decremented toward the target value or left unchanged.

At block 310, control circuit 206 adjusts the A4 sensing control parameter according to the determined adjustment. The A4 sensing control parameter may be the A3 window ending time (e.g., ending time 422 in FIG. 5), the high A4 threshold amplitude applied during the A3 window (e.g., high A4 threshold 446 in FIG. 5), the low A4 sensing threshold amplitude applied after the A3 window (e.g., low A4 threshold 448 in FIG. 5), and/or the PVARP (e.g., PVARP 438 shown in FIG. 5). Example methods performed by control circuit 206 for determining A4 sensing control parameter metrics from the motion sensor signal (at block 304), determining if adjustment criteria are met (at block 306), and determining the appropriate adjustment to be made (block 308) for adjusting each of the example A4 sensing control parameters listed above are described below in conjunction with the accompanying flow charts and diagrams.

Figure 7:
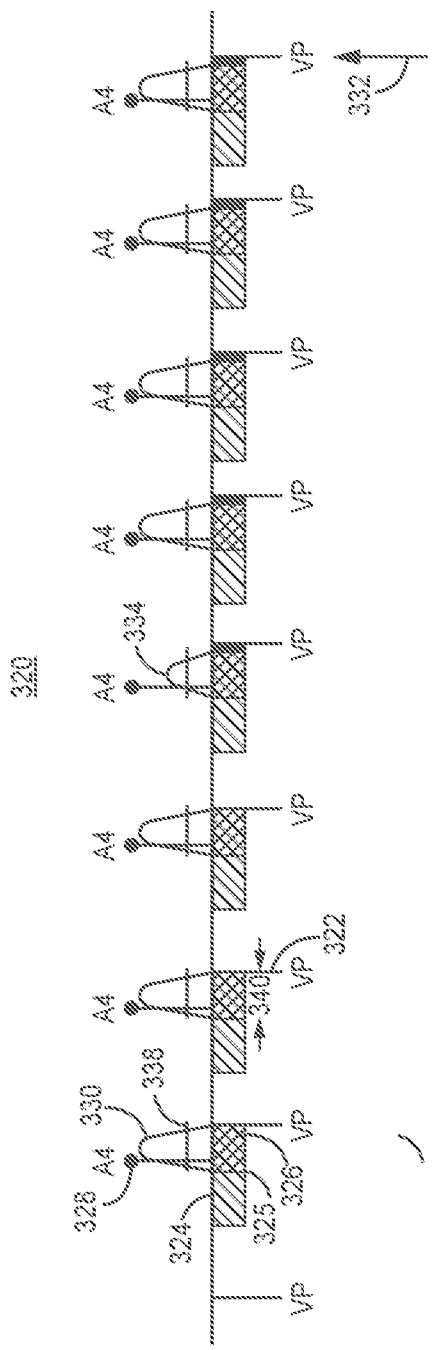
FIG. 7 is a diagram illustrating a method for determining a control parameter metric during an atrial tracking ventricular pacing mode according to one example.

FIG. 7 is a diagram 320 illustrating a method for determining an A4 sensing control parameter metric from the motion sensor signal during an atrial tracking ventricular pacing mode according to one example. In this example, eight ventricular cycles are illustrated, each starting with a ventricular pacing pulse (VP) 322, tracked to a preceding A4 sensed event signal 328 by an AV pacing interval 340. The end of the eight ventricular cycles is indicated by 332, which is the final, ending VP of the group of eight cycles. The AV pacing interval 340 is the pacing interval set by pace timing circuit 242 in response to the A4 sensed event signal 328 and extends from the A4 sensed event signal 328 to the subsequently ventricular pacing pulse 322 delivered by pulse generator 202 upon expiration of the AV pacing interval 340.

In response to each VP 322, control circuit 206 starts an A3 window 324 according to a predetermined A3 window starting time, e.g., 600 ms after the VP 322. The A4 window 326 starts upon the expiration of the A3 window 324 at an A3 window ending time 325 and extends until an A4 signal 330 is sensed or a ventricular pacing rate interval (VV interval) expires resulting in a ventricular pacing pulse when an A4 signal is not sensed. In the example of FIG. 7, an A4 event 330 is sensed in response to a crossing of the low A4 sensing threshold amplitude 338 (during the A4 window 326) during each of the eight ventricular cycles shown. An A4 sensed event signal 328 may be generated by atrial event detector circuit 240 in response to the earliest A4 sensing threshold amplitude crossing during each ventricular cycle (outside the post-ventricular blanking period). The next VP 322 is generated by pulse generator 202 upon expiration of the AV pacing interval 340 started by pace timing circuit 242 in response to the A4 sensed event signal 328.

It is noted that the durations of the A3 window 324, the A4 window 326 and the AV pacing interval 340 are shown for illustration purposes and not necessarily shown according to time scale relative to one another or the ventricular cycle lengths as a whole in the diagram 320. For example, the AV pacing interval 340 may be 10 to 30 ms (e.g., 20 ms) while the A3 window 324 may be 200 to 300 ms long, and the A4 window 326 may be even longer, e.g., 400 ms or longer in some examples. The relative durations of the A3 windows 324, A4 windows 326 and AV pacing intervals 340 are shown for the sake of illustration and convenience in FIG. 7 with no limitations intended.

Control circuit 208 may determine an A4 sensing control parameter metric every eight (or other selected number) ventricular cycles, e.g., upon the ending VP 332 of the eight ventricular cycles shown in FIG. 7. In the example shown in FIG. 7, the A4 sensing control parameter metric being determined by control circuit 206 is the minimum detected A4 amplitude. The maximum motion signal amplitude during the A4 window 326 may be determined as the A4 signal amplitude during each ventricular cycle that includes an A4 sensed event signal 328 after the A3 window ending time 326. The lowest maximum amplitude value 334 determined during the eight ventricular cycles is determined upon expiration of the eight ventricular cycles (at VP 332) as the minimum detected A4 amplitude. As described below this minimum detected A4 amplitude is a feature of the motion sensor signal determined over the specified number of ventricular cycles by control circuit 206 as an A4 sensing control parameter metric used in adjusting the low A4 sensing threshold amplitude 338.

For example, if this minimum detected A4 amplitude 334 is at least 1.5 times the low A4 sensing threshold amplitude 338, the low A4 sensing threshold amplitude 338 may be increased. An adequate safety margin between the minimum detected A4 amplitude 334 and the low A4 sensing threshold amplitude 338 exists, such that control circuit 206 may increase the low A4 sensing threshold amplitude 338. When control circuit 206 determines that the peak amplitudes of the sensed A4 events are relatively high (based on the minimum detected A4 amplitude 334) and A4 events are being regularly sensed during most ventricular cycles (e.g., at least 75% of ventricular cycles), the low A4 sensing threshold amplitude 338 may be incremented to avoid oversensing of other motion signals (which may be cardiac or body motion or other signal noise) while still providing a reasonable safety margin between the minimum detected A4 amplitude 334 and the low A4 sensing threshold amplitude 338.

Other multiples of the low A4 sensing threshold amplitude 338 may be compared to the minimum detected A4 amplitude 334 to determine if more than a minimum desired safety margin exists between the low A4 sensing threshold amplitude 338 and the minimum detected A4 amplitude, justifying an increase in the low A4 sensing threshold amplitude. In other examples, 1.25 times the low A4 sensing threshold amplitude 338 up to 2 times the low A4 sensing threshold amplitude 338 may be used as an adjustment threshold applied to the minimum detected A4 amplitude 334. When the minimum detected A4 amplitude 334 is at least the selected multiple greater than the current value of the low A4 sensing threshold amplitude 338, the low A4 sensing threshold amplitude 338 may be safely increased by control circuit 206. A relatively lower multiple, like 1.25 times the low A4 sensing threshold amplitude 338, tends to allow control circuit 206 to increment the low A4 sensing threshold amplitude 338 more often and toward higher values while maintaining a relatively lower safety margin between the low A4 sensing threshold amplitude 338 and the minimum detected A4 amplitude 334. A relatively higher multiple, like 2 times the low A4 sensing threshold amplitude 338, tends to cause control circuit 206 to increment the low A4 sensing threshold amplitude less often, holding the low A4 sensing threshold amplitude to relatively lower values over time, with a greater safety margin between the low A4 sensing threshold amplitude 338 and the minimum detected A4 amplitude 334.

Figure 8:
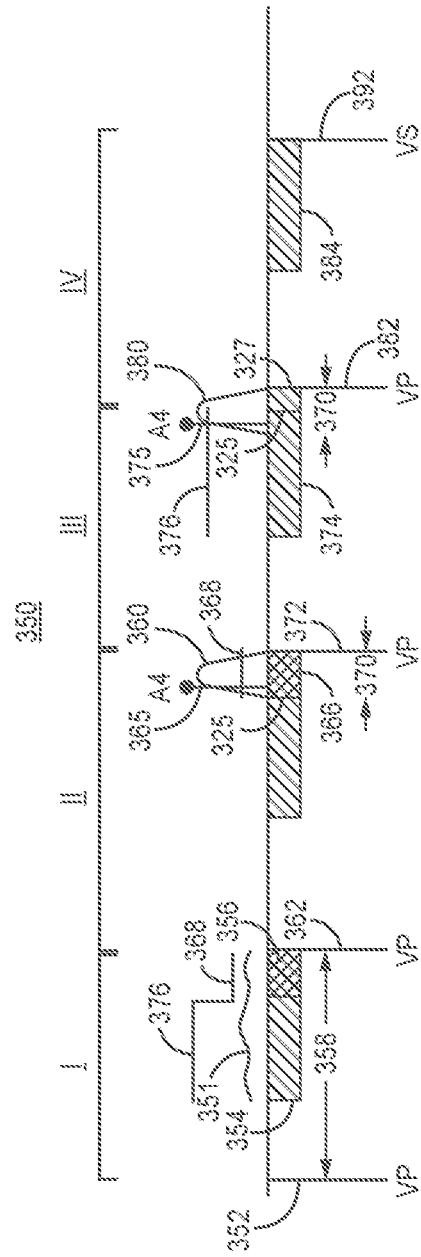
FIG. 8 is a diagram of four ventricular cycles representing various scenarios that may occur during ventricular cycles over which a control parameter metric is being determined.

FIG. 8 is a diagram 350 of four ventricular cycles, labeled I, II, III, and IV, representing various scenarios that may occur during the eight (or other predetermined number) ventricular cycles over which an A4 sensing control parameter metric is being determined from the motion sensor signal. In some examples, each ventricular cycle may be classified by control circuit 206 as an "applicable" cycle or a "non-applicable" cycle depending on whether an A4 window is started or not. Control circuit 206 may determine whether adjustment criteria are met, e.g., at block 306 of FIG. 6, based on the number of applicable cycles during a consecutive series of the predetermined number of ventricular cycles.

In the example of FIG. 7, an A4 signal was detected during the A4 window 326 during each ventricular cycle. This may not always be the case, however. For instance, in the first ventricular cycle I of FIG. 8, a VP 352 is followed by an A3 window 354 and an A4 window 356, however the motion sensor signal 351 does not cross the high A4 sensing threshold 376 or the low A4 sensing threshold 368 before the ventricular pacing interval (VV interval) 358 expires. The VV interval 358 may be a programmed lower ventricular rate interval or may be adjusted from the lower ventricular rate interval to a rate smoothing interval based on a recently determined actual ventricular rate. A VP 362 is generated by pulse generator 202 upon expiration of the VV interval 358. Since an A4 signal is not sensed, the A4 event amplitude cannot be determined during the first ventricular cycle I. However, the ventricular cycle I may be considered an applicable cycle for the purposes of determining when A4 sensing control parameter adjustment criteria are met (e.g., at block 306 of FIG. 6). The A4 sensing control parameter adjustment criteria may require that the A4 window is started for at least a threshold number of the predetermined number of ventricular cycles, for example. The first ventricular cycle I may be determined to be an applicable cycle by control circuit 206 since an A4 window 356 was started, even though an A4 signal was not sensed.

The second ventricular cycle II starts with VP 362 and ends with VP 372, which is generated by pulse generator 202 at an AV pacing interval 370 from an A4 sensed event signal 365. The A4 window 366 is started at the ending time 325 of the A3 window, and the A4 signal 360 is sensed during the A4 window 366 due to the motion signal crossing the low A4 sensing threshold amplitude 368. The second ventricular cycle II is counted as an applicable cycle by control circuit 206 because an A4 window 366 is started. The maximum amplitude of the motion sensor signal during the A4 window 366 may be determined by control circuit 206 for use in determining the minimum detected A4 amplitude over a predetermined number of ventricular cycles as one A4 sensing control parameter metric determined from the motion sensor signal by control circuit 206.

The third ventricular cycle III starts upon VP 372 and ends upon VP 382. In this cycle, the A4 signal 380 crosses the high A4 sensing threshold 376 during the A3 window 374. As such an A4 window is never started. The VP 382 is delivered at an AV pacing interval 370 from the A4 sensed event signal 375. Since an A4 window is not started, the third ventricular cycle III may be classified as a non-applicable cycle by control circuit 206 for purposes of determining an applicable cycle count and applying criteria for adjusting an A4 sensing control parameter and/or for determining an adjustment applied to the A4 sensing control parameter. An applicable cycle may be any ventricular cycle that is longer than the A3 window ending time 325.

In some examples, control circuit 206 extends the A3 window ending time 325 when the A4 event is sensed during the A3 window 374, as in ventricular cycle III. Control circuit 206 starts AV pacing interval 370 which may expire after the normally scheduled A3 window ending time 325. As such, control circuit 206 may extend the A3 window ending time from scheduled ending time 325 to an extended ending time 327 that occurs simultaneously with the expiration of the AV pacing interval 370, so that no A4 window is started. In this case, the extended A3 window ending time 327 expires with the AV pacing interval 270 that was started during the A3 window 374 but may end later than the normal A3 window ending time 325 when the A4 event is sensed late in the A3 window 374. The extended A3 window ending time 327 ends with the ventricular pacing pulse 382, which precludes starting the A4 window so that the ventricular cycle III is not counted as an applicable cycle.

The fourth ventricular cycle IV starts upon VP 382 and ends on a ventricular sensed event 392. In this example, the A3 window 384 is started, but an intrinsic R-wave, which may be a premature ventricular contraction (PVC), is sensed by cardiac electrical signal sensing circuit 204 as shown by ventricular sensed event signal (VS) 392 during the A3 window 384, before an A4 window is started. The fourth ventricular cycle IV is classified as a non-applicable cycle by control circuit 206 because an A4 window is not started.

Accordingly, in some examples, each ventricular cycle of the predetermined number of ventricular cycles, e.g., eight, over which an A4 sensing control parameter metric is determined from the motion signal may be classified as either "applicable" when an A4 window is started (whether or not the A4 signal is sensed) or "non-applicable" when an A4 window is not started. In some examples, adjustment criteria at block 306 of FIG. 6 may require a minimum number of applicable cycles to be reached during each set of N ventricular cycles. When fewer than the threshold number of applicable cycles are classified and counted by control circuit 206, the adjustment criteria at block 306 may be determined to be unmet since insufficient A4 signal amplitude and timing information may be available.

As in FIG. 7, the durations of the A3 windows, A4 windows, AV pacing intervals 370 and ventricular cycles I, II, III and IV shown in FIG. 8 are illustrative and conceptual in nature and not intended to be limiting. The relative durations of the A3 windows, A4 windows, AV pacing intervals and overall ventricular cycles may not be shown according to a relative time scale to one another. For example, an A4 window 356 that is started in ventricular cycle I and ends with a ventricular pacing pulse 362 at the VV pacing interval 358 will tend to be a relatively long A4 window (when no A4 event is sensed) compared to an A4 window 366 during which the A4 event is sensed, as in ventricular cycle II. The A4 windows may be longer than or shorter than the A3 windows, depending on when and if the A4 event is sensed. As such, it is noted that the relative time durations of the A3 windows and A4 windows may vary from cycle to cycle and may be different relative to one another, the ventricular cycle lengths and the AV pacing interval than as shown in the examples of FIG. 8.

Figure 9:
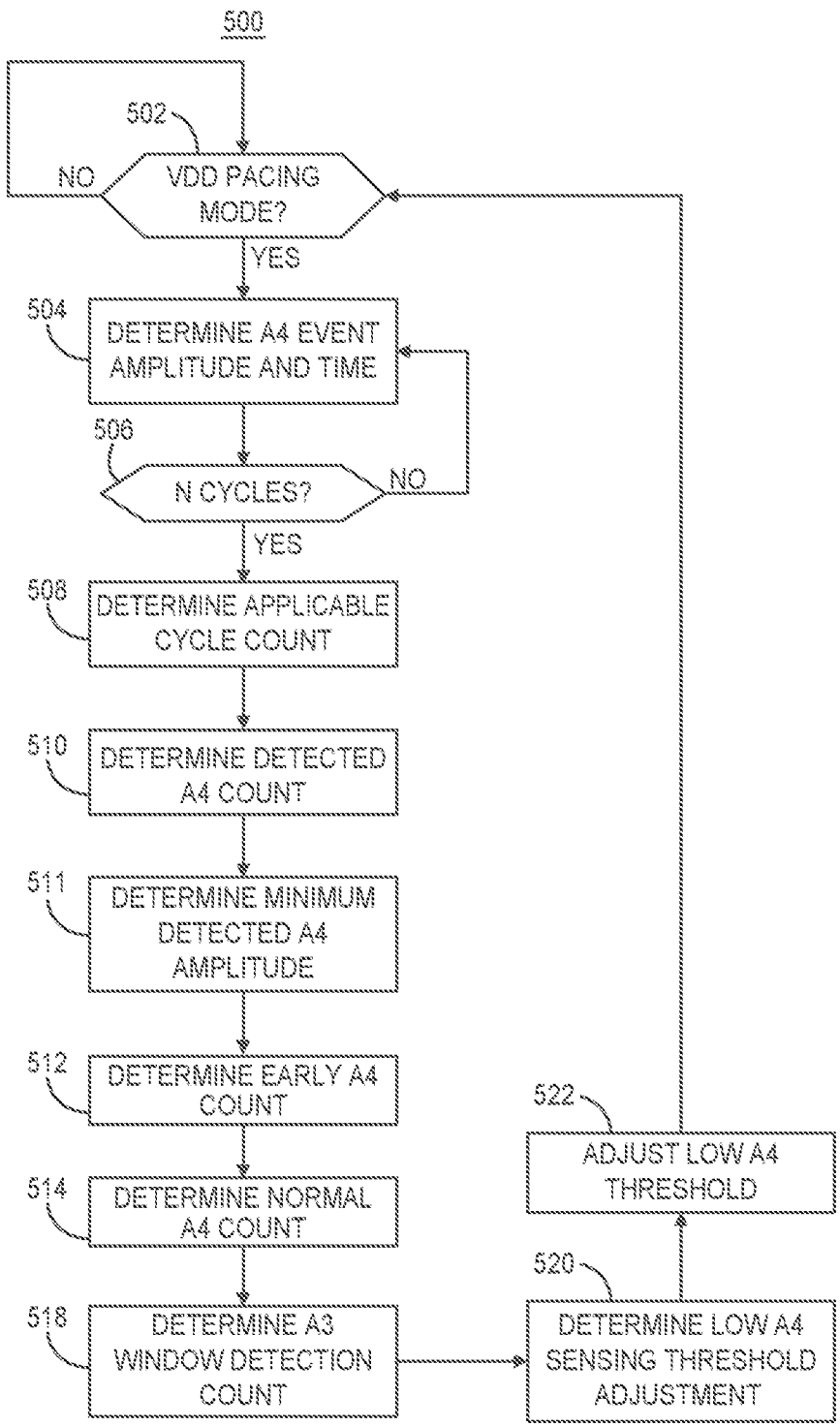
FIG. 9 is a flow chart of a method for determining control parameter metrics for use in adjusting an atrial event low sensing threshold according to one example.

FIG. 9 is a flow chart 500 of a method for determining A4 sensing control parameter metrics by control circuit 206 for use in adjusting the low A4 sensing threshold according to one example. In some examples, the A4 sensing threshold is automatically adjusted by control circuit 206 only during an atrial tracking ventricular pacing mode, e.g., a VDD pacing mode, which may be a temporary or permanent VDD pacing mode. When the pacing mode is a non-atrial tracking pacing mode, e.g., VDI(R) or VVI(R), adjustments of the low A4 sensing threshold may be disabled or suspended. As shown in FIG. 5, the low A4 sensing threshold, e.g., threshold 448 is the threshold amplitude applied to the motion sensor signal after the A3 window ending time for sensing A4 events. If the pacing mode is an atrial tracking pacing mode at block 502, control circuit 206 determines the A4 event amplitude and time at block 504 for each A4 event that is sensed during the A4 window following each ventricular pacing pulse or sensed R-wave for a predetermined number of ventricular cycles, e.g., eight cycles. The predetermined number of ventricular cycles may be consecutive cycles, e.g., as shown in FIG. 7, but A4 events may or may not be sensed in the A4 window of each of the consecutive ventricular cycles.

For each A4 event that is sensed over the N ventricular cycles, the A4 event amplitude may be determined as the maximum peak amplitude of the motion sensor signal after the low A4 sensing threshold crossing that occurs later than the A3 window ending time (and before the next ventricular electrical event). The A4 event time may be determined as the sample number or time stamp of the maximum peak amplitude since the most recent preceding ventricular electrical event (either the most recent preceding ventricular pacing pulse or sensed R-wave).

Control circuit 206 continues to determine the A4 event amplitude and time for each A4 event sensed during an A4 window (block 504) until N ventricular cycles have elapsed (block 506). In some cases, an A4 event may not be sensed during the A4 window for each of N ventricular cycles or an A4 window may not occur (due to an early sensed R-wave or an early sensed A4 event during the A3 window) as described in conjunction with FIG. 8 above. As such, in some examples, after N ventricular cycles have elapsed, up to N A4 event amplitudes and A4 event times, but sometimes fewer than N A4 event amplitudes and A4 event times, may be determined by control circuit 206 and buffered in memory 210 for the N ventricular cycles.

Once N ventricular cycles have elapsed ("yes branch of block 506), control circuit 206 may determine one or more A4 sensing control parameter metrics based on the motion sensor signal over the N ventricular cycles. At block 508, control circuit 206 may determine the applicable cycle count. The applicable cycle count is the number of cycles out of the N ventricular cycles in which the A4 window is started as described above in conjunction with FIG. 8. A buffer in memory 210 may store a flag for each ventricular cycle that includes an A4 window during the N ventricular cycles to facilitate determination of the applicable cycle count at block 508. Even though an A4 window is started during a ventricular cycle, an A4 event may or may not be sensed during the A4 window. Another buffer in memory 210 may store a flag for each ventricular cycle of the N ventricular cycles during which an A4 event is sensed during the A4 window to facilitate determination of a detected A4 count at block 510. Control circuit 206 may count the number of flags in the buffer that are set in response to each A4 sensed event signal generated by atrial systolic event detector circuit 240 during an A4 window over the N ventricular cycles.

At block 511, the minimum detected A4 amplitude is determined as the lowest value of A4 event amplitudes determined at block 504 over the N ventricular cycles. At block 512, control circuit 206 may determine an early A4 count. An A4 event sensed during the A4 window within a predetermined threshold time interval of the ending time of the A3 window is classified as an early A4 event. For instance, each A4 sensed event signal that occurs within 50 ms (or other selected time interval) of the ending time of the A3 window may be counted as an early A4 event. Control circuit 206 may subtract the A3 window ending time from the A4 event time determined at block 504 and compare the difference to a threshold time interval, e.g., 50 ms. If the difference is less than the threshold time interval, an early A4 event flag may be stored in a buffer in memory 206 for the corresponding ventricular cycle. Control circuit 206 may determine the early A4 count at block 512 by counting the number of early A4 event flags set over the N ventricular cycles.

At block 514, control circuit 206 determines a normal A4 count by counting the number of A4 sensed event signals generated by atrial systolic event detector circuit 240 during the A4 window at or later than the early event threshold time interval. For example, control circuit 206 may set a flag in a buffer for each ventricular cycle during which an A4 sensed event signal is generated at 50 ms or more after then ending time of the A3 window. Control circuit 206 may count the number of normal A4 event flags set over the N ventricular cycles at block 514.

Control circuit 206 determines the A3 window detection count at block 518. Each time an A4 event is sensed during the A3 window, in response to the motion sensor signal crossing the high A4 sensing threshold amplitude, the A4 event may be fused or overlapping with the A3 event or the A3 event may be oversensed as an A4 event. In some instances, atrioventricular synchrony may be lost due to a loss in regular A4 event sensing, which may occur when the A3 event is oversensed as an A4 event, before the A4 signal actually occurs during the ventricular cycle. A loss of atrial tracking by the ventricular pacing pulses may occur in conjunction with A3 event oversensing, as evidenced by frequent A4 sensed event signals generated by atrial systolic event detector circuit 240 during the A3 window and/or early after the A3 window ending time. The ventricular pacing pulses may be tracking oversensed A3 events instead of true A4 events. In this situation, decreasing the low A4 sensing threshold amplitude during the A4 window may contribute to A3 event oversensing with the associated loss in atrial tracking of the ventricular pacing pulses. As such, for each ventricular cycle during the N ventricular cycles that an A4 sensed event signal is generated by atrial systolic event detector circuit 240 during the A3 window, control circuit 206 may set an A3 window detection flag in a buffer in memory 210 to facilitate determining an A3 window detection count at block 518. This count of A4 events sensed in A3 windows may be used in verifying conditions of A3 event oversensing and/or possible A4 event undersensing that is occurring due to A3 event oversensing.

At block 520, control circuit 206 may determine whether the low A4 sensing threshold amplitude should be adjusted and, if so, determines the adjustment to be made based on the various A4 sensing control parameter metrics determined at blocks 508-518 over the N ventricular cycles. For example, when the currently set low A4 sensing threshold amplitude does not exceed an upper adjustment limit and a threshold number of early A4 events are counted, the low A4 sensing threshold amplitude may be increased. When the minimum detected A4 amplitude is less than or equal to a predetermined factor of the currently set low A4 sensing threshold amplitude, the low A4 sensing threshold may be decreased to restore a desired safety margin between the minimum detected A4 amplitude and the low A4 sensing threshold amplitude. When the minimum detected A4 amplitude is greater than a predetermined factor of the currently set low A4 sensing threshold amplitude, the low A4 sensing threshold may be increased. Various criteria based on the A4 sensing control parameter metrics that may be applied at block 520 in determining whether to increment the low A4 sensing threshold, decrement the low A4 sensing threshold or leave the low A4 sensing threshold unchanged are described below in conjunction with FIG. 10.

When adjustment criteria are met and the appropriate increment or decrement is determined at block 520, control circuit 206 adjusts the low A4 sensing threshold amplitude at block 522. In some examples, the low A4 sensing threshold amplitude is increased or decreased by a predetermined increment or decrement, respectively, when specified conditions are met. In other examples, the low A4 sensing threshold amplitude may be adjusted to a value that is determined based on one or more of the control parameter metrics. For example, the low A4 sensing threshold amplitude may be adjusted to a value that is set based on the minimum detected A4 amplitude. For instance, the low A4 sensing threshold amplitude may be adjusted directly to a fraction or percentage of the minimum detected A4 amplitude to achieve a desired safety margin rather than being adjusted by a predetermined increment or decrement.

After adjusting the low A4 sensing threshold amplitude at block 522, control circuit 206 may return to block 502 to proceed with determining the A4 sensing control parameter metrics for the next series of N ventricular cycles as long as the atrial tracking pacing mode remains in effect (as determined at block 502). In some examples, the pacing mode may only be switched on every eight ventricular cycles, concurrently with the determination of the A4 sensing control parameter metrics and any resulting A4 sensing control parameter adjustments. As such, if a pacing mode switch occurs, e.g., to a rate responsive pacing mode or a non-atrial tracking ventricular pacing mode, the automatic adjustment of the low A4 sensing threshold amplitude may be suspended or disabled until control module 206 switches back to the atrial tracking ventricular pacing mode. In other examples, the pacing mode may switch during the N ventricular cycles. When this occurs, control circuit 206 may suspend and disable the A4 sensing threshold amplitude adjustment without determining A4 sensing control parameter metrics after N cycles if the new pacing mode is not an atrial tracking ventricular pacing mode.

Furthermore, while the flow chart 500 (and other flow charts presented herein) refer to some A4 sensing control parameters being adjusted after every N cycles (based on A4 sensing control parameter metrics determined from the N cycles), it is to be understood that the adjustment may be suspended for a predetermined interval of time or number of ventricular cycles between the sets of N cycles to provide periodic adjustment of one or more A4 sensing control parameters. The number of ventricular cycles between each set of N cycles may be greater than, less than or equal to N. To illustrate, the low A4 sensing threshold (or another A4 sensing control parameter) may be adjusted after 8 ventricular cycles. Control circuit 206 may suspend adjustments for the next 8 to 16 cycles, then adjust the low A4 sensing threshold again after the next 8 ventricular cycles. In this way the low A4 sensing threshold amplitude may be adjusted based on the most recent 8 ventricular cycles but is adjusted every 16 to 24 cycles, as an example.

Figure 10:
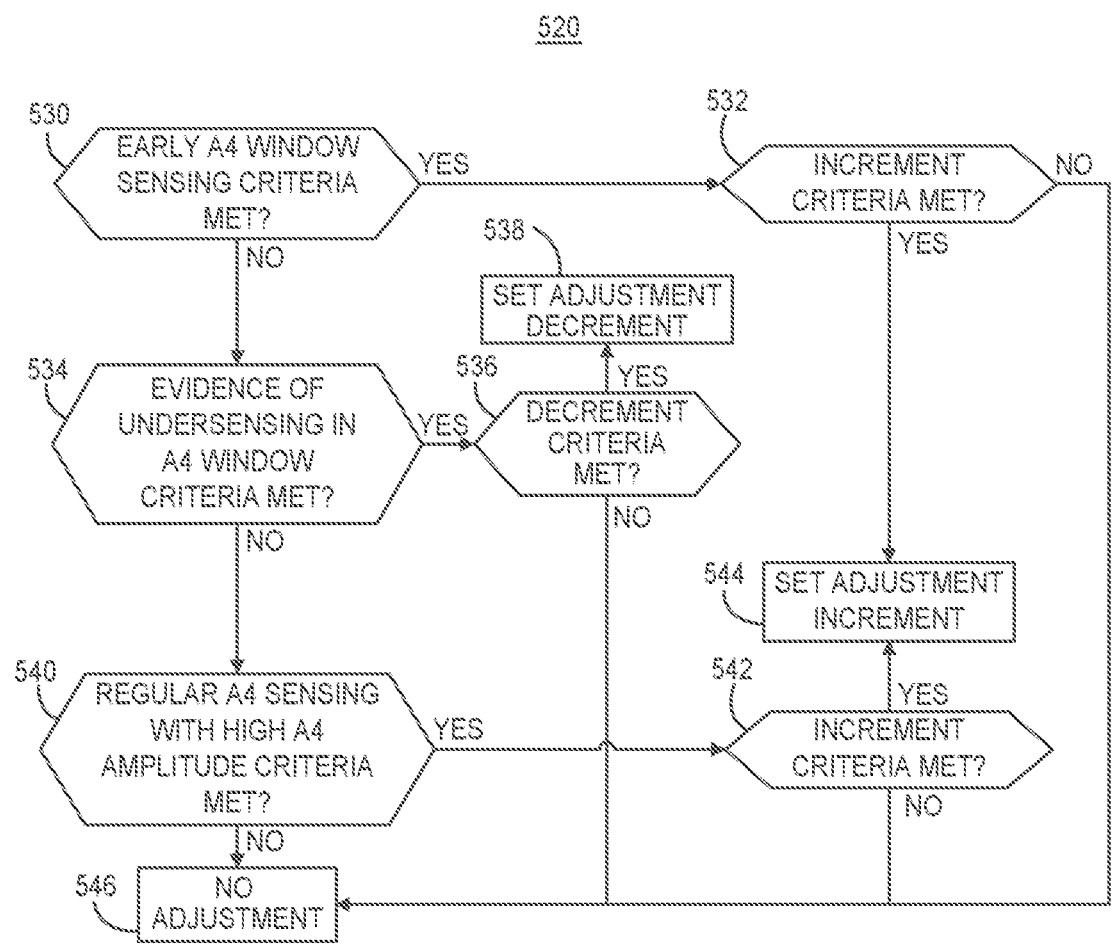
FIG. 10 is a flow chart of a method for determining an adjustment to the atrial event low sensing threshold amplitude according to one example.

FIG. 10 is a flow chart 520 of a method for determining an adjustment to the low A4 sensing threshold amplitude according to one example. The process of flow chart 520 may correspond to the determination performed by control circuit 206 at like-numbered block 520 of FIG. 9. As such, once an adjustment decision is made at block 538 (decrement), block 544 (increment) or block 546 (no adjustment) according to the process of flow chart 520 as described below, control circuit 206 may advance to block 522 of FIG. 9 to make the determined adjustment accordingly. In the process of flow chart 520, various conditions relating to the timing and/or amplitude of motion signal features and/or sensed A4 events may be analyzed by control circuit 206, based on an analysis of the A4 sensing control parameter metrics determined as described above in conjunction with FIG. 9. When specified conditions/criteria are met, control circuit 206 may determine that an adjustment, e.g., a predetermined increment or decrement, is to be applied at block 522 of FIG. 9.

For example, control circuit 206 may be configured to detect evidence of A3 event oversensing, or other motion signal oversensing, causing false A4 sensed event signals to be generated by atrial systolic event detector circuit 240. At block 530, control circuit 206 may detect evidence of A3 event oversensing when early A4 window sensing conditions are met. Control circuit 206 may determine that generated A4 sensed event signals are occurring early in the A4 window with a relatively high frequency. The low A4 sensing threshold amplitude applied during the A4 window may be lower than optimal when A4 events are being sensed relatively quickly after the A3 window ending time, e.g., within 50 to 100 ms after the A3 window ending time. When this occurs, the A4 event signal may actually be occurring later in the A4 window but due to a low value of the low A4 sensing threshold amplitude, A3 events or other motion signals may be oversensed as A4 events early in the A4 window before the true A4 event signal. Accordingly, control circuit 206 may examine the A4 sensing control parameter metrics to determine if A4 sensed event signals are frequently occurring relatively early in the A4 window at block 530, indicating possible A3 event or other motion signal oversensing.

Various criteria may be applied at block 530 by control circuit 206 to determine if A4 event signals are being sensed early in the A4 window such that early A4 window sensing conditions are met, suggesting that the A3 event signal, or the end of the A3 event signal, or other baseline motion signal noise is being sensed as the A4 event early after the A3 window ending time. In one example, control circuit 206 compares the early A4 count determined at block 512 of FIG. 9 to an early A4 count threshold value. For example, if the early A4 count (number of A4 sensed event signals generated within 50 ms or other predetermined time interval after A3 window ending time) is at least 1, 2, 3, 4 or other selected number out of (or percentage of) the N ventricular cycles, evidence of possible A3 event or other motion signal oversensing may be detected based at least on early A4 window sensing conditions being met at block 530.

Control circuit 206 may additionally or alternatively compare the early A4 count to the normal A4 count. The normal A4 count determined at block 514 (FIG. 9) is the number of A4 events sensed later than the predetermined time interval after the A3 window ending time, e.g., at 50 ms or later after the A3 window ending time. When the early A4 count is at least equal to or greater than the normal A4 count, control circuit 206 may detect evidence of frequent A3 event or other motion signal oversensing leading to false A4 sensed event signals being generated early in the A4 window.

In some examples, a combination of conditions may be required to be met, e.g., requiring a threshold value of the early A4 count and the early A4 count being greater than or equal to the normal A4 count, for control circuit 206 to determine that early A4 window sensing conditions are met at block 530. In an illustrative example, control circuit 206 may determine that the early A4 window sensing conditions are met at block 530 when the early A4 count is at least 25% of the N ventricular cycles (e.g., 2 out of eight ventricular cycles) and the early A4 count is greater than or equal to the normal A4 count. In other examples, one or more amplitude conditions may be required to be met at block 530 that would indicate that false A4 event sensing may be occurring. For example, if the maximum motion sensor signal amplitude during the A4 window occurs more than a threshold time interval after the low A4 sensing threshold crossing time (and the A4 sensed event signal is generated) for each of the early A4 events counted, this amplitude condition may indicate premature A4 event signal sensing due to oversensing of the A3 event signal and/or other motion signals.

Various early A4 window sensing conditions may be applied by control circuit 206 at block 530. Such criteria may be time-based and/or amplitude-based criteria. For example, control circuit 206 may compare the time of sensed A4 events (e.g., the time of the low A4 sensing threshold amplitude crossing during the A4 window) to early A4 window sensing criteria, compare the time from the low A4 sensing threshold amplitude crossing to a maximum motion sensor signal amplitude during the A4 window to early A4 window sensing criteria, compare the difference between the maximum motion sensor signal amplitude during the A4 window and the low A4 sensing threshold amplitude to early A4 window sensing criteria, and/or other timing and/or amplitude related criteria that are indicative of probable premature sensing of a non-A4 event during the A4 window, e.g., due to A3 event oversensing early in the A4 window. When early A4 window sensing conditions/criteria are met, control circuit 206 may determine if criteria for incrementing the low A4 threshold are met at block 532.

Control circuit 206 may apply the increment criteria at block 532 in order to avoid increasing the low A4 sensing threshold above a maximum limit, and/or increasing the low A4 sensing threshold that is already at a relatively high value. For example, the adjusted low A4 sensing threshold amplitude value may be limited to be no more than a low A4 threshold maximum limit, which may correspond to an acceleration of 5 m/s$^2$ or other selected upper limit. It is to be understood that examples of acceleration thresholds or maximum and minimum values given herein may be implemented in ADC units in atrial event detector circuit 240. For instance, each ADC unit may correspond to 11.8 milli-g (where 1 g is the acceleration of gravity) and 100 milli-g may correspond to 1 m/s$^2$ acceleration. When control circuit 206 determines that adjusting the low A4 sensing threshold by a predetermined increment would cause the low A4 sensing threshold amplitude to exceed the maximum limit, the increment criteria at block 532 are unmet. Control circuit 206 may determine that no adjustment should be made at block 546.

Additionally or alternatively, control circuit 206 may compare the current value of the low A4 sensing threshold amplitude to an adjustment threshold at block 532. For instance, the current value of the low A4 sensing threshold amplitude may be required to be less than or equal to twice (or other multiple of) a minimum limit of the low A4 sensing threshold amplitude. To illustrate, if the minimum available setting of the low A4 sensing threshold amplitude is 0.8 m/s$^2$, the currently set low A4 sensing threshold amplitude may be required to be equal to or less than twice the minimum setting, or 1.6 m/s$^2$ in this example for the increment criteria to be met at block 532. If the currently set low A4 sensing threshold amplitude is greater than the adjustment threshold, control circuit 206 may determine that the increment criteria are not met at block 532, and a determination of no adjustment is made at block 546.

In other examples, control circuit 206 may compare the current value of the low A4 sensing threshold amplitude to one half (or other fraction of) the maximum available setting of the low A4 sensing threshold amplitude. Generally, the control circuit 206 may determine that the increment criteria are met a block 532 when the current setting of the low A4 sensing threshold amplitude is relatively low in the range of available settings, e.g., in the lower half of the range of available settings.

In still other examples, control circuit 206 may additionally or alternatively compare the current value of the low A4 sensing threshold amplitude to one or more previous values of the low A4 sensing threshold amplitude. The maximum (or minimum) allowable setting of the low A4 sensing threshold amplitude may be based on one or more historical values of the low A4 sensing threshold amplitude. For instance, the low A4 sensing threshold amplitude may be limited to a maximum value that is set to a percentage of the maximum, mean or median of low A4 sensing threshold amplitude settings that may be buffered in memory 210, e.g., the most recent four, eight, twelve or other recent values. In other examples, the historical values of the A4 sensing threshold amplitude settings may be stored since the time of implant and start of operation of pacemaker 14.

When control circuit 206 determines that the early A4 window sensing conditions are met at block 530 and the increment criteria are met at block 532, control circuit 206 may determine that the low A4 sensing threshold amplitude is to be adjusted by a predetermined increment of ADC units, e.g., one or more ADC units, which may correspond to an acceleration increment of 0.1 m/s$^2$, 0.2 m/s$^2$, 0.25 m/s$^2$, 0.3 m/s$^2$, or other predetermined acceleration increment. Control circuit 206 may set the adjustment increment at block 544 to be used for adjusting the low A4 sensing threshold amplitude at block 422 of FIG. 9. The increment may be a fixed increment, e.g., 0.3 m/s$^2$, that is used any time early A4 window sensing conditions are met at block 530 and the increment criteria are met at block 532. It is to be understood that the adjustment may be a portion of a predetermined increment when increasing by a whole increment would exceed a maximum upper limit of the low A4 sensing threshold amplitude.

In other examples the increment set at block 544 may be an adjustable increment that may be relatively larger or smaller depending on the current value of the low A4 sensing threshold amplitude, the values of the A4 sensing control parameter metrics and conditions met at block 530. For example, when the early A4 count is relatively high or much greater than the normal A4 count and/or the current value of the low A4 sensing threshold amplitude is at or near the minimum limit, a relatively higher increment may be set at block 544. If the early A4 count is relatively low or equal to the normal A4 count, or the current value of the low A4 sensing threshold amplitude is near a maximum limit or in a higher range of available settings, a relatively lower increment may be set at block 544. In this way, the adjustment increment set at block 544 may be scaled based on one or more factors, such as the current value of the low A4 sensing threshold amplitude, the frequency of A4 events that are sensed early in the A4 window and/or the difference between the current value of the low A4 sensing threshold amplitude and the minimum detected A4 amplitude during the A4 windows over the N ventricular cycles.

When the early A4 window sensing conditions are not met at block 530 ("no" branch of block 530), control circuit 206 may determine if conditions/criteria are met that indicate possible undersensing of the A4 event signal during the A4 window. When the A4 event is not sensed in the A3 window, so that an A4 window is started at the A3 window ending time, and an A4 event signal is not detected before the next ventricular pacing pulse or sensed R-wave, the A4 event signal may be undersensed due to the low A4 sensing threshold amplitude being set too high. Accordingly, control circuit 206 may compare one or more of the A4 sensing control parameter metrics determined over the N ventricular cycles to criteria for detecting evidence of A4 event undersensing during the A4 window at block 534.

In one example, control circuit 206 compares the detected A4 count (determined at block 510 of FIG. 9) to the applicable cycle count (the number of ventricular cycles during which the A3 window ends and an A4 window is started as determined at block 508 of FIG. 9). When the detected A4 count is less than the applicable cycle count by more than a threshold difference (or percentage), control circuit 206 may detect evidence of undersensing in the A4 window at block 534. Various comparisons may be made by control circuit 206 to determine if the number of A4 events sensed during the A4 windows that occur over the N ventricular cycles is relatively low, indicating possible undersensing of the A4 event signal. For example, a ratio of the detected A4 count to the applicable cycle count may be compared to a threshold ratio or percentage. Control circuit 206 may detect evidence of A4 undersensing when the detected A4 count is less than 100%, 90%, 80%, 75%, 70% or other selected percentage of the applicable cycle count.

In some examples, the applicable cycle count may be required to be greater than or equal to a specified threshold, e.g., at least 3, 4, 5 or other selected number (or percentage) of the N ventricular cycles in order to detect evidence of A4 undersensing during the A4 window. Control circuit 206 may determine that a minimum threshold number of A4 windows are started (upon the A3 window ending before the end of the ventricular cycle) over the N ventricular cycles in order for the conditions to be met for detecting evidence of A4 undersensing at block 534. When a small portion of the N ventricular cycles have an A4 window started, e.g., only one out of eight ventricular cycles or less than 20% (or other threshold percentage) of the N ventricular cycles, there may be insufficient evidence to detect likely A4 event undersensing. Conditions that may result in no A4 window being started during a ventricular cycle are described above in conjunction with FIG. 8. In some examples, control circuit 206 determines whether the number of applicable cycles over the N ventricular cycles is less than 50%, 40%, 30%, 25%, 20%, or 15% of the N ventricular cycles in order for criteria to be met for determining A4 undersensing during the A4 window at block 534.

Control circuit 206 may determine that evidence of A4 event undersensing criteria are met at block 534 when the detected A4 count is less than a threshold percentage of, or difference from, the applicable cycle count and the applicable cycle count is at least a threshold count. For instance, when at least five out of eight ventricular cycles are applicable cycles (have an A4 window started) and an A4 event is sensed during fewer than two less than the number of applicable cycles, criteria for detecting evidence of undersensing of the A4 event during the A4 windows may be met at block 534. Additionally or alternatively, control circuit 206 may compare the normal A4 count to a threshold at block 534. When a threshold number of applicable cycles occur but no normal A4 events are sensed, which are A4 events sensed at least a predetermined time interval, e.g., 50 ms, after the A3 window ending time, A4 event undersensing during the A4 window may be occurring, which may be due to a low A4 threshold amplitude that is set too high.

In still other examples, control circuit 206 may compare the minimum detected A4 amplitude (determined at block 511 of FIG. 9) to a threshold, which may be based on the current setting of the low A4 sensing threshold amplitude. When the minimum detected A4 amplitude is less than a threshold amplitude, the likelihood of A4 event undersensing may be increased due to an insufficient safety margin between the low A4 sensing threshold amplitude and the minimum detected A4 amplitude. The minimum detected A4 amplitude threshold may be set to a multiple of the current low A4 sensing threshold amplitude value, e.g., 1.1, 1.2, 1.25, 1.5, 2.0 or other selected multiple. When the minimum detected A4 amplitude threshold is not at least a safety margin greater than the current low A4 sensing threshold amplitude, the likelihood of A4 event undersensing may be increased.

A combination of two or more criteria, including any of those described above, may be checked by control circuit 206 at block 534 to determine if conditions for detecting evidence of A4 event undersensing are met. In an illustrative example, control circuit 206 detects evidence of A4 event undersensing at block 534 when the applicable cycle count is at least 5 out of 8 ventricular cycles, the detected A4 count is less than two fewer than the applicable cycle count, and the minimum detected A4 amplitude is less than or equal to 1.5 times the current low A4 sensing threshold amplitude setting or the normal A4 count is zero. When these criteria are met, control circuit 206 may determine that A4 event undersensing is likely and the low A4 sensing threshold amplitude should be decreased. Control circuit 206 may advance to block 536 to determine if decrement criteria are met.

By detecting evidence of A4 event undersensing at block 534, control circuit 206 may adjust the low A4 threshold amplitude when the low A4 threshold amplitude is set too high for reliably sensing A4 events. However, in some instances, the low A4 threshold amplitude may be set appropriately, but true A4 events may not be sensed because A3 events, occurring earlier in the ventricular cycle, are being oversensed, precluding sensing of the later true A4 events. When the cause of A4 events being undersensed is only due to the low A4 threshold amplitude being set too high, few or no A4 events are expected to be detected during the A3 window. However, when the A3 window ending time is set too early or the high A4 threshold amplitude is set too low, oversensing of A3 events may contribute to the undersensing of true A4 events during the A4 window. In this case, adjustment to the high A4 threshold amplitude and/or the A3 window ending time may restore reliable A4 sensing, without requiring an adjustment to the low A4 threshold amplitude.

Accordingly, in some examples, in determining that criteria for detecting A4 event undersensing during the A4 window are met at block 534, control circuit 206 may apply criteria for verifying that oversensing of the A3 event is not occurring over the N ventricular cycles and contributing to the undersensing of the later A4 event. In some instances, e.g., with changing heart rate or other factors, the A3 window ending time may be set to end near or slightly earlier than the A3 event. In this case, the A3 window ending time may require adjustment before the low A4 threshold amplitude is adjusted. Criteria applied at block 534 may include comparing the A3 window detection count (determined at block 518 of FIG. 9) to a threshold. In some examples, control circuit 206 may require that zero A4 events are detected during the A3 window (A3 window detection count is zero over the N ventricular cycles) in order for the A4 event undersensing criteria to be met at block 534, leading to a possible decrement of the low A4 threshold amplitude at block 538.

Another condition that may be applied at block 534 for verifying that A3 event oversensing is not contributing to undersensing of A4 events may require that relatively few A4 events are sensed early in the A4 window, e.g., within 50 ms or other specified time interval of the A3 window ending time. Several early A4 sensed event signals may occur over the N ventricular cycles when the A3 event signal is occurring after the A3 window ending time, resulting in A3 events being oversensed as early A4 events. If this is occurring, the low A4 sensing threshold amplitude should not be decremented or A3 event oversensing may occur even more frequently. Instead, the A3 window ending time may require adjusting. Examples of criteria applied by control circuit 206 for verifying that A3 oversensing is not occurring may include requiring that the early A4 count (determined at block 512 of FIG. 9) is less than a threshold number, e.g., less than 2 out of the eight ventricular cycles and/or that the early A4 count is less than the normal A4 count.

When all criteria for determining A4 undersensing during the A4 window are met at block 534, which may include criteria for verifying that A3 oversensing is not occurring, control circuit 206 may determine if decrement criteria are met at block 536. The low A4 sensing threshold amplitude may be decremented when the decrement does not cause the low A4 sensing threshold amplitude to be less than a minimum value. Other criteria relating to the minimum detected A4 amplitude and/or current setting of the low A4 sensing threshold amplitude may be applied to avoid decreasing the low A4 sensing threshold amplitude when the current low A4 sensing threshold amplitude is near the minimum available setting and/or near the minimum detected A4 amplitude.

When the decrement criteria are met at block 536, control circuit 206 sets the decrement at block 538 that is used to adjust the low A4 sensing threshold amplitude at block 522 of FIG. 9. The decrement may be a fixed, predetermined value, e.g., one or more ADC units, e.g., 0.3 ms/s$^2$. In other examples, the decrement may be an adjustable or scaled decrement. Control circuit 206 may determine the decrement based on the current setting of the low A4 sensing threshold amplitude and/or the minimum detected A4 amplitude.

When the decrement criteria are not met at block 536, control circuit 206 may determine that the low A4 sensing threshold amplitude should not be decreased from its current value even though evidence of A4 event undersensing was detected at block 534 with no evidence of A3 event oversensing. Control circuit 206 may advance to block 546 so that no adjustment is made at block 522 of FIG. 9.

If the criteria for determining A4 event undersensing during the A4 window are not met at block 534, control circuit 206 may advance to block 540 to determine if regular A4 sensing with high A4 event amplitude criteria are met. When A4 events having a high amplitude are regularly sensed, an increase in the low A4 sensing threshold amplitude may be justified. High A4 event amplitude criteria may be met when control circuit 206 determines that regular A4 event sensing during the A4 windows over the N ventricular cycles and/or the sensed A4 event amplitudes are relatively high compared to the current low A4 sensing threshold amplitude. For example, when a majority of the N ventricular cycles include A4 events sensed during the A4 window, A4 event sensing may be determined to be regular. When the peak amplitude of each of the regularly sensed A4 events is greater than a predetermined margin above the current setting of the low A4 sensing threshold amplitude, the high A4 amplitude criteria may be determined to be met by control circuit 206 at block 540.

In one example, control circuit 206 may determine that the regular A4 sensing with high A4 amplitude criteria are met by determining that the applicable cycle count is greater than a threshold, determining that the detected A4 count equals the applicable cycle count, determining that the normal A4 event count is at least a threshold number and that the minimum detected A4 event amplitude is greater than an adjustment threshold. The applicable cycle count threshold may be greater than half of the N ventricular cycles in some examples. For instance, the applicable cycle count may be required to be at least five out of the eight ventricular cycles analyzed. When the detected A4 count equals the applicable cycle count, A4 events are sensed in every A4 window and are determined to be regularly sensed. A threshold number of the detected A4 events may be required to be normal A4 events (i.e., sensed at least a predetermined time interval after the A3 window ending time). For example, the normal A4 cycle count may be required to be greater than one. The adjustment threshold applied to the minimum detected A4 event amplitude may be set to the current low A4 sensing threshold amplitude multiplied by an adjustment factor. For example, the adjustment factor may be 1.25, 1.5, 2.0 or other factor that provides a desired safety margin between the minimum detected A4 amplitude and the low A4 sensing threshold. When the minimum detected A4 amplitude as determined at block 511 is greater than 1.5 times the current low A4 sensing threshold amplitude setting, for example, the low A4 sensing threshold amplitude may be increased.

When control circuit 206 determines that A4 event sensing is occurring during A4 windows regularly and reliably (e.g., for at least 50% or more of the N ventricular cycles) and the minimum detected A4 amplitude is greater than a multiple of the low A4 sensing threshold amplitude, control circuit 206 determines that the criteria are met at block 540 and advances to block 542. Control circuit determines whether low A4 threshold amplitude increment criteria are met at block 542. For example, the current setting of the low A4 sensing threshold amplitude may be required to be less than a maximum upper limit by a threshold amount (e.g., by at least one ADC unit or more). Other increment criteria may be applied based on the minimum detected A4 event amplitude and/or the current setting of the low A4 sensing threshold amplitude to avoid introducing A4 event undersensing due to incrementing the low A4 sensing threshold amplitude.

When the increment criteria are met at block 542, control circuit 206 may advance to block 544 to determine the adjustment increment to be applied at block 522 of FIG. 9. The adjustment increment may be set to a fixed predetermined value corresponding to 0.1 m/s$^2$, 0.2 m/s$^2$, 0.25 m/s$^2$, 0.3 m/s$^2$ or other selected value. As described above, the adjustment increment may be adjustable or scaled based on the minimum detected A4 amplitude, the current setting of the low A4 sensing threshold amplitude, the difference between the current setting of the low A4 sensing threshold amplitude and the maximum or minimum limit, the difference between the minimum detected A4 amplitude and maximum or minimum limit, the detected A4 count, the normal A4 count, the early A4 count, and/or other A4 sensing control parameter metric or any combination thereof.

When control circuit 206 determines that the criteria for detecting regular A4 event sensing with high A4 amplitude are unmet (block 540) or that increment criteria are unmet (block 542), control circuit 206 may set the adjustment to zero at block 546 so that no adjustment to the low A4 sensing threshold amplitude is made at block 522 of FIG. 9.

It is to be understood that, when incrementing the low A4 sensing threshold amplitude by a predetermined fixed increment that would cause the low A4 sensing threshold amplitude to exceed a maximum allowable setting, control circuit 206 may set the adjustment increment to a portion of the fixed increment so that the low A4 sensing threshold amplitude is adjusted to the maximum limit without exceeding it. Likewise, in some instances, the adjustment decrement set at block 538 may be a portion of a predetermined fixed decrement when an adjustment by the fixed decrement would cause the low A4 sensing threshold amplitude to be less than a minimum limit. For example, the minimum setting may be an acceleration of 0.8 m/s$^2$. When the predetermined, fixed decrement is 0.3 m/s$^2$ and the current value of the low A4 sensing threshold amplitude is 0.9 m/s$^2$, decreasing the A4 sensing threshold amplitude by the fixed decrement would cause it to go below the minimum limit. In this case, the low A4 sensing threshold amplitude may be decremented to the minimum allowable setting of 0.8 m/s$^2$ instead of by one whole, predetermined fixed decrement value.

The various criteria and conditions described in conjunction with the flow chart 420 of FIG. 10 are described as being applied to the A4 sensing control parameter metrics in a particular order. It is to be understood, however, that the criteria may be applied in a different order than the order shown here. For example, one or more increment criteria of block 532 may be applied before and/or after determining if early A4 window sensing criteria are met or vice versa. Likewise, one or more decrement criteria may be applied before and/or after determining if A4 undersensing criteria are met at block 534 or vice versa. For example, control circuit 206 may check if the low A4 sensing threshold amplitude is already at a maximum or minimum limit before checking conditions that would cause an increment or a decrement, respectfully. Furthermore, it is contemplated that control circuit 206 may be configured to evaluate multiple criteria sequentially, simultaneously or in parallel combinations to arrive at a decision to increment, decrement or not adjust the low A4 sensing threshold amplitude.

When blocks 530, 534 and 540 are performed in the order show, control circuit 206 may give priority to checking for A3 event oversensing by checking for early A4 window sensing conditions being met at block 530. A3 event oversensing leads to a loss of atrial tracking by the ventricular pacing pulses during a VDD pacing mode. Ventricular pacing pulses that are tracking the A3 event, which is a ventricular event, may be delivered at relatively short ventricular cycles leading to fast pacing rates. As such, a first priority may be to ensure that A3 event oversensing is not occurring starting with the criteria described in conjunction with block 530.

The second priority may be to detect A4 event undersensing when A3 event oversensing is not occurring, as determined when criteria are met at block 534. In this case, ventricular pacing pulses may be delivered asynchronously with the A4 event due to VV pacing intervals expiring without A4 sensed event signals being generated to trigger an AV pacing interval. As such, while ventricular rate support is being provided, atrioventricular synchrony may be lost during A4 event undersensing. Accordingly, detecting undersensing of A4 events within the A4 window when no A3 event oversensing is occurring may be the second priority criteria used by control circuit 206 in making a decision to adjust the low A4 sensing threshold amplitude.

The lowest priority conditions for adjusting the low A4 sensing threshold amplitude may be applied at block 540 for increasing the low A4 sensing threshold amplitude in response to regular sensing of high amplitude A4 events. In this case, ventricular pacing may be properly tracking A4 events with reliable A4 sensed event signals. An adjustment to the low A4 sensing threshold amplitude may be optional under these conditions, but an increment may promote continued, reliable A4 event sensing while reducing any likelihood of oversensing A3 events or other motion signals occurring in the A4 window. As indicated above, however, while blocks 530, 534 and 540 are shown in a particular order that may correspond to a prioritized hierarchy based on how the A3 oversensing, A4 undersensing, and reliable A4 sensing may affect ventricular tracking of the atrial events, it is recognized that these criteria may be applied in parallel or simultaneous operations to arrive at an adjustment decision. Once an adjustment decision is made at block 538, 544 or block 546, control circuit 206 may advance to block 522 of the flow chart 500 of FIG. 9 to perform the adjustment of the low A4 sensing threshold amplitude accordingly.

Figure 11:
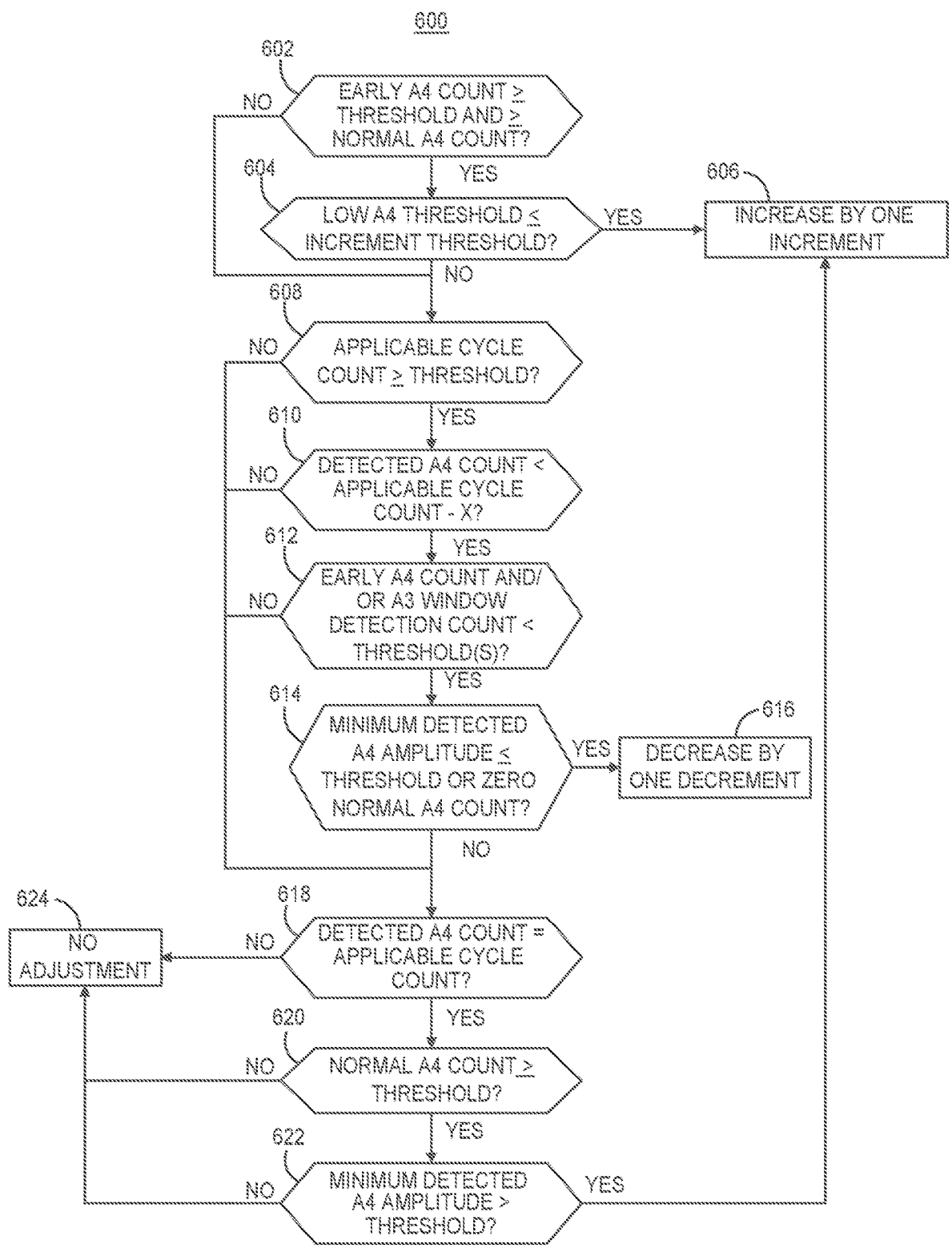
FIG. 11 is a flow chart of an illustrative method for determining when atrial event low sensing threshold adjustment criteria are met according to one example.

FIG. 11 is a flow chart 600 of an illustrative method for determining when low A4 sensing threshold adjustment criteria are met and setting the adjustment increment or decrement according to one example. Control circuit 206 may execute instructions stored in memory 210 to perform the various comparisons and decisions attributed to control circuit 206 in conjunction with FIG. 11 and other flow charts presented herein. The functionality may be implemented in any combination of hardware, firmware and/or software. The process of flow chart 600 may be performed after every N ventricular cycles using the A4 sensing control parameter metrics determined from the N ventricular cycles as described above in conjunction with FIG. 9. The A4 sensing control parameter metrics may include counts of all sensed A4 events, early A4 events, normal A4 events, A4 events sensed during the A3 window, and the minimum detected A4 event amplitude, as examples. The process of flow chart 600 is performed by control circuit 206 while control circuit 206 operates in an atrial tracking ventricular pacing mode (e.g., VDD pacing mode).

At block 602, control circuit 206 compares the early A4 count to a threshold value and to the normal A4 count. Control circuit 206 may detect A3 event oversensing in response to the early A4 event count being greater than a threshold, e.g., greater than a predetermined percentage of N (the number of ventricular cycles) and greater than the normal A4 event count. When the early A4 count is greater than the threshold value (e.g., 2 or more) and greater than or equal to the normal A4 count, control circuit 206 compares the current low A4 sensing threshold amplitude to an increment threshold at block 604. When the low A4 sensing threshold amplitude is less than or equal to the increment threshold, control circuit 206 increases the low A4 sensing threshold amplitude at block 606, which may be by one increment, e.g., by 0.3 m/s$^2$, to no more than an upper maximum limit, e.g., 5.0 m/s$^2$. When the low A4 sensing threshold amplitude is already greater than a multiple, e.g., twice, the minimum setting of the low A4 sensing threshold amplitude, the low A4 sensing threshold amplitude may not be increased by control circuit 206. In one example, the low A4 sensing threshold amplitude is not incremented when it is more than 1.6 m/s$^2$, twice the minimum setting of 0.8 m/s$^2$.

Blocks 602 and 604 generally correspond to criteria applied for determining that early A4 sensing conditions are met as evidence of possible A3 event oversensing and an increment criterion is met, respectively. By increasing the low A4 sensing threshold amplitude in response to detected frequent early A4 sensed events, the likelihood of persistent A3 event oversensing may be reduced. As such, the criteria applied at blocks 602 and 604 reflect a tradeoff between protecting against oversensing of the A3 event (by increasing the low A4 sensing threshold) while avoiding over-increasing the low A4 sensing threshold amplitude which may cause intermittent or persistent A4 event undersensing. It is desirable to increase the low A4 sensing threshold amplitude enough to avoid oversensing of the A3 event or other motion signals while keeping it low enough to reliably sense A4 events during the A4 window, particularly when the heart rate is relatively high and/or the A4 event signal has a relatively low amplitude.

When either of the criteria at block 602 or 604 are unmet, control circuit 206 advances to block 608 to compare the applicable cycle count to a threshold count, e.g., 5 when N=8 ventricular cycles that are evaluated for determining the A4 sensing control parameter metrics. When control circuit 206 determines that at least a threshold number of ventricular cycles are applicable cycles (cycles with an A4 window started), and the detected A4 count is less than the applicable cycle count minus X at block 610 (e.g., the detected A4 count is less than the applicable cycle count minus 2), A4 event undersensing criteria may be met. In other examples, the detected A4 count as a percentage of the applicable cycle count may be compared to a threshold percentage, e.g., 80%, 70% or other percentage. When the detected A4 count is less than a percentage threshold of the applicable cycle count, A4 undersensing may be suspected, and decreasing the low A4 sensing threshold amplitude may be warranted.

Control circuit 206 may determine if A3 event oversensing is likely at block 612 by comparing the early A4 count to a threshold count and/or comparing the early A4 count to the normal A4 count. When the early A4 count is less than 2 or another selected threshold, or the early A4 count is less than the normal A4 count, A3 oversensing is unlikely, supporting a determination of A4 undersensing during the A4 window and a need to decrement the low A4 sensing threshold amplitude.

At block 612, control circuit 206 may additionally or alternatively determine if the A3 window detection count (number of sensed A4 events that occur during the A3 window) is less than a threshold, e.g., less than 1 or a zero A3 window detection count. When zero A4 events are sensed during the A3 window and the early A4 count is less than a threshold count and less than the normal A4 count, A3 oversensing conditions are unmet, supporting a determination that criteria for detecting A4 undersensing are met and warranting a decreased low A4 sensing threshold amplitude.

Before decreasing the low A4 sensing threshold amplitude, control circuit 206 may determine whether the minimum detected A4 amplitude is less than a threshold amplitude at block 614. For example, control circuit 206 may determine that the minimum detected A4 amplitude is less than or equal to the current low A4 sensing threshold amplitude multiplied by a safety factor, e.g., multiplied by 1.5. In some examples, control circuit 206 may determine that the normal A4 count is zero at block 614, justifying decrementing the low A4 sensing threshold amplitude even when the minimum detected A4 amplitude is not greater than the current low A4 sensing threshold amplitude multiplied by a safety factor.

The criteria applied at blocks 608, 610 and 612 generally correspond to criteria applied at block 534 of FIG. 10 for determining A4 undersensing without A3 oversensing. When the criteria at blocks 608, 610 and 612 are met and the decrement criteria are met at block 614, control circuit 206 may decrease the low A4 sensing threshold amplitude at block 616 by one ADC unit or other selected decrement, but no less than the minimum allowable low A4 sensing threshold amplitude, e.g., 0.8 m/s$^2$.

Control circuit 206 may apply the A3 oversensing criteria of block 612 and the decrement criteria at block 614 to avoid decreasing the low A4 sensing threshold amplitude when A4 sensing and atrial tracking of the ventricular pacing pulses may be temporarily lost. The low A4 sensing threshold amplitude may be decreased only when the detected A4 count is less than the applicable cycle count by at least 2 (or other selected difference threshold) and the minimum detected A4 amplitude is low (less than a threshold) or a normal detected A4 count is zero, all of which criteria support a detection of A4 event undersensing associated with low amplitude A4 event signals. When the A3 window detection count is higher than a threshold, or the early A4 count is higher than a threshold (e.g., higher than the normal A4 count), A3 oversensing may be occurring, which may be causing the relatively later A4 event signal to go unsensed in some ventricular cycles. However, decreasing the low A4 sensing threshold amplitude may be unwarranted if a transient condition causes temporary A3 event oversensing associated with a temporary loss of A4 sensing during the current N ventricular cycles. Control circuit 206 may be configured to avoid decrementing the low A4 sensing threshold under such conditions, e.g., by checking the amplitude of the A4 event signals using the minimum detected A4 amplitude or another A4 signal amplitude metric at block 614.

A temporary loss of A4 sensing may occur when premature ventricular contractions (PVCs) occur during the N ventricular cycles, the patient makes a posture change or other conditions. In an illustrative example, if two non-consecutive premature ventricular contractions (PVCs) occur in the 8 ventricular cycles, the applicable cycle count may reach six. A4 windows may not be started during the two PVC cycles when the PVC occurs during the A3 window. The A4 event may not be sensed on the next ventricular cycle following each PVC because the A4 window may not correspond to the atrial rate on the first cycle after a PVC. If the A4 event is missed on just one other cycle, the number of detected A4 events out of the eight ventricular cycles may be only three. In this scenario, the A4 event undersensing criteria of the applicable cycle count being at least 5 (six applicable cycles) and the detected A4 count being less than two fewer than the applicable cycle count (only three sensed A4 events) are satisfied. However, by applying the minimum detected A4 amplitude criteria at block 614, the decrement criteria may be unmet. Of the three A4 event signals that are sensed, the minimum detected A4 amplitude may be greater than a safety factor times the low A4 sensing threshold amplitude, indicating that the low A4 sensing threshold amplitude is at an appropriate value but other factors may have caused temporary, transient A4 undersensing criteria to be met, in this case two PVCs.

Thus, this check of the minimum detected A4 amplitude when A4 undersensing criteria are met avoids decreasing the low A4 sensing threshold amplitude when the A4 event signals have a relatively high amplitude but other factors, e.g., PVCs, may be the underlying cause of the A4 undersensing criteria being met during the N ventricular cycles. Holding the low A4 sensing threshold amplitude at the current value may allow regular A4 sensing to be regained during the next N ventricular cycles, with AV synchrony being restored by the atrial tracking ventricular pacing, without requiring an adjustment to the low A4 sensing threshold amplitude. In this example, application of the minimum detected A4 amplitude criteria (block 614) avoids decreasing the low A4 sensing threshold amplitude even when the detected A4 count is low (at block 610), e.g., due to a temporary loss in sensing the A4 events due to PVCs or other transient, non-sustained changes in the heart rhythm, patient position or activity, or other factors.

When any of the criteria at blocks 608, 610, 612 or 614 are unmet, control circuit 206 advances to block 618 to determine if regular A4 sensing is occurring with relatively high A4 event signal amplitudes. At blocks 618 and 620, control circuit 206 determines if regular A4 event sensing is occurring by comparing the detected A4 count to the applicable cycle count and comparing the normal A4 count to a threshold count, respectively. In one example, when the detected A4 count equals the applicable cycle count (A4 sensed event signal generated in every A4 window that occurs over N ventricular cycles) and the normal A4 count is at least 1, control circuit 206 determines that regular A4 sensing is occurring. The criteria applied at blocks 618 and 620 correspond generally to criteria that may be applied at block 540 of FIG. 10 for determining regular A4 sensing with high A4 amplitude. When these criteria are met, control circuit 206 advances to block 622 to determine whether increment criteria are met.

At block 622, control circuit 206 may compare the minimum detected A4 amplitude to a threshold. The threshold may be based on the current setting of the low A4 sensing threshold amplitude multiplied by a safety factor, e.g., 1.5. When the minimum detected A4 amplitude is greater than the threshold at block 622, control circuit 206 determines that the low A4 sensing threshold amplitude may be safely increased at block 606 without impairing or disrupting the regular A4 event sensing. Control circuit 206 may increase the low A4 sensing threshold amplitude by a predetermined increment, e.g., 0.3 m/s$^2$ or other selected increment. Other multiples of the low A4 sensing threshold amplitude may be used as a threshold for comparing to the minimum detected A4 amplitude as described above in conjunction with FIG. 7. The multiple used to set the increment criteria at block 622 effectively sets the minimum safety margin required between the low A4 sensing threshold amplitude and the minimum detected A4 amplitude to promote reliable A4 event sensing.

In some instances, control circuit 206 may determine that none of the criteria applied at blocks 602, 604, 608, 610, 612, 614, 618, 620, and 622 are met such that no adjustment is performed at block 624. In this situation, A4 events may be sensed regularly, and the low A4 sensing threshold amplitude is deemed appropriate based on the minimum detected A4 amplitude being at least an acceptable safety margin of the current low A4 sensing threshold amplitude.

At other times, however, A4 events may be undersensed due to A3 event oversensing during the A3 window or after the A3 window ending time yet increment or decrement criteria may not be met. In this case, adjustment of the low A4 sensing threshold amplitude may not correct the situation of A3 event oversensing. Rather an adjustment to the high A4 sensing threshold amplitude applied during the A3 window and/or adjustment of the A3 window ending time may be a more appropriate response to restore reliable A4 event sensing. Techniques for automatically adjusting the high A4 sensing threshold amplitude and the A3 window ending time are described below.

Figure 12:
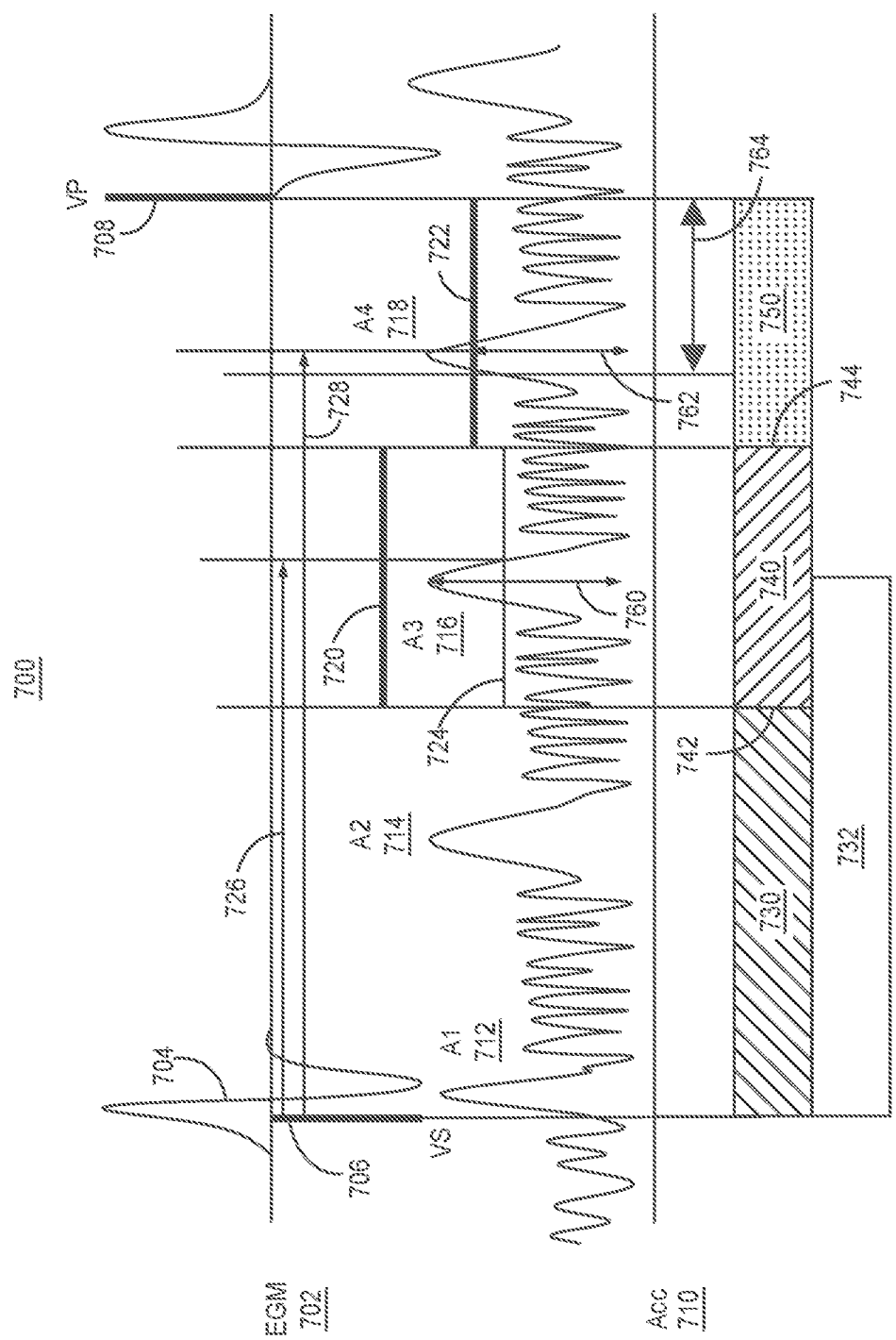
FIG. 12 is a diagram of an electrogram (EGM) signal, a motion sensor signal and various features of the motion sensor signal that may be determined for determining A4 sensing control parameter metrics.

FIG. 12 is a diagram 700 of an EGM signal 702 that may be produced by sensing circuit 204 and a motion signal 710 produced by motion sensor 212, shown here as an acceleration signal (ACC). Diagram 700 depicts A4 sensing control parameters and A4 sensing control parameter metrics that may be determined from motion signal 710 by control circuit 206 for use in adjusting at least some of the A4 sensing control parameters. The A4 sensing control parameters depicted in FIG. 12 include the A3 window ending time 744, the high A4 sensing threshold amplitude 720 applied to motion signal 710 during the A3 window 740, and the low A4 sensing threshold amplitude 722 applied after the A3 window ending time 744 during the A4 window 750. The A4 sensing control parameters further include the post-ventricular atrial blanking period 730 and the post-ventricular atrial refractory period 732. A4 sensing control parameter metrics that may be determined from motion signal 710 by control circuit 206 include an A3 event time 726, A3 event amplitude 760, an A4 event time 728 and an A4 event amplitude 762. Each of these A4 sensing control parameter metrics may be determined for use by control circuit 206 in adjusting the A3 window ending time 744 and/or the high A4 sensing threshold amplitude 720.

The EGM signal 702 includes an R-wave 704, which may be an intrinsic R-wave sensed by sensing circuit 204. Sensing circuit 204 may generate and R-wave sensed event signal 706 which starts a post-ventricular atrial blanking period 730 (during which no A4 events are sensed) and a post-ventricular atrial refractory period (PVARP) 732, during which A4 events may be sensed after expiration 742 of blanking period 730 but do not cause an AV pacing interval to be started by pace timing circuit 242 (FIG. 3). The PVARP 732 may be adjusted every N ventricular cycles in some examples, based on a ventricular rate during the N ventricular cycles. Post-ventricular atrial blanking period 730 may extend up to 550 ms in some examples. PVARP 732 may be set to at least the blanking period 730 and to no longer than the A3 window ending time 744 but will generally expire earlier than the A3 window ending time 744. For example, the A3 window 740 may start at 550 ms (end of blanking period 730) and extend to an ending time 744 that is 600 ms up to 1000 ms after the ventricular event 706. PVARP 732 may expire at 550 to 600 ms after the R-wave sensed event signal 706.

The PVARP 732 may be adjusted based on a ventricular rate metric determined as the median or nth longest ventricular cycle interval out of N ventricular cycles e.g., the $4^{th}$ longest out of eight ventricular cycles. The ventricular cycle intervals, e.g., RR intervals, may each start and end with a sensed R-wave or ventricular pacing pulse. In one example, control circuit 206 sets PVARP 732 to the ventricular rate metric less an offset, e.g., a median ventricular cycle interval less 100 to 200 ms. In one example, PVARP 732 is adjusted after every N (e.g., 8) ventricular cycles to the nth longest (e.g., fourth longest) ventricular cycle interval minus 130 ms, but not less than a minimum PVARP (e.g., 500 ms) and not more than a maximum PVARP (e.g., 600 ms). The offset used to set the PVARP 732 based on the ventricular rate metric may include a PVARP adjustment offset, e.g., 100 ms, plus the AV pacing interval, e.g., 10 ms, 20 ms, or 30 ms as examples. In this way, the PVARP 732 may be shortened during fast heart rates but is not extended longer than a maximum, e.g., 600 ms, during slow heart rates to promote non-refractory sensing of the A4 event signals.

During the blanking period 730, the A1 event 712 and A2 event 714 occur and are not sensed by atrial event detector circuit 240. At the expiration of the blanking period 730, control circuit 206 starts the A3 window 740 which extends to the A3 window ending time 744. The A3 event 716 occurs during the A3 window 740. In the example shown, the A3 event 716 is not sensed as an A4 event since the motion signal 710 does not cross the high A4 sensing threshold amplitude 720 applied during A3 window 740. However, control circuit 206 may set a low A3 threshold amplitude 724 that is applied during the A3 window 740 for use in determining the time of the A3 event 716 as an A4 sensing control parameter metric used in adjusting the A3 window ending time 744. The low A3 threshold amplitude 724, which is also referred to herein as "a ventricular diastolic event threshold amplitude," may be set equal to the low A4 sensing threshold amplitude 722 or lower, e.g., 75% of the low A4 sensing threshold amplitude. The A3 event 716 crosses the low A3 threshold amplitude 724 at a time 726 from the R-wave sensed event signal 706 (the start of the ventricular cycle). This low A3 sensing threshold crossing time 726 may be referred to as the "A3 event time" 726. The low A3 sensing threshold crossing time 726 is shown as the latest, negative-going crossing time of the A3 sensing threshold 724. In other examples, a positive-going crossing time of the A3 sensing threshold 724 may be determined as the A3 event time.

During some ventricular cycles, the motion signal 710 may cross the low A3 threshold amplitude 724 more than once during the A3 window 740. In some examples, therefore, the A3 event time 726 may be determined as the latest crossing time of the low A3 threshold amplitude 724 during A3 window 740, which may be the latest negative-going crossing of the low A3 threshold amplitude 724. Control circuit 206 may adjust the A3 window ending time 744 based on the latest crossing time of the low A3 threshold amplitude 724 to avoid setting the A3 window ending time 744 too early, which may lead to oversensing of the A3 event 716 during the A4 window 750. As further described below, control circuit 206 may determine the A3 event time 726 during each of N ventricular cycles for use in adjusting the A3 window ending time 744 after every N ventricular cycles or less often, as needed. Control circuit 206 may therefore be configured to determine a latest time in the A3 window 740 that the motion signal 710 is greater than the low A3 threshold amplitude 724 so that the A3 window ending time 744 may be set appropriately after the A3 event signal 716 has ended (or at least returned to a low amplitude that will not be oversensed as an A4 event).

In other ventricular cycles, the motion sensor signal 710 may not cross the low A3 threshold amplitude 724. In this case, the A3 event time may not be determined. Control circuit 206 may count the number of ventricular cycles that the A3 event time is not determined due to no low A3 sensing threshold crossing. In other examples, the A3 event time may be set to a minimum predetermined or default value, e.g., 550 ms, to indicate that the A3 window ending time 744 may be adjusted to a relatively early time after the ventricular event 706 without concern of the A3 event signal 716 having an amplitude that is greater than the low A4 sensing threshold amplitude 722. In still other ventricular cycles, a premature ventricular contraction or other fast ventricular beat may occur before the A3 window 740 or before the A3 window ending time 744, causing the A3 window 740 to not be started or at least not be completed during the ventricular cycle. The A3 event time may not be determined by control circuit 206 for the ventricular cycle when the A3 window 740 is not started or does not reach the A3 window ending time 744 in some examples. Control circuit 206 may count the number of ventricular cycles that the A3 event time is not determined due to no or incomplete A3 windows.

The low A3 threshold amplitude 724 applied during the A3 window 740 for detecting the A3 event time 726 may be set based on the low A4 sensing threshold amplitude 722 in some examples. For instance, the low A3 threshold amplitude 724 may be set to 60%, 70%, 75%, 80%, 90%, 100% or other selected percentage of the low A4 sensing threshold amplitude 722 that is applied after the A3 window ending time 744, during the A4 window 750. In one example, low A3 threshold amplitude 724 is set to be 75% of the low A4 sensing threshold amplitude 722 and may be adjusted up or down every N ventricular cycles with the low A4 sensing threshold amplitude 722 as it is adjusted according to any of the examples described above in conjunction with FIGS. 9-11.

Control circuit 206 may be configured to determine the A3 event amplitude 760 during each of the N ventricular cycles. Control circuit 206 may determine the A3 event amplitude 760 for use in adjusting the high A4 sensing threshold amplitude 720 as further described below. The A3 event amplitude 760 may be determined as the maximum peak amplitude of the motion signal 710 during the A3 window 740. In some instances, the A3 event amplitude 760 is determined as the maximum sample point amplitude that occurs after the low A3 threshold amplitude 724 is crossed by the motion sensor signal 710. However, the maximum peak amplitude 760 does not necessarily always occur after the latest motion sensor signal crossing time of the low A3 threshold amplitude, particularly when the latest negative-going crossing time is determined as the A3 event time 726. As such, the A3 event amplitude 760 may occur earlier or later in the A3 window 740 than the A3 event time 726. The time of the A3 event amplitude 760 may be independent of the A3 event time 726. Though, in some examples, the A3 event amplitude 760 may be determined as the maximum amplitude that is greater than or equal to the low A3 threshold amplitude 724 such that, in some instances, the A3 event amplitude 760 and the A3 event time 726 could occur at the same sample point.

During some ventricular cycles, the motion signal 710 may not cross the low A3 threshold amplitude 724 such that an A3 event time is not determined. When the low A3 threshold amplitude 724 is not crossed, the A3 event amplitude 760 may or may not be determined as the maximum sample point amplitude during the A3 window 740. When the low A3 threshold amplitude 724 is not crossed, control circuit 206 may determine the A3 event amplitude to be unknown. As such, in some examples, control circuit 206 determines the A3 event amplitude as the maximum amplitude that is greater than (or equal to) the low A3 threshold amplitude 724.

In addition to determining the A3 event amplitude 760 and the A3 event time 726, control circuit 206 may be configured to determine the A4 event amplitude 762 and the A4 event time 728 during the A4 window 750 of each of the ventricular cycles (of the N ventricle cycles) that an A4 window 750 is started. The A4 window 750 is started when the A3 window 740 ends without a sensed A4 event or a sensed R-wave. The A4 event time 728 may be determined as the time interval from the ventricular electrical event 706 that starts the ventricular cycle (in this cycle the R-wave sensed event signal 706 but in other cycles a ventricular pacing pulse) until the maximum amplitude 762 of the motion signal 710 during the A4 window 750 (after the A3 window ending time 744). In other examples, control circuit 206 may determine the A4 event time 728 as the time interval from the most recent ventricular electrical event to the earliest crossing time of the low A4 sensing threshold amplitude 722. Control circuit 206 may determine the A4 event time 728 for use in adjusting the A3 window ending time 744 as described below, alone or in combination with the A3 event time 726.

In some ventricular cycles, the motion signal 710 may not cross the low A4 sensing threshold amplitude 722 even though an A4 window 750 is started. The low A4 sensing threshold amplitude 722 may be set too high, a ventricular pace or sensed R-wave may occur before the low A4 sensing threshold amplitude 722 is crossed, or an atrial beat may not occur during the A4 window to cause the A4 event 718. As such, the A4 event time may not be determined by control circuit 206 for every ventricular cycle that includes an A4 window. Control circuit 206 may or may not determine the A4 event amplitude 762 when the A4 event time is not determined for a given ventricular cycle. Control circuit 206 may determine the A4 event amplitude 762 as the maximum sample point amplitude during the A4 window 750 that is greater than the low A4 sensing threshold amplitude 722.

As shown in FIG. 12, when the A4 event 718 is sensed by atrial event detector circuit 240 (FIG. 3) outside the PVARP 732, e.g., in response to the motion signal 710 crossing the low A4 sensing threshold amplitude 722, an AV pacing interval 764 is started by pace timing circuit 242. Pulse generator 202 generates a ventricular pacing pulse 708 in response to the expiration of the AV pacing interval 764, which ends the ventricular cycle and the A4 window 750. During other ventricular cycles, atrial event detector circuit 240 may sense an A4 event in response to the motion signal 710 crossing the high A4 sensing threshold amplitude 720 during the A3 window 740, e.g., when the heart rate is high and the A4 event signal is fused with the A3 event signal resulting in a combined high amplitude fused A3/A4 event signal.

If the A4 event is sensed during the A3 window 740 outside of the PVARP 732, the AV pacing interval 764 is started by pace timing circuit 242. Pulse generator 202 generates a pacing pulse upon expiration of the AV pacing interval 764 to provide atrial tracking of A4 event sensed after PVARP 732, during either A3 window 740 or A4 window 750.

It is noted that when the atrial event detector circuit 240 senses the A4 event during the A3 window 740, the A3 window 740 may be extended until the next ventricular event. For example, pace timing circuit 242 may start the AV pacing interval 764 in response to the A4 event being sensed during the A3 window 740. The AV pacing interval 764 may extend beyond the scheduled A3 window ending time 744. However, to avoid another A4 sensing threshold crossing during the ventricular cycle, control circuit 206 may extend the A3 window 740 until the AV pacing interval expires and the ventricular pacing pulse is delivered. Control circuit 206 may extend the A3 window 740 until the next ventricular event, sensed or paced, when the high A4 sensing threshold amplitude 720 is crossed so that the A4 window 750 is not started during the same ventricular cycle. The A3 window is extended to avoid another A4 sensing threshold amplitude crossing in the same ventricular cycle. In this case, the A4 event time 728 and the A4 event amplitude 762 are not determined since the A4 window 750 is not started. The A3 window 740 may be effectively extended by holding the high A4 sensing threshold amplitude 720 until the next ventricular electrical event, without decreasing the A4 sensing threshold to the low A4 sensing threshold amplitude 722.

Figure 13:
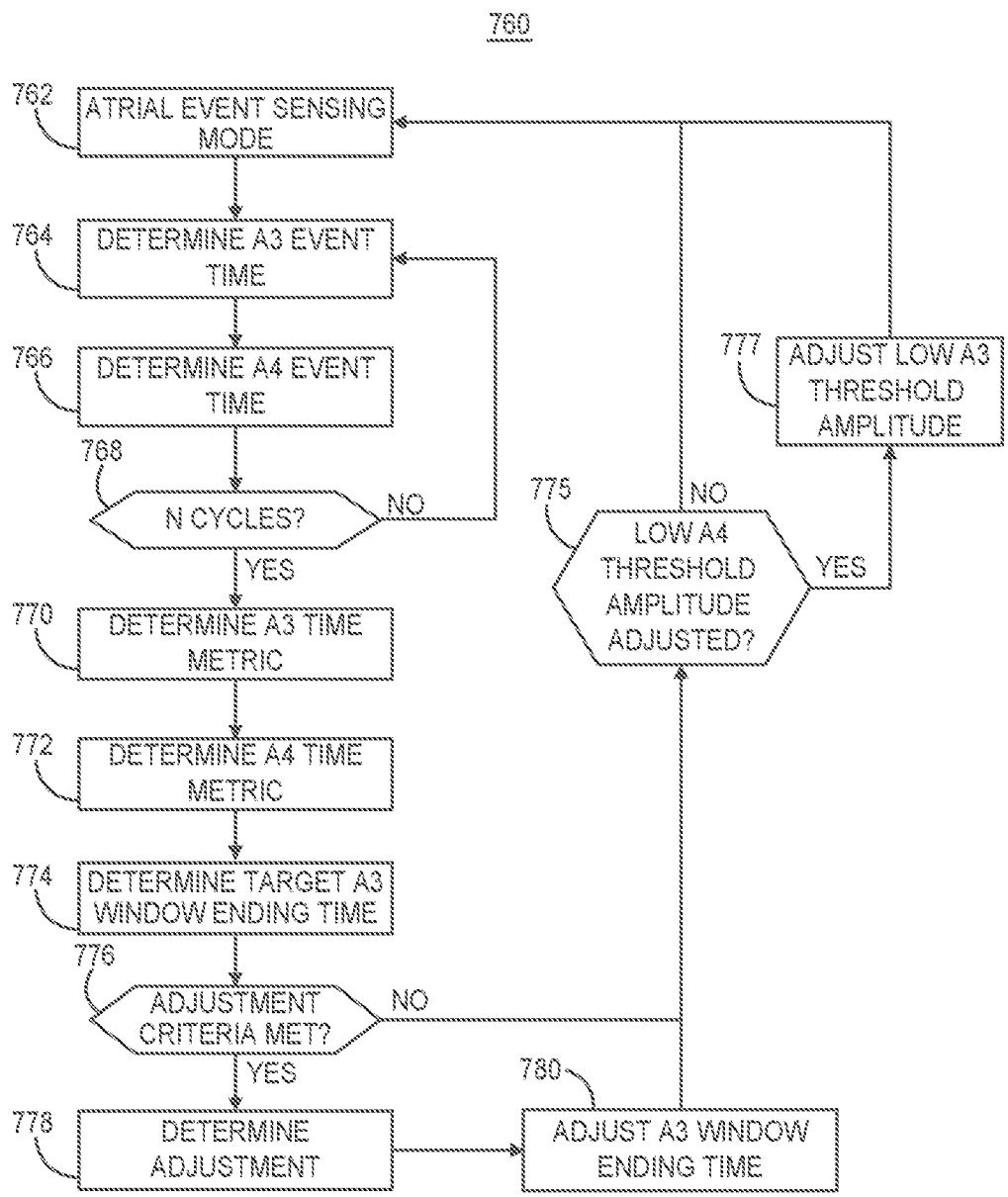
FIG. 13 is a flow chart of a method performed by a medical device for determining A4 sensing control parameter metrics and adjusting a sensing window ending time according to one example.

FIG. 13 is a flow chart 760 of a method performed by control circuit 206 for determining A4 sensing control parameter metrics from a motion signal and adjusting the A3 window ending time according to one example. At block 762, control circuit 206 determines that the current operating mode includes atrial event sensing. For example, control circuit 206 may be operating in an atrial tracking ventricular pacing mode, e.g., a temporary or permanent VDD pacing mode that includes A4 event sensing. At other times, control circuit 206 may be operating in a non-atrial tracking ventricular pacing mode but with atrial sensing (dual chamber sensing) enabled, e.g., a VDI pacing mode. During a VDD or VDI pacing mode, adjustments to the A3 window ending time may be enabled. Control circuit 206 may disable determining A4 sensing control parameter metrics and adjustments of the A3 window ending time when the pacing mode is a rate responsive pacing mode, e.g., VDIR pacing mode, or a single chamber sensing mode, e.g., VVI or VVIR pacing mode.

With reference to the A4 sensing control parameter metrics described above in conjunction with FIG. 12, in response to a ventricular electrical event (sensed R-wave or ventricular pacing pulse) starting a new ventricular cycle, control circuit 206 may determine the A3 event time 726 at block 764. Control circuit 206 may determine the A4 event time 728 at block 766 for the ventricular cycle when an A4 window 750 is started and the low A4 sensing threshold amplitude is crossed. At block 768, control circuit 206 determines if N ventricular cycles have elapsed, e.g., eight ventricular cycles in the examples given above. If not, control circuit 206 returns to block 764 to continue determining the A3 event time and A4 event time for each ventricular cycle.

As described above, the A3 event time and/or A4 event time may not be determinable for some ventricular cycles, e.g., when an early R-wave is sensed so that the A3 and/or A4 window is not started or the motion signal does not cross the low A3 threshold amplitude or the low A4 sensing threshold amplitude. When the motion signal does not cross the low A3 threshold amplitude during a ventricular cycle, control circuit 206 may determine the A3 event time for that cycle as unknown. In other examples, the A3 event time may be set according to a specified value when the low A3 threshold amplitude is not crossed. For example, control circuit 206 may set the A3 event time to the minimum available setting of the A3 window ending time or the minimum available setting of the A3 window less a specified interval, e.g., less 50 ms. In one example, the minimum A3 window ending time is 600 ms so that control circuit 206 sets the A3 event time to 550 ms when the low A3 threshold amplitude is not crossed by the motion signal. When the motion signal amplitude stays below the low A3 threshold amplitude throughout the A3 window, the A3 window may be set to a minimum ending time since the risk of A3 event oversensing is minimal.

When an A4 window is not started in a ventricular cycle, the A4 event time for that ventricular cycle is unknown. Examples of when the A4 window 750 is not started are described above, e.g., when a ventricular electrical event occurs before the A3 window ending time 744 or the A3 window 740 is extended due to an A4 sensed event during the A3 window 740.

When the A4 window is started but the motion sensor signal does not cross the low A4 sensing threshold amplitude during the A4 window, control circuit 206 may set the A4 event time for that ventricular cycle to a default value. The default value may be based on the programmed lower ventricular pacing rate or a rate smoothing rate. Control circuit 206 may set a rate smoothing rate interval based on the actual ventricular rate so that the VV pacing interval may be set to a rate smoothing rate interval, which may be shorter than the lower ventricular pacing rate interval, in order to avoid an abrupt ventricular rate change to the lower ventricular pacing rate when an A4 event is not sensed. The rate smoothing interval may be adjusted gradually toward the lower rate interval when A4 events are not being sensed. When the motion sensor signal 710 does not cross the low A4 sensing threshold amplitude 722 during the A4 window 750, the A4 event time may be set to the rate smoothing interval plus an offset (which may be zero or other selected value) indicating that the A4 event time is relatively long, after the VV pacing interval. In other examples, the A4 event time may be set to the lower rate interval. In this way, an A4 event time may be determined by control circuit 206 when the A4 window is started to be at least the VV pacing interval even when the motion sensor signal 710 does not cross the low A4 sensing threshold amplitude 722 before the VV pacing interval expires.

After N ventricular cycles ("yes" branch of block 768), control circuit 206 may determine an A3 time metric at block 770 and an A4 time metric at block 772. The A3 time metric is determined from the individual A3 event times determined over the N ventricular cycles, and the A4 time metric is determined from the individual A4 event times determined over the N ventricular cycles. In various examples, as further described below, the A3 window ending time may be adjusted based on one or both of the A3 time metric and the A4 time metric. For instance, the A3 window ending time may be adjusted to be at least a threshold time interval later than the A3 time metric, at least a threshold time interval earlier than the A4 time metric, or at some interval between the A3 time metric and the A4 time metric.

The A3 time metric may be determined by control circuit 206 as the mean or median of all A3 event times determined from the N ventricular cycles. In other examples, the A3 time metric may be determined as a specified $n^{th}$ shortest (or longest) A3 event time determined from the N ventricular cycles. For example, when eight ventricular cycles are evaluated, the fourth shortest A3 event time may be determined as the A3 time metric at block 770. When less than four A3 event times are obtained from the N ventricular cycles, the A3 time metric may be determined as unknown, e.g., due to too few A3 windows being started. In other examples, the longest A3 event time of any A3 event times determined may be determined as the A3 event time metric.

At block 772, control circuit 206 determines the A4 time metric from the A4 event times determined during the N ventricular cycles. The A4 time metric may be determined as the mean, median or $n^{th}$ shortest (or longest) A4 event time. In one example, the A4 time metric is set to the fourth shortest A4 event time determined out of eight ventricular cycles. When fewer than four (or other specified requisite number of) A4 event times are determined for the N ventricular cycles, control circuit 206 may determine the A4 time metric as being unknown.

At block 774, control circuit 206 determines a target A3 window ending time based on the A3 time metric and/or the A4 time metric. In one example, the target A3 window ending time is determined as the A3 time metric plus a fraction or percentage of the difference between the A4 time metric and the A3 time metric. For example, control circuit 206 may determine the difference between the A3 time metric and the A4 time metric at block 774 then add 20%, 25%, 30%, 33%, 40% or other selected percentage of the difference to the A3 time metric to determine the target A3 window ending time. In this way, the target A3 window ending time is set to be a safety margin later than the expected A3 event time. In one example, the target A3 window ending time is the A3 time metric plus one-third of the difference between the A3 time metric and the A4 time metric. When either of the A3 time metric or the A4 time metric is determined to be unknown, the target A3 window ending time may be determined by control circuit 206 as being unknown or held to a previously determined value.

The percentage or fraction of the difference between the A3 time metric and the A4 time metric used to set the target A3 window ending time may be adjustable in some examples, e.g., based on the current ventricular rate and or based on the magnitude of the difference. A ventricular rate metric may be determined over the N ventricular cycles, which is used in determining the rate smoothing pacing interval in some examples. The target A3 window ending time may be set to the A3 time metric plus a first percentage of the difference between the A4 time metric and the A3 time metric when the ventricular rate metric is less than a rate threshold. The target A3 window ending time may be set to the A3 time metric plus a second percentage of the difference (different than the first percentage) when the ventricular rate metric is greater than or equal to the rate threshold. For instance, a higher percentage of the difference (e.g., 30%) may be used during relatively slower ventricular rates (e.g., less than 80, 90 or 100 beats per minute) than the percentage of the difference (e.g., 15%) during relatively higher ventricular rates (e.g., greater than 80, 90 or 100 beats per minute).

In some examples, the method used by control circuit 206 to determine the target A3 window ending time is selected according to the pacing operating mode in effect. The target A3 window ending time may be determined differently when the pacing mode is VDD than when the pacing mode is VDI for example. During the VDD pacing mode, control circuit 206 may determine the target A3 window ending time based on a combination of the A3 time metric and the A4 time metric as described above. During the VDI pacing mode, control circuit 206 may determine the target A3 window ending time based on the A3 time metric and not the A4 time metric. For example, control circuit 206 may determine the target A3 window ending time as the A3 time metric plus a specified offset, e.g., plus 50 ms, 100 ms, 150 ms or other selected offset. The offset may be scaled or adjusted based on the actual ventricular rate in some examples. During the non-atrial tracking VDI pacing mode, the atrial rate may be different than the ventricular rate such that A4 event signals do not reliably occur during the A4 window. The A3 event times may be determined, but any A4 event times may be unreliable. As such, during the VDI pacing mode, control circuit 206 may only use the A3 time metric and not the A4 time metric in determining the target A3 window ending time at block 774.

At block 776, control circuit 206 determines if A3 window ending time adjustment criteria are met. In order to determine if adjustment criteria are met, control circuit 206 may be configured to determine if the target A3 ending time is known or unknown and for what reason (e.g., too few A3 windows during the N ventricular cycles or too few low A3 threshold amplitude crossings during the A3 windows over the N ventricular cycles). Control circuit 206 may additionally or alternatively determine whether the A4 time metric is known or unknown. Control circuit 206 may be configured to compare the A3 time metric to the A4 time metric or compare their difference to a difference threshold in order to determine if adjustment criteria are met at block 776. Additionally or alternatively, control circuit 206 may be configured to compare the current value of the A3 window ending time 744 to the target A3 window ending time at block 776 to determine if adjustment criteria are met. Examples of methods control circuit 206 may perform for determining whether adjustment criteria are met at block 776 are described below in conjunction with FIG. 14.

When adjustment criteria are met at block 776, control circuit 206 determines what the adjustment should be (increase, decrease or no adjustment) at block 778 and performs the adjustment at block 780. Techniques for determining whether to increase, decrease or leave the A3 window ending time unchanged are described below in conjunction with FIG. 14. When control circuit 206 determines that adjustment criteria are unmet ("no" branch of block 776), control circuit returns to block 762 to determine the A4 sensing control parameter metrics over the next set of N ventricular cycles as long as the operating mode still includes atrial event sensing. If the operating mode has changed, control circuit 206 may suspend determining A4 sensing control parameter metrics used in adjusting the A3 window ending time and/or suspend adjusting the A3 window ending time.

As described above in conjunction with FIG. 12, the low A3 threshold amplitude used to determine the A3 event time at block 764 may be based on the low A4 sensing threshold amplitude. The low A4 sensing threshold amplitude may be adjusted after every N ventricular cycles, e.g., according to the techniques described above in conjunction with FIGS. 9-11. As such, before determining A3 event times during the next N ventricular cycles, control circuit 206 may determine whether the low A4 sensing threshold amplitude has been adjusted after then current N ventricular cycles at block 775. If the low A4 sensing threshold amplitude has been adjusted, e.g., based on the N ventricular cycles that have just ended ("yes" branch of block 775), control circuit 206 may adjust the low A3 threshold amplitude at block 777. The low A3 threshold amplitude is adjusted based on the adjusted low A4 sensing threshold amplitude, e.g., to 75% of the new low A4 sensing threshold amplitude or equal to the new low A4 sensing threshold amplitude. Otherwise, if the low A4 sensing threshold amplitude has not been adjusted, control circuit 206 returns to block 762 without adjusting the low A3 threshold amplitude.

Figure 14:
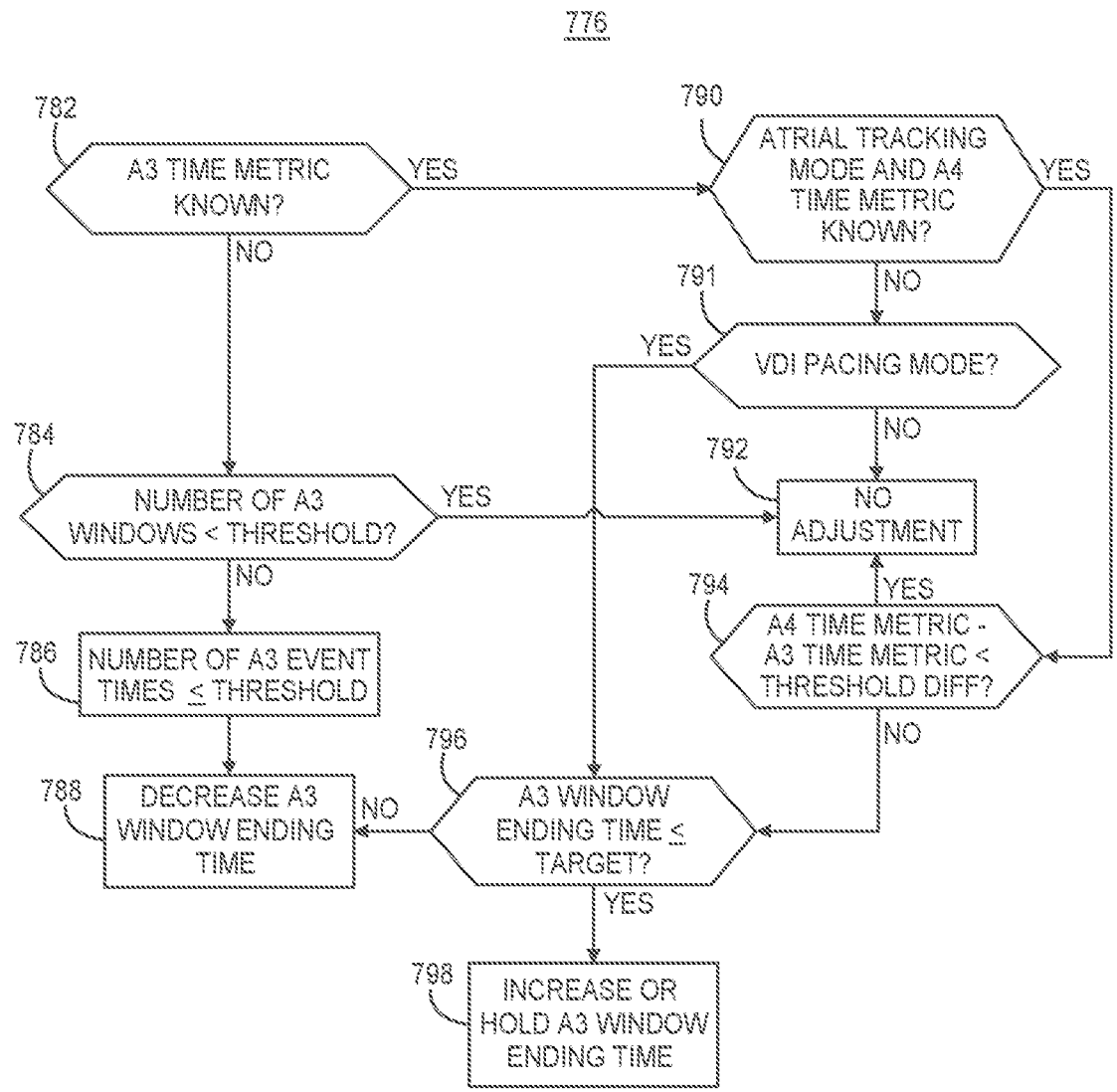
FIG. 14 is a flow chart of a method that may be performed by a medical device at for determining when sensing window ending time adjustment criteria are met.

FIG. 14 is a flow chart 776 of a method that may be performed by control circuit 206 at like-numbered block 776 of FIG. 13 for determining when A3 window ending time adjustment criteria are met according to one example. At block 782, control circuit 206 may determine if the A3 time metric is known. As described above, the A3 time metric may be unknown when two few A3 event times are available after N ventricular cycles. Too few A3 event times may be available when the A3 window is not started due to too many fast ventricular events or when the motion signal does not cross the low A3 threshold amplitude during a threshold number of the A3 windows.

If the A3 time metric is not known, control circuit 206 may determine if the cause of the unknown A3 time metric is due to too few A3 windows during the N ventricular events at block 784. Control circuit 206 may compare the number of A3 windows that occurred over the N ventricular events to a threshold number. When the number of A3 windows is less than a threshold number, e.g., less than 50% of the N ventricular cycles, the A4 sensing control parameter metrics may be insufficient to support an adjustment of the A3 window ending time since the A3 event time is unknown. Control circuit 206 may set the adjustment to zero at block 792 in response to too few A3 windows being started during the N ventricular cycles. In some examples, control circuit 206 may count an A3 window that is started, even if it does not reach its ending time, e.g., due to a premature ventricular contraction sensed as an R-wave during the A3 window. In other examples, control circuit may count an A3 window only if it is started and ends during the ventricular cycle.

When at least a threshold number of A3 windows occurred during the N ventricular cycles ("no" branch of block 784), control circuit 206 may determine at block 786 that the A3 time metric is not known due to too few A3 event times being determined over the N ventricular cycles. For example, when an A3 event time has been determined in less than 50% of the N ventricular cycles), the A3 time metric may be unknown due to too few A3 event times. In this case, the control circuit 206 may determine that the A3 window ending time should be decreased at block 788. Since the motion signal seldom crosses the low A3 threshold amplitude, resulting if few A3 event times, the risk of oversensing A3 events is low. The A3 window ending time may be shortened to promote A4 sensing during the A4 window.

Since the target A3 window ending time is not known when the A3 time metric is not known, control circuit 206 may determine the adjustment to the A3 window ending time at block 778 to be a predetermined decrement, e.g., 10 ms, 20 ms, 30 ms, 50 ms or other selected time interval. If the predetermined decrement would cause the A3 window ending time to be less than a minimum A3 window ending time, the adjustment determined at block 778 may be an adjustment to the minimum A3 window ending time (not less than the minimum A3 window ending time).

In other examples, rather than determining the A3 event time as unknown, and subsequently determine the A3 time metric to be unknown, when the motion signal does not cross the low A3 threshold amplitude, the A3 event time may be set to a specified value, e.g., Y ms less than the minimum A3 window ending time, where Y ms may be 50 ms or other predetermined value. When the motion signal stays low, e.g., less than the low A3 threshold amplitude during the A3 window, the likelihood of A3 event oversensing is small. As such, the A3 window ending time may be set to a relatively short time interval after the ventricular electrical event with a small probability of oversensing A3 events as A4 events. Therefore, when the motion signal does not cross the low A3 threshold amplitude in a given ventricular cycle, the A3 event time is set to a relatively short default time interval. The A3 time metric based on all A3 event times determined over the N ventricular cycles, which may include cycles in which the A3 event time is set to the low default value, is then known. Control circuit 206 may use the A3 time metric for setting a target A3 window ending time for determining the A3 window ending time adjustment. In this case, the criteria at block 786 for determining that the A3 time metric is not known due to too few A3 event times may be omitted.

When control circuit 206 determines that the A3 time metric is known at block 782 ("yes" branch), control circuit 206 may determine whether the pacing mode is an atrial tracking pacing mode and whether the A4 time metric is known at block 790. If neither of these conditions are true, e.g., if the pacing mode is a non-atrial tracking pacing mode (e.g., VDI, VVIR, etc.) or the A4 time metric is not known (e.g., due to two few A4 windows or too few A4 event times determined over N ventricular cycles), control circuit 206 determines if the current operating mode is a VDI pacing mode at block 791.

As described below in conjunction with FIG. 18, control circuit 206 may operate in a VDI pacing mode to adjust the A3 window ending time from an initial, starting A3 window ending time value, e.g., at the time of pacemaker implantation, before starting operations in an atrial tracking ventricular pacing mode. If the VDI pacing mode is in effect at block 791 control circuit 206 may advance to block 796. Otherwise, when the A4 time metric is not known and the pacing mode is not an atrial tracking pacing mode or the VDI pacing mode ("no" branches of both blocks 790 and 791), no adjustment is made to the A3 window ending time by control circuit 206 at block 792. Likewise, when the pacing mode is an atrial tracking ventricular pacing mode (e.g., VDD), but the A4 time metric is unknown ("no" branches of both blocks 790 and 791) no adjustment is made to the A3 window ending time at block 792 since any adjustment may not correctly set the A3 window ending time earlier than the A4 event when the A4 event time is unknown.

When the operating mode is an atrial tracking pacing mode and the A4 time metric is known ("yes" branch of block 790), control circuit 206 may determine whether a sufficient difference between the A4 time metric and the A3 time metric exists to shift the A3 window ending time. For example, control circuit 206 may determine if the difference between the A4 time metric and the A3 time metric is less than a threshold difference, e.g., less than 100 ms as an example. The threshold difference may be a predetermined fixed value in some examples. In other examples, the threshold difference may be an adjustable or variable threshold difference, e.g., scaled to the actual ventricular rate. For instance, the threshold difference may be a percentage of the actual ventricular rate interval so that as the ventricular rate increases, the threshold difference is decreased, and when the ventricular rate decreases the threshold difference is increased.

If the difference between the A4 time metric and the A3 time metric is less than the threshold difference ("yes" branch of block 794), control circuit 206 determines that no adjustment is to be made to the A3 window ending time at block 792. In this case, enough A3 event times and enough A4 event times are known from the N ventricular cycles so that both the A3 time metric and the A4 time metric are known. These known A3 and A4 time metrics suggest that the current A3 window ending time is set to a value that allows the A3 window to reliably end before the A4 event so that the A3 and A4 events are separated by the ending time and event times are reliably detected. However, the separation of the A3 and A4 event signals is relatively small so no shifting of the A3 window ending time is warranted.

When the difference between the A4 time metric and the A3 time metric is relatively large, e.g., at least 100 ms or more, as determined by control circuit 206 based on the comparison to the threshold difference at block 794, control circuit 206 advances to block 796 ("no" branch of block 794). In this case, the time difference from A3 events to A4 events is sufficiently large that a shift, either an increase or decrease, in the A3 window ending time may be justified.

At block 796, control circuit 206 determines if the A3 window ending time is less than or equal to the target A3 window ending time. As described above, in conjunction with FIG. 13, control circuit 206 may determine the target A3 window ending time based on the A3 time metric during a VDI pacing mode or based on the A3 time metric and the A4 time metric during a VDD pacing mode. When the current A3 window ending time is greater than the target A3 window ending time, control circuit 206 determines that the A3 window ending time should be decreased at block 788.

The current value of the A3 window ending time may be greater than the target A3 ending time when, for example, the A3 time metric is determined to be relatively short, e.g., when the A3 event times are set to default minimum values (e.g., the minimum A3 window ending time minus 50 ms) due to the low A3 threshold amplitude not being crossed. In this case, the target A3 window ending time may be at or near the minimum A3 window ending time. If control circuit 206 determines that the A3 window ending time should be decreased at block 788, the A3 window ending time is adjusted toward or to the minimum A3 sensing window ending time. In this way, the A3 window is shortened when the likelihood of A3 event oversensing is low due to relatively low amplitude A3 events (less than the low A3 threshold amplitude) or due to the A3 events occurring very early in the A3 window. Control circuit 206 shortens the A3 window ending time toward or to the minimum A3 window ending time to promote reliable A4 event sensing, even when the ventricular rate increases. Shortening the ending time of the A3 window effectively starts the A4 window earlier, with the low A4 sensing threshold amplitude in effect, increasing the likelihood of sensing the A4 event.

When control circuit 206 determines that the A3 window ending time should be decreased at block 788, control circuit 206 may determine the adjustment at block 778 (of FIG. 13) based on the current value of the A3 window ending time. The A3 window ending time may be decreased by a predetermined decrement, e.g., 10 ms, 15 ms, 20 ms or other selected decrement but not less than the target A3 window ending time or the minimum available setting of the target A3 window ending time. The minimum A3 window ending time may be 600 ms after the most recent preceding ventricular electrical event as one example.

If the A3 window time is less than (or equal) to the target A3 window ending time as determined at bock 796 ("yes" branch), control circuit 206 determines that the A3 window ending time should be increased at block 798 toward (or held at) the target A3 window ending time (without exceeding the target A3 window ending time). It is to be understood that when control circuit 206 determines that the A3 window ending time is equal to the target ending time, control circuit 206 determines that no adjustment to the ending time is to be made, e.g., the adjustment is 0 ms.

When control circuit 206 determines that the A3 window ending time adjustment is an increase at block 798 of FIG. 14, control circuit 206 may determine the adjustment at block 778 of FIG. 13 as a predetermined increment, e.g., 10 ms, 20 ms or other selected value, but not greater than the target A3 window ending time or a maximum allowable setting of the A3 window ending time, e.g., not greater than a maximum of 1000 ms after a most recent ventricular event. The minimum and maximum limits of the A3 window ending time may be programmable and tailored to a given patient and may be selected to be at least 100 ms apart in some examples. For instance, the minimum to maximum range of the A3 window ending time may be 600 ms to 700 ms or 700 ms to 800 ms in a given patient. In another patient the minimum to maximum range may be larger, e.g., 700 ms to 1000 ms. At block 780 of FIG. 13, control circuit 206 adjusts the A3 window ending time according to the adjustment determined at block 778, based on which adjustment criteria (increase, decrease or hold) were met at block 776 as described in conjunction with FIG. 14.

Figure 15:
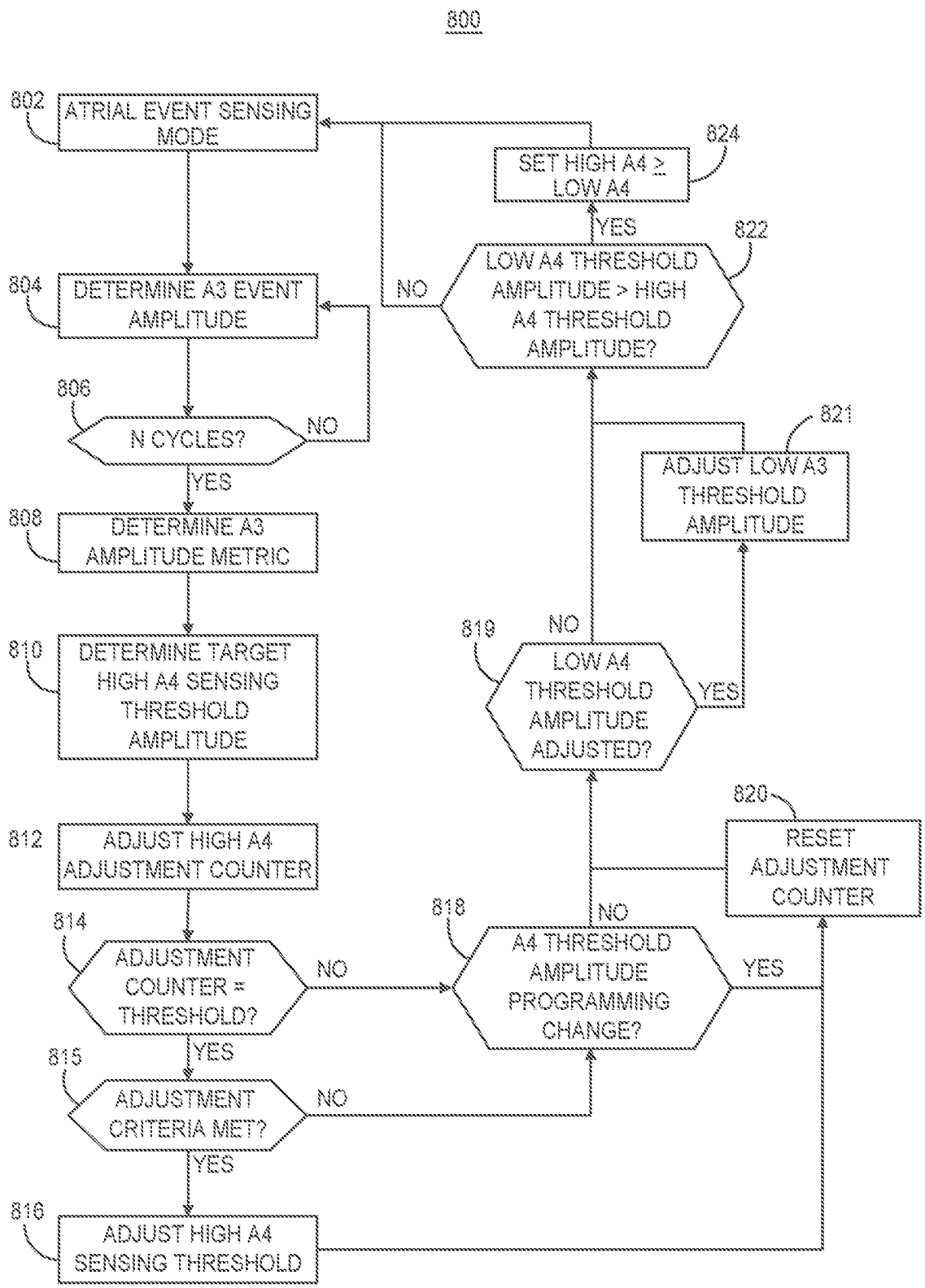
FIG. 15 is a flow chart of a method performed by a medical device for adjusting an atrial event high sensing threshold amplitude according to one example.

FIG. 15 is a flow chart 800 of a method performed by control circuit 206 for adjusting the high A4 sensing threshold amplitude according to one example. The high A4 sensing threshold amplitude is applied during the A3 window for detecting the A4 event when the A4 event signal is fused with the A3 event signal in the motion sensor signal. The high A4 sensing threshold amplitude may also be referred to as the first or early A4 sensing threshold since it is applied during the A3 window, before the low A4 sensing threshold amplitude, which may also be referred to as the second or late A4 sensing threshold because it is applied after the A3 window ending time. The high A4 sensing threshold amplitude may be adjusted based on the A3 event amplitudes, e.g., A3 event amplitude 760 shown in FIG. 12, determined over N ventricular cycles.

When control circuit 206 is operating in a pacing mode that includes atrial event sensing, e.g., a VDD or VDI pacing mode as determined at block 802, control circuit 206 determines the A3 event amplitude for each ventricular cycle at block 804 until N ventricular cycles have elapsed (as determined at block 806). It is to be understood that the A3 event amplitude, as well as other A4 sensing control parameter metrics, may be determined during or at the end of each ventricular cycle. In other examples, control circuit 206 may buffer the motion sensor signal in memory 210 for N ventricular cycles. Upon expiration of the N ventricular cycles, control circuit 206 may determine the A3 event amplitude (and/or other A4 sensing control parameter metrics) from the motion sensor signal buffered in memory 210. As described above, control circuit 206 may not determine an A3 event amplitude when an A3 window 740 (see FIG. 12) does not occur, e.g., due to an R-wave being sensed during the blanking period 730. When the A3 window 740 is started, control circuit 206 determines the maximum motion sensor signal amplitude during the A3 window as the A3 event amplitude.

In some examples, control circuit 206 may determine the A3 event amplitude only during ventricular cycles that include an A4 event detected during the A4 window. Alternatively, the A3 event amplitude may be determined for all ventricular cycles but ignored for the purposes of determining an A3 amplitude metric at block 808 when the A4 event is not detected during the A4 window. In some examples, A3 event amplitudes determined only during ventricular cycles that include a normal A4 event detection are used by control circuit 206 in adjusting the high A4 sensing threshold amplitude as described below. A normal A4 event detection is an A4 event detected at least a threshold time interval, e.g., 50 to 100 ms, after the A3 window ending time. The A3 event amplitude may more accurately reflect the amplitude of a true A3 event when the A4 event is known to be detected later during the A4 window. When the A4 event is detected early, fusion of the A3 and A4 events may be occurring, so that the A4 event is contributing to the A3 event amplitude determined by control circuit 206. As such, control circuit 206 may reject the A3 event amplitude that occurs during a ventricular cycle when the A4 event is detected during the A3 window, as an early A4 event within a threshold time interval of the A3 window ending time, or not detected at all.

In still other examples, the A3 event amplitude may be determined for all ventricular cycles, however different A3 event amplitude metrics may be determined by control circuit 206 according to the timing of the A4 event detection. As such, control circuit 206 may store the A3 event amplitudes in different buffers in memory 210 based on when the A4 event is detected. For example, control circuit 206 may determine and store A3 event amplitudes for all ventricular cycles in memory 210 and may flag or store in a different buffer the A3 event amplitudes determined for ventricular cycles that include only normal A4 event detections.

After N ventricular cycles have elapsed (block 806), control circuit 206 determines an A3 amplitude metric at block 808 based on the individually determined A3 event amplitudes. The A3 amplitude metric may be a mean, median, maximum or nth highest A3 event amplitude, as examples. When the A3 event amplitudes are determined over eight ventricular cycles, the A3 amplitude metric may be determined at the fourth highest A3 event amplitude as one example. If fewer than four A3 event amplitudes are known, e.g., due to fewer than four A3 windows being started during the eight ventricular cycles or the motion signal not crossing the low A3 threshold amplitude, the A3 amplitude metric may be determined to be unknown.

As described above, the A3 event amplitude may be determined as the maximum motion signal amplitude during the A3 window that is greater than the low A3 threshold amplitude, which may be set to a percentage of the low A4 sensing threshold amplitude. If the motion signal does not cross the low A3 threshold amplitude during the A3 window, the A3 event amplitude may be unknown for that ventricular cycle. As the low A4 sensing threshold amplitude is adjusted (e.g., as often as every N ventricular cycles), the low A3 threshold amplitude may be adjusted based on the adjusted low A4 sensing threshold amplitude. As such, the low A3 threshold amplitude is adjusted with the low A4 sensing threshold amplitude but the high A4 sensing threshold amplitude applied during the A3 window may be adjusted less frequently as described below.

As indicated above, the A3 amplitude metric may be determined based only on A3 event amplitudes determined for ventricular cycles having normal A4 event detections. For example, the A3 amplitude metric may be set to the maximum A3 event amplitude or a predetermined percentile or nth highest of the A3 event amplitudes associated with normal A4 event detection cycles. In other examples, the A3 amplitude metric may be determined based on a combination of A3 event amplitudes determined for ventricular cycles having normal A4 event detections and A3 event amplitudes determined for all ventricular cycles. For example, the A3 amplitude metric may be set to a percentile of all A3 event amplitudes that are greater than the A3 event amplitudes associated with normal A4 event detection cycles.

At block 810, control circuit 206 determines a target high A4 sensing threshold amplitude based on the A3 amplitude metric determined at block 808. The target high A4 sensing threshold amplitude may be determined based on a combination of the current low A4 sensing threshold amplitude and the A3 amplitude metric in some examples. For instance, control circuit 206 may determine the target high A3 sensing threshold amplitude as the sum of the current low A4 sensing threshold amplitude plus the A3 amplitude metric multiplied by a threshold factor. The threshold factor may be 1, 1.2, 1.5, 1.8, or other selected value. In some examples, the target high A4 sensing threshold amplitude is set to the low A4 sensing threshold amplitude plus 1.5 times the A3 amplitude metric plus an offset. Since a true A4 event signal during the A3 window may be fused with the A3 event signal, the fused A3/A4 amplitude may be a summation of the two individual events. Therefore, the target high A4 sensing threshold amplitude may be set based on a combination of the low A4 sensing threshold amplitude (or minimum detected A4 amplitude) and the A3 amplitude metric. The offset may be set to zero but may be set to other positive or negative values to fine tune the high A4 sensing threshold amplitude. In other examples, the target high A4 sensing threshold amplitude may be set to the maximum programmable low A4 sensing threshold amplitude plus the A3 amplitude metric multiplied by a selected factor, e.g., 1.5. When the A3 amplitude metric is unknown, the target high A4 sensing threshold amplitude may be determined to be unknown at block 810.

At block 812, control circuit 206 may adjust a high A4 threshold adjustment counter based on the target value determined at block 810. When the target high A4 sensing threshold amplitude is greater than the current high A4 sensing threshold amplitude, the adjustment counter is increased by 1. When the target high A4 sensing threshold amplitude is less than the current high A4 sensing threshold amplitude, control circuit 206 decreases the high A4 adjustment counter by 1. If the target value and the current value of the high A4 sensing threshold amplitude are equal, control circuit 206 does not change the value of the high A4 adjustment counter at block 812.

At block 814, control circuit 206 determines if the adjustment counter has reached a threshold. The adjustment counter may be increased up to a predetermined maximum value and decreased down to a predetermined minimum value. In other examples, instead of utilizing an adjustment counter, control circuit 206 may set a timer or counter for adjusting the high A4 sensing threshold amplitude on a scheduled basis, e.g., once per hour, once per four hours, once per eight hours, once per twelve hours, once per day or other selected frequency. When the adjustment counter reaches the maximum or minimum threshold value, or when a scheduled adjustment time is reached, control circuit 206 may determine if any other required high A4 sensing threshold adjustment criteria are met at block 815.

In some examples, control circuit 206 may determine if heart rate and/or the A3 window detection count is/are less than an adjustment threshold at block 815. During high heart rates, the large amplitude of the fused A3/A4 events will be determined as the A3 event amplitude and contribute to the A3 amplitude metric. Since the target value of the high A4 sensing threshold amplitude includes the A3 amplitude metric (in combination with the low A4 sensing threshold amplitude), the target value will be increased during periods of fused A3/A4 events. This elevated target value could, under some circumstances, cause the high A4 sensing threshold amplitude to be incremented above the fused A3/A4 amplitude and lead to undersensing of the fused A3/A4 events. As such, in some examples, the high A4 sensing threshold may be held at a current value (no adjustment) when sustained sensing in the A3 window is occurring. Accordingly, adjustment criteria applied at block 815 may require that the A3 window detection count is less than a threshold for one or more sets of N ventricular cycles and/or the actual ventricular rate is less than a threshold rate, e.g., less than 90 beats per minute indicating in order for adjustment criteria to be met. When the A3 window detection count is greater than the threshold count, e.g., greater than 3, and/or the heart rate is greater than 90 beats per minute, there is a likelihood of fused A3/A4 events contributing to an increased A3 event amplitude and an increased target high A4 sensing threshold amplitude. Control circuit 206 withholds adjusting to the high A4 sensing threshold amplitude under these conditions. The frequency of the adjustments to the high A4 sensing threshold amplitude may be controlled, therefore, by setting the maximum and minimum adjustment counter thresholds and may be further reduced when the A3 window detection count reaches a threshold value over one or more sets of N ventricular cycles.

When the adjustment counter reaches the maximum value and any other adjustment criteria are met at block 815, the high A4 sensing threshold amplitude may be increased at block 816. When the adjustment counter reaches the minimum value, the high A4 sensing threshold amplitude may be decreased at block 816. The range of the maximum and minimum values of the adjustment counter controls the frequency of adjustments made to the high A4 sensing threshold. The high A4 sensing threshold amplitude is increased or decreased only after the high A4 adjustment counter has progressively increased or decreased a threshold number of times. For example, the high A4 adjustment counter may be increased by one each time the target high A4 sensing threshold amplitude is greater than the current high A4 sensing threshold amplitude up to a maximum count of positive eight. When the maximum positive count of eight is reached (block 814) due to the target high A4 sensing threshold amplitude being consistently greater than the current setting of the high A4 sensing threshold, the high A4 sensing threshold may be increased by control circuit 206 at block 816.

The adjustment counter may be decreased by one each time the target high A4 sensing threshold amplitude is less than the current high A4 sensing threshold amplitude down to a minimum of negative eight, in some examples. When the threshold count of negative eight is reached (block 814), control circuit 206 may decrease the high A4 sensing threshold amplitude at block 816. In this way, the high A4 sensing threshold amplitude may be adjusted less often than the low A4 sensing threshold amplitude but will slowly track changes in the low A4 sensing threshold amplitude and the A3 amplitude metric. Other thresholds than the values of positive eight and negative eight may be applied to the high A4 adjustment counter, such as ±2, +4, +6 or other selected value, to control how often the high A4 sensing threshold amplitude is adjusted relative to the low A4 sensing threshold amplitude. Other techniques, other than the adjustment counter described herein, such as a timer or ventricular cycle counter may be used to limit or control the frequency at which the high A4 sensing threshold amplitude is adjusted.

When the adjustment counter reaches the maximum threshold value at block 814, control circuit 206 increases the high A4 sensing threshold amplitude toward the target high A4 sensing threshold amplitude at block 816. The adjustment may be a predetermined increment, e.g., 1 ADC unit or 0.12 $m/s^2$, 0.2 $m/s^2$, 0.3 $m/s^2$, or other selected increment. In other examples, the high A4 sensing threshold amplitude is adjusted to the target value or adjusted by a scaled increment based on the difference between the target value and the current high A4 sensing threshold amplitude.

When the adjustment counter reaches the minimum threshold value at block 814, control circuit 206 decreases the high A4 sensing threshold amplitude toward the target value at block 816. The high A4 sensing threshold amplitude may be decreased to the target value, by a predetermined decrement, e.g., 0.3 $m/s^2$, or by a scaled or adjustable decrement. The high A4 sensing threshold amplitude may be adjusted within a specified range, e.g., up to an A4 sensing threshold upper limit and down to a high A4 sensing threshold lower limit, which may be adjustable and based on or equal to the low A4 sensing threshold. After adjusting the high A4 sensing threshold amplitude, the adjustment counter is reset to zero (or a middle value between its maximum threshold and minimum threshold) at block 820.

If the adjustment counter has not reached a maximum or minimum threshold value at block 814 ("no" branch), control circuit 206 may return to block 802 without adjusting the high A4 sensing threshold amplitude. Control circuit 206 may proceed with determining the A3 amplitude metric for the next N ventricular cycles, as long as the pacing mode includes atrial sensing. In some examples, before returning to block 802, control circuit 206 may check at block 818 whether the high A4 sensing threshold or the low A4 sensing threshold amplitude has been reprogrammed by a user to a new value. If a programming change has been made to either the high A4 sensing threshold or the low A4 sensing threshold, the adjustment counter may be reset at block 820 to a starting value of zero or to a middle value of its range between a minimum threshold and a maximum threshold.

At block 819, control circuit 206 may determine if the low A4 sensing threshold amplitude has been adjusted after the most recent N ventricular cycles. If so, the low A3 threshold amplitude is adjusted at block 821. As described above, the low A3 threshold amplitude may be set based on the low A4 sensing threshold amplitude, e.g., to 75% or another specified percentage of the low A4 sensing threshold amplitude. Also described above in conjunction with FIG. 12, the A3 event amplitude determined at block 804 may be determined by control circuit 206 to be the maximum amplitude of the motion signal during the A3 window that is greater than the low A3 threshold amplitude. Accordingly, in some examples the low A3 threshold amplitude may be adjusted in response to any programming change of the low A4 sensing threshold amplitude and in response to any adjustment of the low A4 sensing threshold amplitude after N ventricular cycles in order to enable appropriate determination of the A3 event amplitude.

Additionally or alternatively, control circuit 206 may compare the high A4 sensing threshold amplitude to the low A4 sensing threshold amplitude at block 822 to verify that, if the low A4 sensing threshold amplitude is incremented, the high A4 sensing threshold amplitude is always at least equal to or greater than the low A4 sensing threshold amplitude. If control circuit 206 determines that the low A4 sensing threshold amplitude has been adjusted to be higher than the high A4 sensing threshold amplitude at block 822, control circuit 206 may adjust the high A4 sensing threshold amplitude to be at least equal to or greater than the low A4 sensing threshold amplitude at block 824. This adjustment at block 822 may be before the adjustment counter reaches a maximum or minimum threshold value. Control circuit 206 may return to block 802 to continue determining the A3 amplitude metric for updating the target high A4 sensing threshold amplitude after verifying that the operation mode still includes atrial event sensing.

Generally, the high A4 sensing threshold amplitude will be greater than the A3 event amplitude since it is set based on a combination of the A3 amplitude metric and a multiple of the low A4 sensing threshold amplitude. The high A4 sensing threshold amplitude set in this way avoids A3 event oversensing during the A3 window. When the heart rate increases, however, and the A3 event signal and the A4 event signal become fused, the fused A3/A4 event signal may cross the high A4 sensing threshold amplitude for appropriately sensing the A4 event. By adjusting the high A4 sensing threshold amplitude less frequently than the low A4 sensing threshold amplitude, oversensing of the A3 event is avoided while allowing sustained periods of sensing the fused A3/A4 event signal in the A3 window. The adjustment counter maximum and minimum thresholds may be set to limit adjustments to the high A4 sensing threshold amplitude of about 0.1 $m/sec^2$ per minute, as an example.

In the illustrative examples disclosed herein, control circuit 206 determines A4 sensing control parameter metrics from the motion sensor signal over non-overlapping sets of N consecutive ventricular cycles. Control circuit 206 determines an adjustment (increment, decrement, or no adjustment) to an A4 sensing control parameter based on the control parameter metrics after each set of N ventricular cycles (or after the adjustment counter reaches a threshold in the case of the high A4 sensing threshold amplitude). It is to be understood, however, that control circuit 206 may update A4 sensing control parameter metrics according to other schedules or frequencies, e.g., on a beat-by-beat basis or after a rolling number of overlapping N ventricular cycles. For instance, A4 sensing control parameter metrics may be updated after every four ventricular cycles based on the most recent eight ventricular cycles. It is recognized that the A4 sensing control parameter metrics may be updated according to a variety of schedules based on a variety of selected numbers of ventricular cycles (e.g., every one, two, three, four, five, eight, twelve, sixteen, twenty-four, or any other selected number of cycles).

Furthermore, it is recognized that the schedule and/or number of ventricular cycles required for updating one A4 sensing control parameter metric may be different than the schedule and/or number of ventricular cycles required for updating another A4 sensing control parameter metric. Different control parameter metrics may be updated at different frequencies. As described in conjunction with FIG. 15, the high A4 sensing threshold amplitude is adjusted less frequently than the low A4 sensing threshold amplitude and the A3 window ending time by implementing an adjustment counter that tracks differences in the target high A4 sensing threshold amplitude and the current high A4 sensing threshold amplitude. It is understood that various timers and/or counters may be implemented to control the schedule and frequency of different A4 sensing control parameter adjustments.

The scheduled frequency or number of ventricular cycles at which a given A4 sensing control parameter is adjusted may be fixed or adjustable. For example, if a given A4 sensing control parameter is not adjusted for a threshold time interval, e.g., within a specified number of sets of N ventricular cycles, due to adjustment criteria not being met, the number N may be increased so that determinations of A4 sensing control parameter metrics and A4 sensing control parameter adjustments are performed less often. To illustrate, if control circuit 206 determines that the low A4 sensing threshold amplitude has not been adjusted in response to the last six, eight, ten or other specified number of N ventricular cycles, the number N may be doubled, e.g., from eight to sixteen ventricular cycles. The A4 sensing control parameter metrics determined for use in adjusting the low A4 sensing threshold amplitude may be determined after every 16 ventricular cycles instead of every eight ventricular cycles, as an example.

When control circuit 206 determines that the low A4 sensing threshold amplitude is adjusted twice in a row (or other specified number of times) after 16 ventricular cycles, the number N may be reduced, e.g., back to 8 ventricular cycles, to allow more frequent adjustments to the low A4 sensing threshold amplitude. In some examples, the number of ventricular cycles used to determine A4 sensing control parameter metrics and adjust an A4 sensing control parameter may be increased one or more times based on the stability of the A4 sensing control parameter and may be reduced one or more times based on the frequency of adjustments to the A4 sensing control parameter. For example, at block 304 in FIG. 6 control circuit 206 may adjust N, the number ventricular cycles, based on how often one or more A4 sensing control parameter metrics are adjusted. Adjustments to the specified number of ventricular cycles may allow current drain of power source 214 required by control circuit 206 to perform processing and analysis of the motion signal to be conserved during periods of stable motion signal and cardiac rhythm (when frequent adjustments are not needed) while providing adjustments at increased frequency when the motion signal and or heart rhythm is changing due to changing patient conditions. As such, it is to be understood that control circuit 206 may adjust N, the number of ventricular cycles, used to determine the A4 sensing control parameter metrics when determining if N ventricular cycles are reached, e.g., at block 506 of FIG. 9, block 768 of FIG. 13, and block 806 of FIG. 15.

Among the A4 sensing control parameter metrics that may be determined by control circuit 206 for adjusting A4 sensing control parameters, with no limitation intended, are the applicable cycle count (ventricular cycles that include an A4 window), detected A4 count, minimum detected A4 amplitude or other A4 amplitude metric, early A4 count, normal A4 count, A3 window detection count (number of A4 events sensed during the A3 window), low A3 threshold amplitude, A3 time metric, A4 time metric, target A3 window ending time, A3 amplitude metric, and target high A4 sensing threshold amplitude, all of which are described above in conjunction with the accompanying figures.

The A4 sensing control parameter adjustments described herein involve determining A4 sensing control parameter metrics during ventricular cycles that may begin with a sensed R-wave or a ventricular pacing pulse. In some examples, control circuit 206 may be configured to determine a first set of A4 sensing control parameter metrics corresponding to ventricular cycles starting with a sensed R-wave and determine a second set of A4 sensing control parameter metrics corresponding to ventricular cycles starting with a ventricular pacing pulse. In this way, one set of A4 sensing control parameters may be adjusted for sensing the A4 event following a sensed R-wave and a second set of A4 sensing control parameters may be adjusted for sensing the A4 event following a ventricular pacing pulse. For instance, a post-sense A3 window ending time may be adjusted based on the A3 time metric and the A4 time metric determined following sensed R-waves. This post-sense A3 window ending time may be applied following sensed R-waves. A post-pace A3 window ending time may be adjusted based on the A3 time metric and the A4 time metric determined following ventricular pacing pulses and applied following ventricular pacing pulses. Likewise, post-pace and post-sense high A4 sensing threshold amplitudes and post-pace and post-sense low A4 sensing threshold amplitudes may be adjusted separately based on respective post-pace A4 sensing control parameter metrics and post-sense A4 sensing control parameter metrics.

Examples presented herein indicate that the A4 sensing control parameter adjustment methods may be performed during specified pacing operating modes for use in controlling A4 sensing during atrial tracking ventricular pacing modes. In some instances, the telemetry circuit 208 of pacemaker 14 may be receiving or sending telemetry signals or performing other temporary operations. Determining A4 sensing control parameter metrics and adjusting of A4 sensing control parameters may be suspended by control circuit 206 during at least some temporary operations, e.g., when adjustments to the A4 sensing control parameters may interfere with or confound the temporary operation or other functions of pacemaker 14 during the temporary operation.

It further is contemplated that the A4 sensing control parameters may be adjusted by a medical device during and for use in a sensing operating mode that does not necessarily include ventricular pacing. A4 sensing may be performed for monitoring an atrial rate or rhythm, discriminating ventricular tachyarrhythmias from supraventricular tachyarrhythmias or other applications that require atrial systolic event sensing but do not necessarily include ventricular pacing. As such the techniques disclosed herein are not limited to implementation for use in conjunction with ventricular pacing or in a ventricular pacemaker or other medical device that necessarily includes ventricular pacing operating modes.

Figure 16:
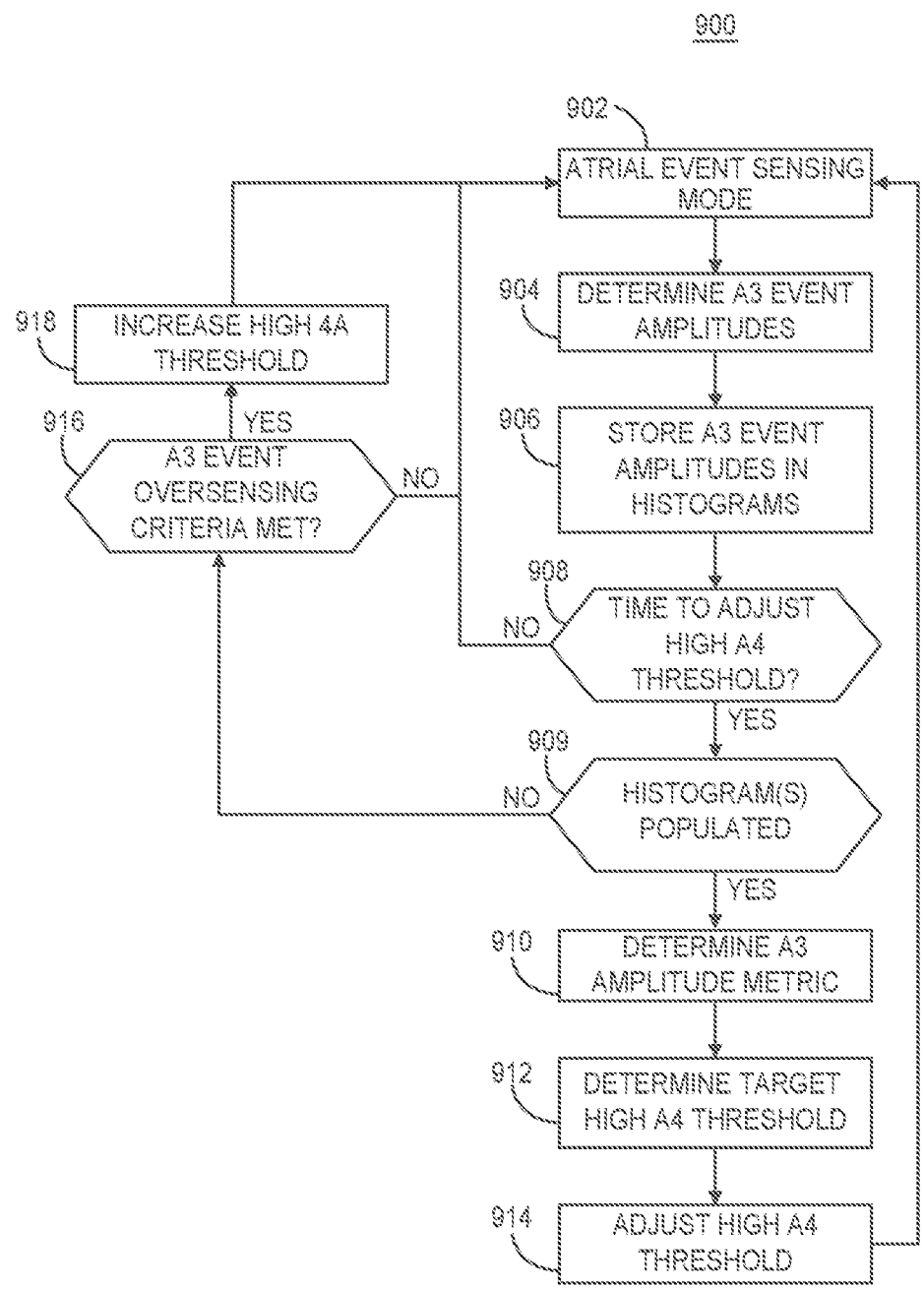
FIG. 16 is a flow chart 900 of a method that may be performed by control circuit 206 for adjusting the high A4 sensing threshold amplitude according to another example.

FIG. 16 is a flow chart 900 of a method that may be performed by control circuit 206 for adjusting the high A4 sensing threshold amplitude according to another example. When control circuit 206 is operating in an operating mode that includes atrial event sensing, as determined at block 902, A4 sensing control parameter metrics may be determined from the motion signal for use in adjusting the high A4 sensing threshold amplitude. At block 904, control circuit 206 determines A3 event amplitudes. In the method of FIG. 16, control circuit 206 may adjust the high A4 sensing threshold amplitude at scheduled adjustment time intervals, rather than based on an adjustment counter as described in conjunction with FIG. 15. As such, control circuit 206 may determine A3 event amplitudes for each ventricular cycle until the adjustment time interval expires (at block 908).

During the adjustment time interval, which may be several minutes, hours or days in various examples, the A3 event amplitude may be determined at block 904 for each ventricular cycle having an A3 window by determining the maximum amplitude of the motion sensor signal during the A3 window. In some examples, the A3 event amplitude is determined for a given ventricular cycle only when the A3 window reaches its ending time. In other examples, the A3 event amplitude is determined for all ventricular cycles in which the A3 window is started. As described above in conjunction with FIG. 12, the maximum amplitude of the motion signal may be required to be greater than the low A3 threshold in order to be determined as an A3 event amplitude.

At block 906, control circuit 206 may store the A3 event amplitudes in histogram bins allocated in memory 210. In some examples, the A3 event amplitudes are stored in two different histograms, each having multiple histogram bins assigned to different amplitude values or ranges. All determined A3 event amplitudes may be stored in one histogram, regardless of timing of A4 event detections. In the second histogram, A3 event amplitudes determined only for ventricular cycles including a normal A4 event detection may be stored. When an A4 event is sensed during the A4 window, or at least a threshold time interval later than the A3 window ending time, the ventricular cycle may be determined to be a "normal" A4 event cycle since the A4 event was not sensed early or during the A3 window. During these normal A4 event cycles, the maximum amplitude during the A3 window is most likely the A3 event, not a fused A3/A4 event, and therefore representative of the true A3 event amplitude with a high degree of confidence. As such, one histogram may be a normal A4 event histogram allocated for storing A3 event amplitudes for all ventricular cycles having a normal A4 event sensed at least a threshold time interval (e.g., 0-100 ms) later than the A3 window ending time.

In another example, in one histogram control circuit 206 may store only A3 event amplitudes that are determined to occur within a predetermined range of the A3 time metric or a currently determined median (or similar metric) of A3 event times determined over the adjustment time interval. For example, when the maximum amplitude during the A3 window is within 10 to 20 ms of the median A3 event time, control circuit 206 may store this maximum amplitude in the corresponding bin of the histogram. In this way, a portion of the A3 event amplitudes each determined as a maximum amplitude of the motion signal during the A3 window and within a threshold time range of an A3 time metric may be identified for use in determining an A3 amplitude metric. This A3 amplitude metric based on maximum amplitudes within a threshold time range of the A3 time metric may be more likely to correspond to true A3 events.

At block 908, control circuit 206 may determine when a scheduled adjustment time interval for adjusting the high A4 sensing threshold amplitude has expired. In some examples, the high A4 sensing threshold amplitude is adjusted once every 24 hours. In other examples, the scheduled adjustment time may be more often or less often and may be set to a variable time interval by control circuit 206 based on the time since pacemaker 14 implant, relative changes in A3 event amplitudes, A4 event amplitudes, a change in a target high A4 threshold value, the difference between a target high A4 threshold value and the current setting of the high A4 threshold, or other factors. If the adjustment time interval that is scheduled for adjusting the high A4 sensing threshold has not expired, control circuit 206 returns to block 902 to continue accumulating A3 event amplitudes for storing in histogram(s) in memory 210.

If the operating mode has changed from an atrial event sensing mode, control circuit 206 may wait until the atrial event sensing mode resumes. The A3 event amplitudes that have accumulated in memory 210 may be retained until the scheduled time for adjusting the high A4 sensing threshold arrives, with additional A3 event amplitudes being added to the histogram(s) in memory 210 whenever the operating mode includes atrial event sensing. Alternatively, the A3 event amplitudes may be cleared from memory 210 if the operating mode changes to a mode without atrial event sensing. Collection of A3 event amplitudes in memory 210 may be restarted the next time control circuit 206 begins operating in an operating mode that includes atrial event sensing.

When control circuit 206 determines that it is time to adjust the high A4 sensing threshold amplitude at block 908, control circuit 206 may determine if the histogram(s) are sufficiently populated at block 909. In some instances, there may be insufficient ventricular cycle lengths having a normal A4 event detection resulting in a low or sparsely populated histogram of the A3 event amplitudes for normal A4 event cycles. A threshold number of A3 event amplitudes may be required to be stored in the normal A4 event histogram in order to utilize the accumulated data for determining an A3 amplitude metric as described below. When control circuit 206 determines that less than a threshold number of the ventricular cycles are identified as normal A4 event ventricular cycles at block 909, control circuit 206 may withhold determining the A3 amplitude metric. When insufficient data exists, e.g., less than a threshold number of stored A3 event amplitudes for normal A4 event ventricular cycles, control circuit 206 may return to block 902 to continue accumulating A3 event amplitudes without adjusting the high A4 sensing threshold amplitude. In various examples, the high A4 sensing threshold amplitude may be adjusted when the next adjustment time interval expires or when a threshold number of A3 event amplitudes populate the normal A4 event histogram, or whichever occurs first.

In some examples, the limited number of A3 event amplitudes stored in the normal A4 event histogram may be due to A3 event oversensing. As described above, e.g., in conjunction with FIG. 10, when the A3 event is oversensed as the A4 event, e.g., due to the high A4 sensing threshold amplitude being set too low, the A4 window is not started.

This precludes determination and storage of the A3 event amplitude in the normal A4 event histogram. As such, control circuit 206 may determine if A3 event oversensing criteria are met at block 916 in response to less than a threshold number of A3 event amplitudes being stored in the normal A4 event histogram (as determined at block 909).

The A3 event oversensing criteria may be met at block 916 when greater than a threshold number of A3 event amplitudes are stored in a histogram for all ventricular cycles but less than a threshold number of amplitudes are stored in the histogram for only the normal A4 event ventricular cycles. In other examples, control circuit 206 may track the number of applicable cycles (the number of cycles having an A4 window starting after the expiration of the A3 window). When fewer than a threshold number of ventricular cycles over the scheduled adjustment time interval are applicable cycles, A3 event oversensing criteria may be met at block 916. In still other examples, control circuit 206 may determine the early A4 count (the number of A4 events sensed within a threshold time interval of the ventricular window ending time) and/or the A3 window detection count over the adjustment time interval. When either or the sum of these A3 window and early A4 counts is greater than a threshold, the A3 event oversensing criteria may be met at block 916. For instance, control circuit 206 may compare the early A4 count, the A3 window detection count, or the sum of both of these counts to the applicable cycle count or to the detected A4 count determined over the adjustment time interval. When the ratio or difference between the A3 window detection count, early A4 count or sum of both and the applicable cycle count (or the detected A4 count) is greater than a threshold, control circuit 206 may determine that the A3 event oversensing criteria are met at block 916.

If A3 event oversensing criteria are not met ("no" branch of block 916), control circuit 206 may return to block 902. When the A3 event oversensing criteria are met, control circuit 206 may increase the high A4 sensing threshold at block 918, e.g., by a predetermined increment. By increasing the high A4 sensing threshold amplitude, oversensing of A3 events may be reduced or avoided so that the histogram storing A3 event amplitudes determined from normal A4 event ventricular cycles may be sufficiently populated over the next scheduled adjustment time interval. In some examples, control circuit 206 increases the high A4 threshold amplitude at block 918 in response to less than a threshold number of A3 event amplitudes stored in the normal A4 event histogram (as determined at block 909) without requiring any additional A3 event oversensing criteria to be met at block 916.

When the time to adjust the high A4 sensing threshold is reached at block 908 and the histogram(s) are sufficiently populated (block 909), control circuit 206 determines an A3 amplitude metric at block 910 based on the A3 event amplitudes stored in memory 210. In some examples, the A3 amplitude metric may be a predetermined percentile of A3 event amplitudes stored for the ventricular cycles that include a normal A4 event detection. For instance, the A3 amplitude metric may be determined to be the 80th, 85th, 90th, or 95th percentile of the A3 event amplitudes determined from ventricular cycles including a normal A4 event detection.

At block 912, control circuit 206 may determine a target high A4 sensing threshold amplitude. The target high A4 sensing threshold amplitude may be determined based on the A3 amplitude metric. In other examples, the target high A4 sensing threshold amplitude is determined based on the A3 amplitude metric and all accumulated A3 event amplitudes stored in memory 210 over the scheduled adjustment time period, regardless of whether the A4 event is detected early or late in the associated ventricular cycles. In one example, the target high A4 sensing threshold amplitude is determined as a predetermined percentile of all A3 event amplitudes that are greater than the A3 amplitude metric. Example methods for determining the A3 amplitude metric and a target high A4 sensing threshold amplitude based on histograms of A3 event amplitudes are described below in conjunction with FIG. 17.

At block 914, control circuit 206 adjusts the high A4 sensing threshold amplitude toward the target high A4 threshold. In some examples, control circuit 206 adjusts the high A4 sensing threshold amplitude directly to the target value determined at block 912. In other examples, control circuit 206 may adjust the high A4 sensing threshold amplitude toward the target value by a predetermined adjustment value, which may be an increment or decrement as needed to adjust toward the target value. If the current high A4 sensing threshold amplitude is equal to the target value, no adjustment is made.

The adjustment value applied as an increment or decrement to the current high A4 sensing threshold amplitude to adjust toward the target high A4 sensing threshold may be fixed or variable. For example, the adjustment value may be fixed at 0.2 m/s$^2$, 0.4 m/s$^2$, 0.6 m/s$^2$, 0.8 m/s$^2$ or other selected value. In other examples, the adjustment value may be variable. For example, the adjustment increment/decrement may be set by control circuit 206 based on the time since pacemaker 14 implant. During the first days, weeks or months after implant, the adjustment increment/decrement may be set larger to enable adjustment toward the target high A4 threshold to occur more rapidly. The size of the adjustment increment/decrement may be decreased gradually or in one step after a specified time since pacemaker implant, e.g. after one week, one month or other selected time period. In other examples, the adjustment value of the increment/decrement may be variably adjusted by control circuit 206 based on the difference between the target high A4 threshold and the current setting of the high A4 threshold. In still other examples, the adjustment value may be adjusted based on the scheduled adjustment time interval that determines the frequency of high A4 sensing threshold adjustments. For instance, a smaller increment/decrement may be used when the scheduled adjustment time intervals are relatively short, e.g., less than every 12 hours, and a larger increment/decrement may be used when the schedule adjustment time intervals are relatively longer, e.g., every 12 hours or more.

After making the appropriate adjustment at block 914, control circuit 206 may clear the histogram bins (or a portion of the histogram bins) and return to block 902 to restart accumulating A3 event amplitudes when the operation mode includes atrial event sensing. Control circuit 206 may schedule the next time to adjust the high A4 sensing threshold amplitude, e.g., at a fixed time interval or adjustable time interval. As indicated above, control circuit 206 may schedule the time for adjusting the high A4 threshold amplitude according to a variable adjustment time interval, which control circuit 206 may set based on a difference between the current target high A4 sensing threshold amplitude a previously determined target high A4 sensing threshold amplitude, the time since implant of pacemaker 14, the difference between the target high A4 sensing threshold amplitude and the current setting of the high A4 sensing threshold amplitude, or other factors.

The histogram(s) storing the A3 event amplitudes may be cleared completely after adjusting the high A4 sensing threshold amplitude or on a first in first out basis such that some portion of the most recent A3 event amplitudes may remain in the histogram bin(s) and be included in the next determinations of the A3 amplitude metric and target high A4 sensing threshold amplitude. For example, the A3 event amplitude histogram bins may store data over a first time interval, e.g., 24 hours of data, but the high A4 sensing threshold may be adjusted after a second time interval which may be shorter than the first time interval, e.g., every 12 hours based on the most recent 24 hours of data. The oldest 12 hours of A3 event amplitude data may be cleared after adjusting the high A4 sensing threshold amplitude at block 914, and the most recent 12 hours of A3 event amplitude data may be saved in the histograms and compiled with the next 12 hours of new data. Alternatively, multiple histograms may be allocated in memory 210 to enable storing data in histograms over different overlapping time periods. A3 event amplitude data stored over a relatively longer period of time may represent a greater variation in heart rates, physical activity or other factors that may influence the timing of A4 events during ventricular cycles and/or the motion signal amplitude. Adjusting the high A4 sensing threshold amplitude at relatively shorter adjustment time intervals based long a longer data collection time interval allows the threshold amplitude to appropriately track any changes in the motion signal amplitude more frequently.

Figure 17:
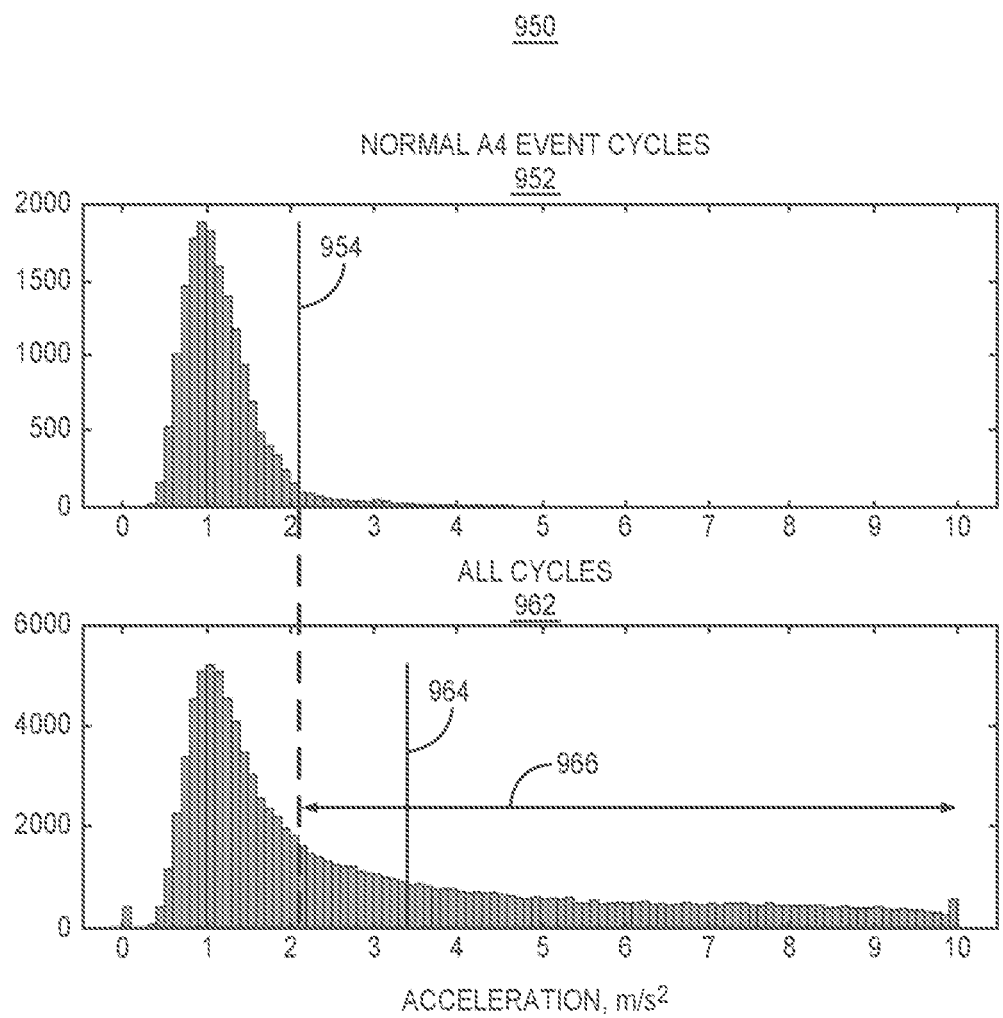
FIG. 17 is a diagram 950 of histograms of A3 event amplitudes that may be determined by control circuit 206 and stored in memory 210 for use in setting the high A4 sensing threshold amplitude according to some examples.

FIG. 17 is a diagram 950 of histograms 952 and 962 of A3 event amplitudes that may be determined by control circuit 206 and stored in memory 210 for use in adjusting the high A4 sensing threshold amplitude according to some examples. The A3 event amplitudes are plotted along the horizontal axis as acceleration measured in $m/s^2$ in bin ranges of 0.1 $m/s^2$. The frequency of occurrence of each amplitude bin range is plotted along the y-axis.

The top histogram 952 is a histogram of A3 event amplitudes determined from only ventricular cycles including normal A4 event detections. In these ventricular cycles, the A4 event is detected in response to the motion signal crossing the low A4 sensing threshold amplitude later than a threshold time interval, e.g., 0 to 100 ms, after the A3 window ending time (without crossing the high A4 sensing threshold amplitude during the A3 window). In some examples, all ventricular cycles having an A4 event sensed at least 50 ms later than the A3 window ending time are classified as normal A4 event cycles by control circuit 206. In these ventricular cycles, the determined A3 event amplitude is unlikely to be influenced by an A4 event (that occurs later in the ventricular cycle than the A3 event) and more likely corresponds to a true A3 event that is not fused with an A4 event.

Control circuit 206 may determine the A3 amplitude metric at block 910 of FIG. 16 as a predetermined percentile of the A3 event amplitudes included in normal A4 event histogram 952. In the example shown, the A3 amplitude metric is determined as the 95th percentile of the A3 event amplitudes stored in normal A4 event histogram 952. The line 954 marks the 95th percentile of the A3 event amplitudes included in histogram 952 and is referred to hereafter as the A3 amplitude metric 954 for this illustrative example. In some examples, control circuit 206 may set the target high A4 sensing threshold amplitude based on the A3 amplitude metric 954, e.g., to a percentage larger than the A3 amplitude metric 954 or by adding an offset to the A3 amplitude metric 954 and/or adding the low A4 sensing threshold amplitude to the value of the A3 amplitude metric 954. The added offset may be 0.2, 0.3, 0.5, 0.8, or 1.0 $m/s^2$ as examples. During an atrial tracking ventricular pacing mode, all or a vast majority of the motion sensor signal peak amplitudes represented in the normal A4 event histogram 952 should not be detected as A4 events by atrial event detector circuit 240. Thus, control circuit 206 may be configured to set the high A4 sensing threshold amplitude to a value that is equal to or higher than the A3 amplitude metric 954 to avoid oversensing A3 events.

The second, bottom histogram 962 represents all A3 event amplitudes determined over the predetermined time period for accumulating histogram data. Histogram 962 may therefore include A3 event amplitudes determined from ventricular cycles with A4 events detected during the A3 window, A4 events detected early after the A3 window ending time and "normal" A4 events detected a threshold time interval after the A3 window ending time (and possibly ventricular cycles with no sensed A4 event). As observed by histograms 952 and 962, higher frequencies of higher A3 event amplitudes, greater than the A3 amplitude metric 954, may occur when all A3 event amplitudes are stored in the histogram 962, presumably due to the effect of early A4 events and A4 events sensed during the A3 window contributing to the A3 event amplitudes. Thus, the higher A3 event amplitudes included in histogram 962, greater than the A3 amplitude metric 954, may represent ventricular cycles having fused A3/A4 events occurring during the A3 window or near the A3 window ending time.

Control circuit 206 may be configured to determine the target high A4 sensing threshold amplitude 964 at block 912 of FIG. 16 based on the A3 event amplitudes stored in histogram 962 that are greater than the A3 amplitude metric 954. These A3 event amplitudes that are higher than the A3 amplitude metric are shown over the range 966. In the illustrative example shown, the target high A4 sensing threshold amplitude 964 is set to a percentile of the A3 event amplitudes over the range 966. For instance, the target high A4 sensing threshold amplitude 964 may be set to the 10th, 20th, 25th, 30th or 35th percentile of the A3 event amplitudes greater than A3 amplitude metric 954, shown by range 966. In some cases an offset and/or the low A4 sensing threshold amplitude may be added to the value of the predetermined percentile 964 to determine the target high A4 sensing threshold amplitude. In other examples, the target high A4 sensing threshold amplitude may be set based on a percentile of all amplitudes stored in histogram 962. For instance, control circuit 206 may set the target high A4 sensing threshold amplitude to a predetermined percentile, e.g., 60th, 65th, 70th, or 75th percentile, of all A3 event amplitudes stored in histogram 962 and may optionally add an offset and/or the low A4 sensing threshold amplitude to the value of the specified percentile amplitude. Accordingly, in some examples, one of the histograms 952 or 962 may be populated for determining the target high A4 sensing threshold amplitude, but not necessarily both. In other examples, both are populated as described above for use in determining an A3 amplitude metric from a first portion of the A3 event amplitudes, e.g., those identified from normal A4 event ventricular cycles, and a target high A4 sensing threshold amplitude based on a second portion of the A3 event amplitudes, (e.g., those greater than the A3 amplitude metric).

Figure 18:
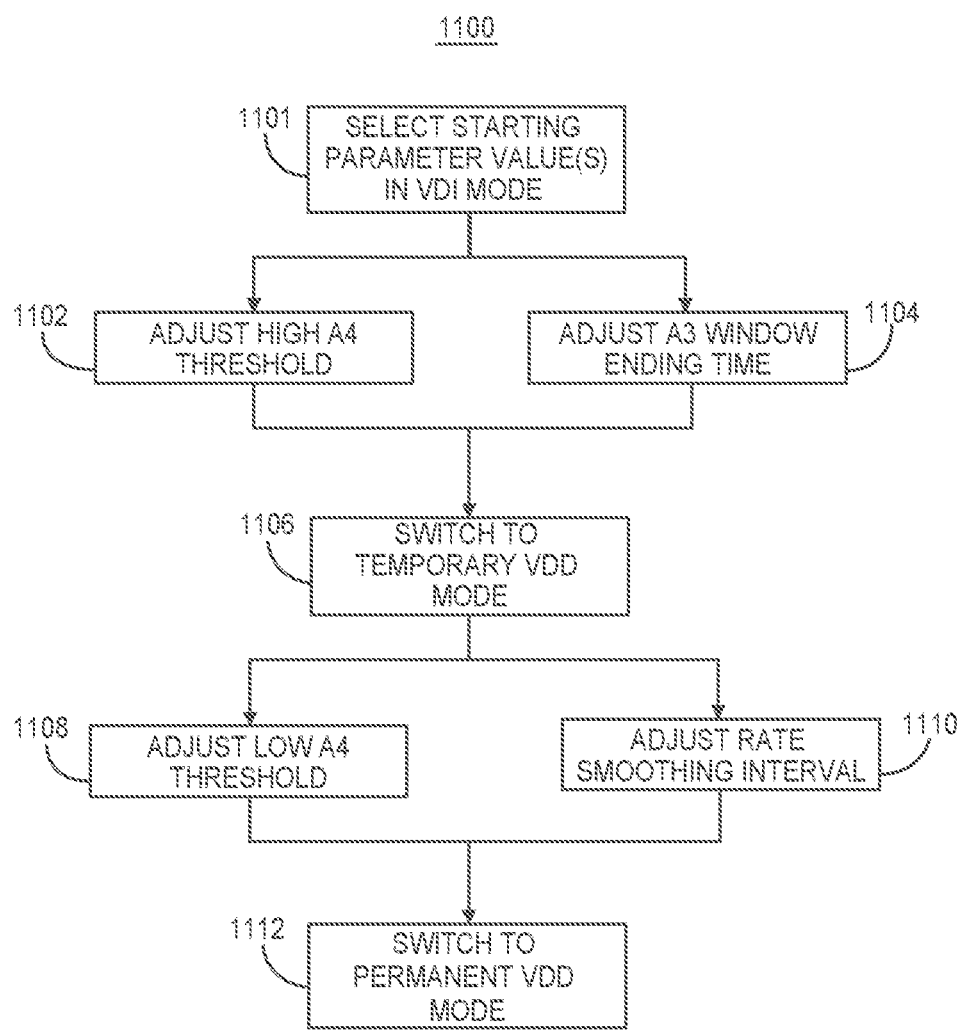
FIG. 18 is a flow chart of a method for adjusting atrial event sensing control parameters from starting values to operational values according to one example.

FIG. 18 is a flow chart 1100 of a method for adjusting selected atrial event sensing control parameters according to one example. Starting values of A4 sensing control parameters may be programmed by a clinician or may be automatically selected by control circuit 206. For example, control circuit 206 may determine a starting value of one or more A4 sensing control parameters at block 1101, such as the A3 window ending time and the first, higher and second, lower A4 sensing threshold amplitude values by determining A4 sensing control parameter metrics over an extended time interval or number of ventricular cycles when pacemaker 14 is initially implanted. The starting values may be selected by determining the A4 sensing control parameter metrics during a non-atrial tracking ventricular pacing mode that includes atrial sensing using the motion sensor signal, e.g., a VDI mode as indicated at block 1101. This pacing mode allows motion sensor signal features to be analyzed for determining control parameter metrics over a relatively extended period of time, e.g., one minute, two minutes, or five minutes, for selecting appropriate starting values of A4 sensing control parameters for the patient. Techniques that may be used for selecting starting control parameter values at block 1101 are generally disclosed in U.S. Patent Application No. 62/776,027, filed provisionally on Dec. 6, 2018, and corresponding non-provisional U.S. patent application Ser. No. 16/703,047, filed Dec. 4, 2019, now published as U.S. Patent Application Publication No. 2020/0179707 (Splett, et al.) and in U.S. Patent Application No. 62/776,034, filed provisionally on Dec. 6, 2018, and corresponding non-provisional U.S. patent application Ser. No. 16/703,320 filed on Dec. 4, 2019, now published as U.S. Patent Publication No. 2020/0179708 (Splett, et al.) all of which are incorporated herein by reference in their entirety.

The starting values of the A4 sensing control parameters may be based on motion sensor signal features that are determined over a relatively long, extended time period compared to the N ventricular cycles using for adjusting the A4 sensing control parameters using the techniques disclosed herein. For example, motion sensor signal features used to set the starting values may already be minutes or even hours old by the time the starting values are selected. Furthermore, when the starting values are selected during the VDI pacing mode, A4 events will not be consistently occurring during the A4 window. As such, after selecting starting values at block 1101, before control circuit 206 switches from the VDI pacing mode to a permanent atrial-tracking ventricular pacing mode, e.g., VDD pacing mode, control circuit 206 may adjust the starting values of one or more A4 sensing control parameters over a relatively shorter time interval, e.g., one to two minutes or over one or more sets of N ventricular cycles using the adjustment techniques disclosed herein. In this way, A4 sensing control parameters set to starting values based on "historical" data that may already be minutes or hours old may be further optimized to an operational value that is based on more recent, contemporaneously determined A4 sensing control parameter metrics. Adjusting the starting values to operational values just prior to switching to the permanent VDD pacing mode to deliver atrial synchronized ventricular pacing promotes optimal A4 sensing control parameter settings at the time of switching to the permanent VDD pacing mode.

After selecting a starting value for one or more A4 sensing control parameters at block 1101, control circuit 206 advances to blocks 1102 and 1104 to adjust the high A4 sensing threshold amplitude and the A3 window ending time, respectively, from their starting values. It is to be understood that blocks 1102 and 1104 may be parallel, simultaneous operations. The determination of A4 sensing control parameter metrics required for determining the adjustments to both the high A4 sensing threshold amplitude and the A3 window ending time may all be determined over every N ventricular cycles and with subsequent adjustment of both the high A4 sensing threshold amplitude and A3 window ending time at the end of each N ventricular cycles.

At blocks 1102 and 1104, control circuit 206 may continue to operate in the non-atrial tracking ventricular pacing mode, e.g., in the VDI pacing mode, for a predetermined time interval, e.g., one minute, two minutes, three minutes or other selected relatively short time interval or number of ventricular cycles, to adjust the high A4 sensing threshold amplitude and the A3 window ending time from starting values determined over a relatively longer set up process to currently relevant values, which may be referred to as "adjusted starting values." At block 1102, control circuit 206 determines A4 sensing control parameter metrics and adjusts the starting value of the high A4 sensing threshold amplitude using techniques described above in conjunction with FIGS. 12 and 15. For example, the A3 amplitude metric may be determined as the median maximum amplitude that occurs during the A3 windows over N consecutive ventricular cycles. The high A4 sensing threshold amplitude value may be adjusted after every eight ventricular cycles based on the fourth highest A3 event amplitude during the eight ventricular cycles. During this process of adjusting the high A4 sensing threshold amplitude from a starting value during the VDI pacing mode, the high A4 sensing threshold amplitude may be adjusted event N ventricular cycles without necessarily waiting for an adjustment threshold to be reached as described in conjunction with FIG. 15.

Control circuit 206 may determine a target value of the high A4 sensing threshold amplitude based on the A3 amplitude metric. The starting value of the high A4 sensing threshold amplitude determined during the set up process at block 1101 may be adjusted by a predetermined increment or decrement toward the target value after every N ventricular cycles (or as controlled by an adjustment counter as described in conjunction with FIG. 15). This process of adjusting the high A4 sensing threshold amplitude may be performed for an adjustment time interval, e.g., for one minute, two minutes, five minutes or other selected time interval, while operating in the VDI pacing mode. Control circuit 206 may store the adjusted high A4 sensing threshold amplitude during the temporary VDI pacing mode without applying the high A4 sensing threshold amplitude for A4 event sensing during the VDI pacing mode. The adjusted starting high A4 sensing threshold amplitude value may not go into effect until control circuit 206 switches to an atrial tracking ventricular pacing mode such that A4 events are not being detected by atrial event detector circuit 240 until all A4 sensing control parameters are adjusted to an operational value from the starting value.

At block 1104, control circuit 206 may determine the A3 event times, e.g., the latest low A3 threshold amplitude crossing by the motion sensor signal, which may be a negative going crossing, during the A3 window (set to end at the starting A3 window ending time). The A3 event times may be determined for N ventricular cycles. Control circuit 206 may determine an A3 time metric from the A3 event times and a target A3 window ending time as described above in conjunction with FIGS. 12 and 13. During the VDI pacing mode, the target A3 window ending time may be based on only the A3 time metric and not an A4 time metric since a reliable A4 time metric may be unknown during the non-atrial tracking ventricular pacing mode. The starting value of the A3 window ending time set a block 1101 may be adjusted based on the A3 time metric and target A3 window ending time every N ventricular cycles at block 1104.

The A3 window ending time established during the set up procedure at block 1101 may be based on the latest crossing of a test value of the low A3 threshold amplitude. The test value may set to a predetermined, fixed or default value, e.g., 0.9 m/s$^2$. The low A3 threshold amplitude used to determine the A3 event times at block 1104, however, may be better tailored to the patient when set by control circuit 206 to a percentage, e.g., 75%, of the starting value of the low A4 sensing threshold amplitude value determined during the set up procedure performed at block 1101, rather than a default value. Since the starting low A4 sensing threshold amplitude determined during the set up process at block 1101 is better tailored to the patient, the low A3 threshold amplitude set at block 1104 is also better tailored to the patient than a default value. The low A3 threshold amplitude set to a percentage of the starting low A4 sensing threshold amplitude may be a more appropriate threshold for the given patient in determining A3 event times and an A3 time metric for adjusting the A3 window ending time to a value that is currently relevant at block 1104.

For example, if the starting value of low A4 sensing threshold amplitude is set to 2.5 m/s$^2$ at the end of the set up process at block 1101, the low A3 threshold amplitude set to 75% of the starting low A4 sensing threshold amplitude is 1.9 m/s$^2$ instead of the default 0.9 m/s$^2$ threshold. This more relevant, patient-tailored, low A3 threshold amplitude may be used during the A3 windows over N ventricular cycles at block 1104 for detecting the latest low A3 threshold crossing times and adjusting the A3 window ending time. In this way, the A3 window ending time is better optimized for the patient at block 1104 from its starting value. The A3 window ending time may be adjusted every 8$^{th}$ ventricular cycle, or other selected number of ventricular cycles, for 2 minutes (or other adjustment time interval) at block 1104 to arrive at an adjusted starting A3 window ending time that goes into effect as the operational A3 window ending time upon switching to an atrial tracking ventricular pacing mode (e.g., VDD pacing mode).

After adjusting the starting A3 window ending time and/or the starting high A4 sensing threshold amplitude to operational values during the temporary VDI pacing mode at blocks 1102 and 1104, control circuit 206 may switch to a temporary atrial tracking pacing mode (e.g., VDD pacing mode) at block 1106. The operational values of the high A4 sensing threshold amplitude value and the A3 window ending value may be in effect upon switching to the temporary VDD pacing mode.

The low A4 sensing threshold amplitude may be adjusted at block 1108 from its starting value (selected during the set up process performed at block 1101). During this temporary VDD pacing mode, the low A4 sensing threshold amplitude may be adjusted from its starting value based on A4 sensing control parameter metrics determined over every N ventricular cycles using techniques generally described above in conjunction with FIGS. 7-11. Adjustments to the low A4 sensing threshold amplitude during the temporary VDD pacing mode with the contemporaneously optimized A3 window ending time determined at block 1104 now in effect is expected to tune the low A4 sensing threshold amplitude to an optimized value based on the A4 sensing control parameter metrics determined during the temporary VDD pacing mode. For example, the early A4 count, the applicable cycle count, the detected A4 count, and the A3 window detection count may be determined by control circuit 206 at block 1108 for use in adjusting the low A4 sensing threshold amplitude. These A4 sensing control parameter metrics are determined with the operational A3 window ending time and operational high A4 threshold amplitude determined at blocks 1104 and 1102, respectively, in effect.

At block 1110, control circuit 206 may determine a rate smoothing interval based on one or more ventricular cycle lengths occurring during the temporary VDD pacing mode. In some examples, a starting rate smoothing interval is set to the programmed lower rate interval. The median ventricular cycle length over N ventricular cycles, e.g., eight ventricular cycles may be determined by control circuit 206 at block 1110. An adjusted rate smoothing interval may be set by control circuit 206 to a predetermined interval longer than the median ventricular cycle length, e.g., 100 to 150 ms longer than the median ventricular cycle length. The rate smoothing interval may be updated every N ventricular cycles for a predetermined time interval, e.g., two minutes, during the temporary VDD pacing mode at block 1110.

Control circuit 206 may enable rate smoothing during the temporary VDD mode to promote and maintain atrioventricular synchrony while A4 sensing control parameter metrics are being determined for adjusting the low A4 sensing threshold. The rate smoothing interval may be adjusted during the temporary VDD pacing mode at block 1110 at a higher frequency than the low A4 sensing threshold in some examples. For example, a median or fourth fastest ventricular cycle length may be determined out of the most recent eight ventricular cycles after every ventricular cycle on a rolling basis. The rate smoothing interval may be set by control circuit 206 to the updated median ventricular cycle length plus a specified offset. Control circuit 206 may update the rate smoothing interval on every ventricular cycle so that the VV pacing interval is set to the updated rate smoothing interval on a beat-by-beat basis in some examples. If the VV pacing interval that is set to the rate smoothing interval expires, atrioventricular synchrony is expected to be maintained with appropriate timing of the A4 window encompassing the A4 event signal. By maintaining atrioventricular synchrony during the temporary VDD pacing mode, the A4 sensing control parameter metrics determined at block 1108 for adjusting the low A4 sensing threshold amplitude will enable control circuit 206 to adjust the low A4 sensing threshold amplitude to an optimal value for the patient.

As such, it is to be understood that blocks 1108 and 1110 may be performed in simultaneous parallel operations. For example, every N ventricular cycles control circuit 206 may determine the A4 sensing control parameter metrics required for determining the adjustment to the low A4 sensing threshold amplitude. Concurrently, on every ventricular cycle control circuit 206 may determine an updated ventricular cycle length metric for adjusting the rate smoothing interval as often as every ventricular cycle. The final adjusted values of the A4 sensing control parameters determined at blocks 1102, 1104 and/or 1108 and the latest updated rate smoothing interval may all go into effect as operational values upon switching to the permanent VDD pacing mode at block 1112.

After adjusting the starting value of the low A4 sensing threshold amplitude and adjusting the rate smoothing interval during the temporary VDD pacing mode over a predetermined time interval or number of ventricular cycles, control circuit 206 may switch to a permanent atrial tracking ventricular pacing mode at block 1112, e.g., the VDD pacing mode, with the operational values of the A4 sensing control parameters and adjusted rate smoothing interval in effect. In this way, starting values of the A4 sensing control parameters, which may be programmed by a user or determined during a set up process at block 1101 over a relatively longer time period, can be adjusted to operational values that are more currently relevant values based on more recent motion sensor signal amplitude and timing features used to determine A4 sensing control parameter metrics. The rate smoothing interval is set to a currently relevant value based on the current ventricular rate. These operational values of the A4 sensing control parameter metrics and the rate smoothing interval go into effect upon switching to the VDD pacing mode to provide optimized atrial tracking ventricular pacing.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising: a pulse generator configured to produce electrical stimulation pulses; a motion sensor configured to produce a motion signal; and a control circuit configured to: control the pulse generator in producing the electrical stimulation pulses for delivering a therapy; set a plurality of sensing control parameters comprising a ventricular diastolic event window ending time; sense first atrial events from the motion signal during a plurality of ventricular cycles according to the sensing control parameters; determine a features of the motion signal for each ventricular cycle of at least a portion of the plurality of ventricular cycles; determine at least one metric of the motion signal based on the determined features, wherein determining the at least one metric comprises: identifying each ventricular cycle of the plurality of ventricular cycles that is longer than the ventricular diastolic event window ending time; and determining a count of the plurality of ventricular cycles that are identified as being longer than the ventricular diastolic event window ending time; adjust a sensing control parameter of the plurality of sensing control parameters based on the at least one metric; sense a second atrial event from the motion signal according to the adjusted sensing control parameter; and generate an atrial sensed event signal in response to sensing the second atrial event.

2. The medical device of claim 1, wherein the control circuit is further configured to:
set the plurality of control parameters by:
setting a high sensing threshold amplitude extending to an expiration of the ventricular diastolic event window ending time; and
setting a low sensing threshold amplitude starting from the expiration of the ventricular diastolic event window ending time after the high sensing threshold amplitude;
sense each of the first atrial events during the plurality of ventricular cycles in response to an earliest crossing of one of the high sensing threshold amplitude and the low sensing threshold amplitude by the motion signal; and
adjust the sensing control parameter by adjusting at least one of the ventricular diastolic event window ending time, the high sensing threshold amplitude or the low sensing threshold amplitude.

3. The medical device of claim 2, wherein the control circuit is further configured to:
determine the features by determining a time of each of the first atrial events sensed during the plurality of ventricular cycles;
determine the at least one metric based on the determined time of each of the first atrial events sensed during the plurality of ventricular cycles by determining at least one of:
an early atrial event count by counting each of the first atrial events that are sensed after the ventricular diastolic event window ending time and before a threshold time interval;
a normal atrial event count by counting each of the first atrial events that are sensed at or later than the early event threshold time interval; and
a ventricular diastolic window atrial event count by counting each of the first atrial events that are sensed before the ventricular diastolic event window ending time.

4. The medical device of claim 3, wherein the control circuit is configured to:
determine that ventricular diastolic event oversensing criteria are met based on at least the early atrial event count; and
adjust the sensing control parameter based on the early atrial event count by increasing the low sensing threshold amplitude in response to the ventricular diastolic event oversensing criteria being met.

5. The medical device of claim 3, wherein the control circuit is configured to:
determine that regular atrial event sensing criteria are met based on at least the normal atrial event count; and
adjust the sensing control parameter based on the normal atrial event count by increasing the low sensing threshold amplitude in response to the regular atrial event sensing criteria being met.

6. The medical device of claim 3, wherein the control circuit is configured to:
 determine that atrial event undersensing criteria are met based on at least the normal atrial event count; and
 adjust the sensing control parameter based on the normal atrial event count by decreasing the low sensing threshold amplitude in response to the atrial event undersensing criteria being met.

7. The medical device of claim 2, wherein the control circuit is further configured to:
 determine the features by determining a maximum amplitude of the motion signal after the ventricular diastolic event window ending time for each of the plurality of ventricular cycles that is longer than the ventricular diastolic event window ending time; and
 determine the at least one metric by determining a minimum one of the maximum amplitudes; and
 adjust the sensing control parameter by adjusting the low sensing threshold amplitude based on the minimum one of the maximum amplitudes.

8. The medical device of claim 2, wherein the control circuit is further configured to:
 determine the features by determining a latest crossing time of a ventricular diastolic event threshold amplitude occurring before the ventricular diastolic event window ending time;
 determine the at least one metric by determining a ventricular diastolic event time based on the determined latest crossing times; and
 adjust the sensing control parameter by adjusting the ventricular diastolic event window ending time based on the ventricular diastolic event time.

9. The medical device of claim 8, wherein the control circuit is configured to set the ventricular diastolic event threshold amplitude based on the low sensing threshold amplitude.

10. The medical device of claim 8, wherein the control circuit is further configured to:
 determine the features by determining an earliest crossing time of the low sensing threshold amplitude;
 determine the at least one metric by determining an atrial event time based on the determined earliest crossing times; and
 adjust the ventricular diastolic event window ending time based on the ventricular diastolic event time and the atrial event time.

11. The medical device of claim 2, wherein the control circuit is further configured to:
 determine the features by determining a maximum amplitude of the motion signal that precedes the ventricular diastolic event window ending time;
 determine the at least one metric by determining a ventricular diastolic event amplitude based on the determined maximum amplitudes; and
 adjust the sensing control parameter by adjusting the high sensing threshold amplitude based on the ventricular diastolic event amplitude and the low sensing threshold amplitude.

12. The medical device of claim 11, wherein the control circuit is configured to:
 determine a target high threshold amplitude based on a combination of the ventricular diastolic event amplitude and the low sensing threshold amplitude;
 determine a difference between the target high threshold amplitude and the high sensing threshold amplitude;
 adjust a counter value based on the difference;
 determine that the counter value is equal to one of a maximum threshold and a minimum threshold; and
 adjust the high sensing threshold amplitude toward the target high threshold amplitude in response to the counter being equal to one of the maximum threshold or the minimum threshold.

13. The medical device of claim 2, wherein the control circuit is further configured to:
 determine the features by determining a first plurality of maximum amplitudes of the motion signal preceding the ventricular diastolic event window ending time for each of the plurality of ventricular cycles having one of the first atrial events sensed after the ventricular diastolic event window ending time;
 determine the at least one metric by determining a first percentile of the first plurality of maximum amplitudes;
 determine a second plurality of maximum amplitudes of the motion signal preceding the ventricular diastolic event window ending time for each of the plurality of ventricular cycles;
 determine a target high sensing threshold by determining a second percentile of the second plurality of maximum amplitudes that are greater than the metric; and
 adjust the sensing control parameter by adjusting the high sensing threshold amplitude based on the target high sensing threshold.

14. The medical device of claim 2, wherein the control circuit is configured to:
 determine that the atrial sensed event signal is generated before the ventricular diastolic event window ending time expires; and
 extend the ventricular diastolic event window ending time until a subsequent ventricular electrical event in response to determining that the atrial sensed event signal is generated before the ventricular diastolic event window ending time expires.

15. The medical device of claim 1, further comprising a pulse generator configured to generate a pacing pulse in response to the atrial sensed event signal.

16. The medical device of claim 15, further comprising:
 a housing enclosing the motion sensor, the control circuit and the pulse generator; and
 a pair of electrodes on the housing and coupled to the pulse generator.

17. A method, comprising: producing electrical stimulation pulses for delivering a therapy;
 producing a motion signal by a motion sensor;
 setting a plurality of sensing control parameters comprising a ventricular diastolic event window ending time;
 sensing first atrial events from the motion signal during a plurality of ventricular cycles according to the sensing control parameters;
 determining a features of the motion signal for each ventricular cycle of at least a portion of the plurality of ventricular cycles;
 determining at least one metric of the motion signal based on the determined features wherein determining the at least one metric comprises:
  identifying each ventricular cycle of the plurality of ventricular cycles that is longer than the ventricular diastolic event window ending time;
  determining a count of the plurality of ventricular cycles that are identified as being longer than the ventricular diastolic event window ending time;
 adjusting a sensing control parameter of the plurality of sensing control parameters based on the at least one metric;

sensing a second atrial event from the motion signal according to the adjusted sensing control parameter; and generating an atrial sensed event signal in response to sensing the second atrial event.

18. The method of claim 17, wherein:

setting the plurality of control parameters further comprises:
  setting a high sensing threshold amplitude extending to an expiration of the ventricular diastolic event window ending time; and
  setting a low sensing threshold amplitude starting from the expiration of the ventricular diastolic event window ending time after the high sensing threshold amplitude;
sensing each of the first atrial events in response to an earliest crossing by the motion signal of one of the high sensing threshold amplitude and the low sensing threshold amplitude during a respective one of the plurality of ventricular cycles; and
  adjusting the sensing control parameter comprises adjusting at least one of the ventricular diastolic event window ending time, the high sensing threshold amplitude or the low sensing threshold amplitude.

19. The method of claim 18, further comprising:

determining the features by determining a time of each of the first atrial events sensed during the plurality of ventricular cycles; and determining the at least one metric based on the determined time of each of the first atrial events sensed during the plurality of ventricular cycles by determining at least one of:
  an early atrial event count by counting each of the first atrial events that are sensed after the ventricular diastolic event window ending time and before a threshold time interval;
  a normal atrial event count by counting each of the first atrial events that are sensed at or later than the early event threshold time interval; and
  a ventricular diastolic window atrial event count by counting each of the first atrial events that are sensed before the ventricular diastolic event window ending time.

20. The method of claim 19, comprising:

determining that ventricular diastolic event oversensing criteria are met based on at least the early atrial event count; and adjusting the sensing control parameter based on the early atrial event count by increasing the low sensing threshold amplitude in response to the ventricular diastolic event oversensing criteria being met.

21. The method of claim 19, comprising:

determining that regular atrial event sensing criteria are met based on at least the normal atrial event count; and adjusting the sensing control parameter based on the normal atrial event count by increasing the low sensing threshold amplitude in response to the regular atrial event sensing criteria being met.

22. The method of claim 19, comprising:

determining that atrial event undersensing criteria are met based on at least the normal atrial event count; and adjusting the sensing control parameter based on the normal atrial event count by decreasing the low sensing threshold amplitude in response to the atrial event undersensing criteria being met.

23. The method of claim 18, further comprising:

determining the features by determining a maximum amplitude of the motion signal after the ventricular diastolic event window ending time for each of the plurality of ventricular cycles that is longer than the ventricular diastolic event window ending time;

determining the at least one metric by determining a minimum one of the maximum amplitudes; and adjusting the sensing control parameter by adjusting the low sensing threshold amplitude based on the minimum one of the maximum amplitudes.

24. The method of claim 18, further comprising:

determining the features by determining a latest crossing time of a ventricular diastolic event threshold amplitude occurring before the ventricular diastolic event window ending time;

determining the at least one metric by determining a ventricular diastolic event time based on the determined latest crossing times; and adjusting the sensing control parameter by adjusting the ventricular diastolic event window ending time based on the ventricular diastolic event time.

25. The method of claim 24, comprising setting the ventricular diastolic event threshold amplitude based on the low sensing threshold amplitude.

26. The method of claim 24, further comprising:

determining the features by determining an earliest crossing time of the low sensing threshold amplitude;

determining the at least one metric by determining an atrial event time based on the determined earliest crossing times; and adjusting the ventricular diastolic event window ending time based on the ventricular diastolic event time and the atrial event time.

27. The method of claim 17, further comprising:

determining the features by determining a maximum amplitude of the motion signal that precedes the ventricular diastolic event window ending time;

determining the at least one metric by determining a ventricular diastolic event amplitude based on the determined maximum amplitudes; and adjusting the sensing control parameter by adjusting the high sensing threshold amplitude based on the ventricular diastolic event amplitude and the low sensing threshold amplitude.

28. The method of claim 27, comprising:

determining a target high threshold amplitude based on a combination of the ventricular diastolic event amplitude and the low sensing threshold amplitude;

determining a difference between the target high threshold amplitude and the high sensing threshold amplitude;

adjusting a counter value based on the difference;

determining that the counter value is equal to one of a maximum threshold and a minimum threshold; and adjusting the high sensing threshold amplitude toward the target high threshold amplitude in response to the counter value being equal to one of the maximum threshold or the minimum threshold.

29. The method of claim 18, further comprising:

determining the features by determining a first plurality of maximum amplitudes of the motion signal preceding the ventricular diastolic event window ending time for each of the plurality of ventricular cycles having one of the first atrial events sensed after the ventricular diastolic event window ending time;

determining the at least one metric by determining a first percentile of the first plurality of maximum amplitudes;

determining a second plurality of maximum amplitudes of the motion signal preceding the ventricular diastolic event window ending time for each of the plurality of ventricular cycles;

determining a target high sensing threshold by determining a second percentile of the second plurality of maximum amplitudes that are greater than the metric; and adjusting the sensing control parameter by adjusting the high sensing threshold amplitude based on the target high sensing threshold.

30. The method of claim 17, comprising:

determining that the atrial sensed event signal is generated before the ventricular diastolic event window ending time expires; and extending the ventricular diastolic event window ending time until a subsequent ventricular electrical event in response to determining that the atrial sensed event signal is generated before the ventricular diastolic event window ending time expires.

31. The method of claim 17, comprising generating a pacing pulse in response to the atrial sensed event signal.

32. A non-transitory, computer-readable storage medium comprising a set of instructions which, when executed by a control circuit of a medical device, cause the medical device to: produce electrical stimulation pulses for delivery a therapy;

produce a motion signal by a motion sensor;

set a plurality of sensing control parameters comprising a ventricular diastolic event window ending time;

sense first atrial events from the motion signal during a plurality of ventricular cycles according to the sensing control parameters;

determine a features of the motion signal for each ventricular cycle of at least a portion of the plurality of ventricular cycles;

determine a at least one metric of the motion signal based on the determined features, wherein determining the at least one metric comprises;

identifying each ventricular cycle of the plurality of ventricular cycles that is longer than the ventricular diastolic event window ending time;

determining a count of the plurality of ventricular cycles that are identified as being longer than the ventricular diastolic event window ending time;

adjust a sensing control parameter of the plurality of sensing control parameters based on the at least one metric;

sense a second atrial event from the motion signal according to the adjusted sensing control parameter; and generate an atrial sensed event signal in response to sensing the second atrial event.

* * * * *